(12) United States Patent
Cho et al.

(10) Patent No.: US 6,784,346 B1
(45) Date of Patent: Aug. 31, 2004

(54) VALUE-ADDED TRAITS IN GRAIN AND SEED TRANSFORMED WITH THIOREDOXIN

(75) Inventors: Myeong-Je Cho, Alameda, CA (US);
Peggy G. Lemaux, Moraga, CA (US);
Bob B. Buchanan, Berkeley, CA (US);
Joshua Wong, San Francisco, CA (US);
Corina Marx, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/538,864

(22) Filed: Mar. 29, 2000

Related U.S. Application Data

(60) Provisional application No. 60/177,739, filed on Jan. 21, 2000, provisional application No. 60/177,740, filed on Jan. 21, 2000, provisional application No. 60/169,162, filed on Dec. 6, 1999, provisional application No. 60/127,198, filed on Mar. 31, 1999, and provisional application No. 60/126,736, filed on Mar. 29, 1999.

(51) Int. Cl.$^7$ ................................................ A01H 5/00
(52) U.S. Cl. .................... 800/320; 800/295; 800/320.3; 800/278; 800/287
(58) Field of Search ................................ 800/278, 295

(56) References Cited

U.S. PATENT DOCUMENTS

| | | | | |
|---|---|---|---|---|
| 5,543,576 A | * | 8/1996 | van Ooijen et al. | ........ 800/250 |
| 5,569,833 A | * | 10/1996 | Vincentz et al. | ............ 800/205 |
| 5,792,506 A | | 8/1998 | Buchanan et al. | |
| 5,889,189 A | * | 3/1999 | Rodriguez | ................... 800/205 |
| 5,952,034 A | | 9/1999 | Buchanan et al. | |
| 6,113,951 A | | 9/2000 | Buchanan et al. | |
| 6,114,504 A | | 9/2000 | Buchanan et al. | |
| 6,190,723 B1 | | 2/2001 | Buchanan et al. | |

FOREIGN PATENT DOCUMENTS

WO    WO 96/03505    2/1996

OTHER PUBLICATIONS

Shi et al. Plant Molecular Biology. 32:653–662, 1996.*
Rivera–Madrid et al. PNAS USA 92:5620–5624, Jun. 1995.*
Sewalt et al. J. Agric. Food Chem. 1997, 45, 1977–1983.*
Ishiwatari et al. (Planta, 1995, 195(3)456–463).*
Gautier et al. (1998, European Journal of Biochemistry, 252:314–324).*
Brugidou et al. (Mol. Gen. Genet (1993)238:285–293).*
Bower et al. (The Plant Cell, vol. 8:1641–1650).*
Marris et al. (Plant Molecular Biology 10:359–366 (1988)).*
Brandt et al. (Carlsberg Res. Commun. vol. 50, p. 333–345 (1985)).*
Cho, M.–J., et al., "Subcellular Targeting of Barley Hordein Promoter–uidA Fusions in Transgenic Barley Seed" *In Vitro Cellular and Developmental Biology* 34(3)part 2:48A (1998) abstract only.

* cited by examiner

*Primary Examiner*—Jeffrey Fredman
*Assistant Examiner*—Juliet C. Switzer
(74) *Attorney, Agent, or Firm*—Morrison & Foerster LLP

(57) ABSTRACT

Compositions and methods of use are provided herein to make and use transgenic plants with value-added traits.

32 Claims, 23 Drawing Sheets

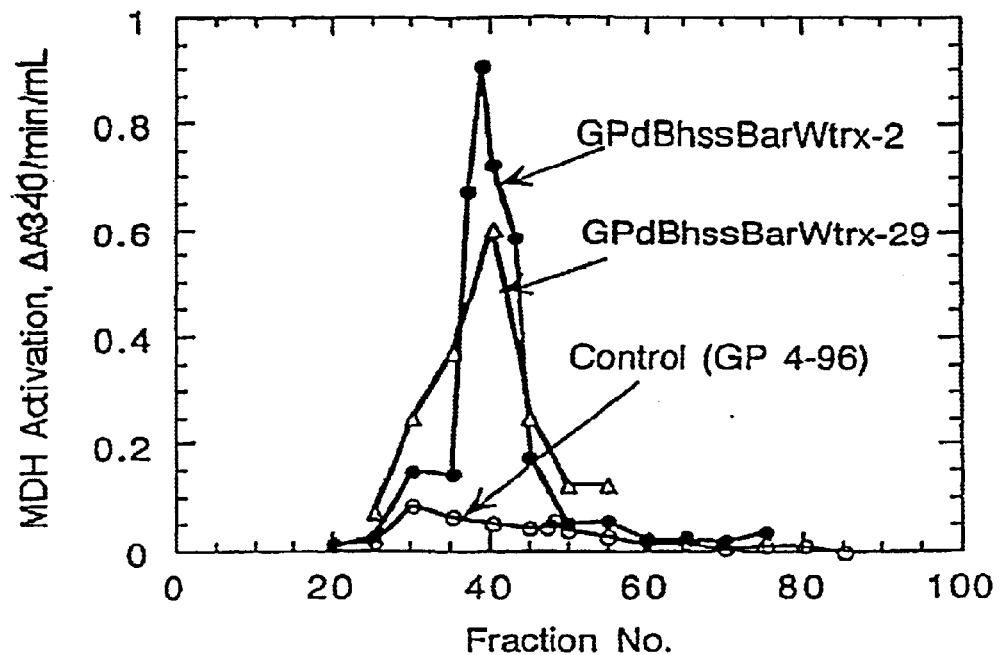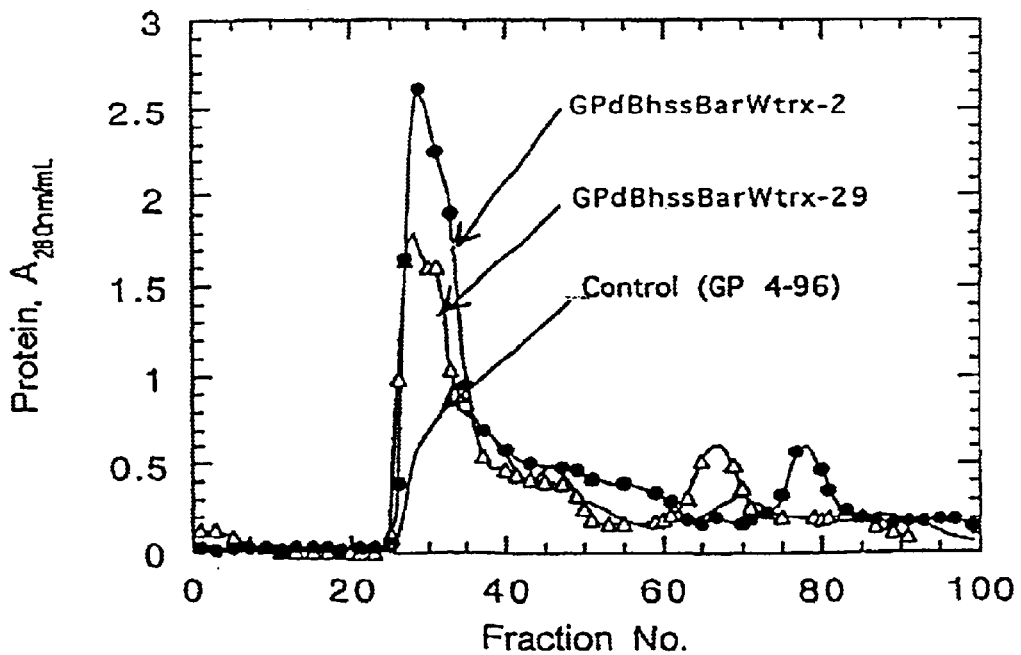
Figure 2

Western Blot Analysis of Barley Grain Transformed with Wheat Thioredoxin

SDS-PAGE: cv. Golden Promise

1. Wheat germ thioredoxin
2. Control (GP 4-96), nontransformed
3. Control, null segregant (GPdBssBarWtrx-29-11-10)
4. Transformed, heterozygous line (GPdBssBarWtrx-29)
5. Transformed, homozygous line 1 (GPdBssBarWtrx-29-3)
6. Transformed, homozygous line 2 (GPdBssBarWtrx-29-3-2)
7. Prestained standards

```
AAGCTTTAACAACCCACACATTGATTGCAACTTAGTCCTACACAAGTTTTCCATT
CTTGTTTCAGGCTAACAACCTATACAAGGTTCCAAAATCATGCAAAAGTGATGC
TAGGTTGATAATGTGTGACATGTAAAGTGAATAAGGTGAGTCATGCATACCAAA
CCTCGGGATTTCTATACTTTGTGTATGATCATATGCACAACTAAAGGCAACTTT
GATTATCAATTGAAAAGTACCGCTTGTAGCTTGTGCAACCTAACACAATGTCCA
AAAATCCATTTGCAAAAGCATCCAAACACAATTGTTAAAGCTGTTCAAACAAAC
AAAGAAGAGATGAAGCCTGGCTACTATAAATAGGCAGGTAGTATAGAGATCTA
CACAAGCACAAGCATCAAAACCAAGAAACACTAGTTAACACCAATCCACTATGA
AGACCTTCCTCATCTTTGCACTCCTCGCCATTGCGGCAACAAGTACGATTGCA
```

FIGURE 6

```
CTTCGAGTGCCCGCCGATTTGCCAGCAATGGCTAACAGACACATATTCTGCC
AAAACCCCAGAACAATAATCACTTCTCGTAGATGAAGAGAACAGACCAAGAT
ACAAACGTCCACGCTTCAGCAAACAGTACCCCAGAACTAGGATTAAGCCGAT
TACGCGGCTTTAGCAGACCGTCCAAAAAAACTGTTTTGCAAAGCTCCAATTCC
TCCTTGCTTATCCAATTTCTTTTGTGTTGGCAAACTGCACTTGTCCAACCGATT
TTGTTCTTCCCGTGTTTCTTCTTAGGCTAACTAACACAGCCGTGCACATAGCC
ATGGTCCGGAATCTTCACCTCGTCCCTATAAAGCCCAGCCAATCTCCACAAT
CTCATCATCACCGAGAACACCGAGAACCACAAAACTAGAGATCAATTCATTG
ACAGTCCACCGAGATGGCTAAGCGGCTGGTCCTCTTTGTGGCGGTAATCGTC
GCCCTCGTGGCTCTCACCACCGCT
```

FIGURE 7

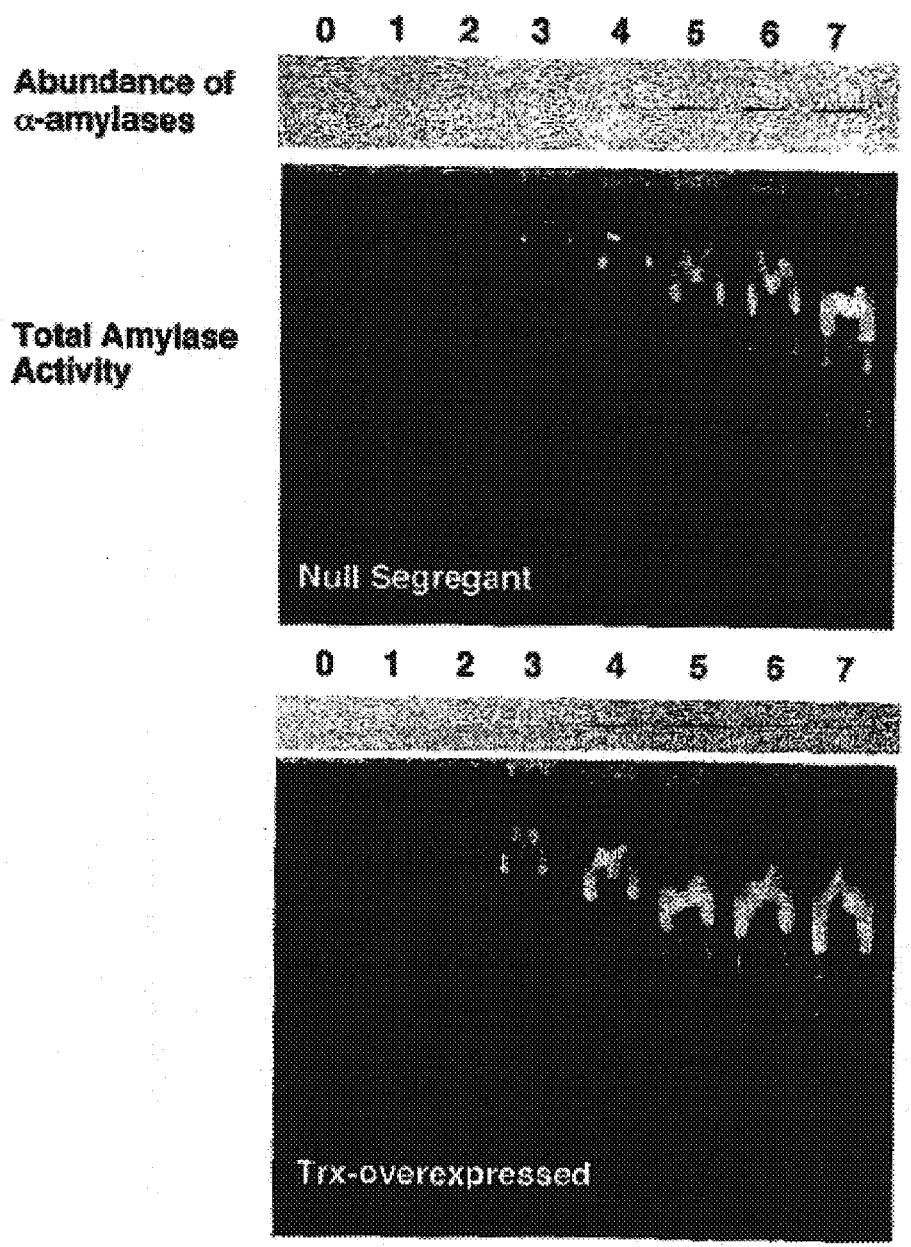

FIGURE 20

| | | | | | | | | | | | | | | | | |
|---|---|---|---|---|---|---|---|---|---|---|---|---|---|---|---|---|
| atg | gcg | gcg | tcg | gca | acg | gcg | gcg | gca | gtg | gcg | gcg | gag | gtg | atc | tcg | 48 |
| Met | Ala | Ala | Ser | Ala | Thr | Ala | Ala | Ala | Val | Ala | Ala | Glu | Val | Ile | Ser | |
| 1 | | | | 5 | | | | | 10 | | | | | 15 | | |
| gtc | cac | agc | ctg | gag | cag | tgg | acc | atg | cag | atc | gag | gag | gcc | aac | acc | 96 |
| Val | His | Ser | Leu | Glu | Gln | Trp | Thr | Met | Gln | Ile | Glu | Glu | Ala | Asn | Thr | |
| | | | 20 | | | | | 25 | | | | | 30 | | | |
| gcc | aag | aag | ctg | gtg | gtg | att | gac | ttc | act | gca | tca | tgg | tgc | gga | cca | 144 |
| Ala | Lys | Lys | Leu | Val | Val | Ile | Asp | Phe | Thr | Ala | Ser | Trp | Cys | Gly | Pro | |
| | | 35 | | | | | 40 | | | | | 45 | | | | |
| tgc | cgc | atc | atg | gct | cca | gtt | ttc | gct | gat | ctc | gcc | aag | aag | ttc | cca | 192 |
| Cys | Arg | Ile | Met | Ala | Pro | Val | Phe | Ala | Asp | Leu | Ala | Lys | Lys | Phe | Pro | |
| | 50 | | | | 55 | | | | | 60 | | | | | | |
| aat | gct | gtt | ttc | ctc | aag | gtc | gac | gtg | gat | gaa | ctg | aag | ccc | att | gct | 240 |
| Asn | Ala | Val | Phe | Leu | Lys | Val | Asp | Val | Asp | Glu | Leu | Lys | Pro | Ile | Ala | |
| 65 | | | | 70 | | | | | 75 | | | | | 80 | | |
| gag | caa | ttc | agt | gtc | gag | gcc | atg | cca | acg | ttc | ctg | ttc | atg | aag | gaa | 288 |
| Glu | Gln | Phe | Ser | Val | Glu | Ala | Met | Pro | Thr | Phe | Leu | Phe | Met | Lys | Glu | |
| | | | | 85 | | | | | 90 | | | | | 95 | | |
| gga | gac | gtc | aag | gac | agg | gtt | gtc | gga | gct | atc | aag | gag | gaa | ctg | acc | 336 |
| Gly | Asp | Val | Lys | Asp | Arg | Val | Val | Gly | Ala | Ile | Lys | Glu | Glu | Leu | Thr | |
| | | | 100 | | | | | 105 | | | | | 110 | | | |
| gcc | aag | gtt | ggg | ctt | cac | gcg | gcg | gcc | cag | taa | | | | | | 369 |
| Ala | Lys | Val | Gly | Leu | His | Ala | Ala | Ala | Gln | | | | | | | |
| | | 115 | | | | 120 | | | | | | | | | | |

VALUE-ADDED TRAITS IN GRAIN AND SEED TRANSFORMED WITH THIOREDOXIN

This application claims the benefit of the filing date of application Ser. No. 60/126,736, filed Mar. 29, 1999, application Ser. No. 60/127,198, filed Mar. 31, 1999, application Ser. No. 60/169,162, filed Dec. 6, 1999, application Ser. No. 60/177,740 filed Jan. 21, 2000, and application Ser. No. 60/177,739, filed Jan. 21, 2000, all of which are expressly incorporated by reference in their entirety.

ACKNOWLEDGMENT OF GOVERNMENT SUPPORT

This invention was made with Government support under Grant 9803835 from the U.S. Department of Agriculture. The Government has certain rights to this invention.

BACKGROUND OF THE INVENTION

Thioredoxins are small (about 12 kDa) thermostable proteins with catalytically active disulfide groups. This class of proteins has been found in virtually all organisms, and has been implicated in myriad biochemical pathways (Buchanan et al., 1994). The active site of thioredoxin has two redox-active cysteine residues in a highly conserved amino acid sequence; when oxidized, these cysteines form a disulfide bridge (—S—S—) that can be reduced to the sulfhydryl (—SH) level through a variety of specific reactions. In physiological systems, this reduction may be accomplished by reduced ferredoxin, NADPH, or other associated thioredoxin-reducing agents. The reduced form of thioredoxin is an excellent catalyst for the reduction of even the most intractable disulfide bonds.

Generally only one kind of thioredoxin is found in bacterial or animal cells. In contrast, photosynthetic organisms have three distinct types of thioredoxin. Chloroplasts contain a ferredoxin/thioredoxin system comprised of ferredoxin, ferredoxin-thioredoxin reductase and thioredoxins f and m, which function in the light regulation of photosynthetic enzymes (Buchanan, 1991; Scheibe, 1991). The other thioredoxin enzyme system is analogous to that established for animals and most microorganisms, in which thioredoxin (h-type in plants) is reduced by NADPH and NADPH-thioredoxin reductase (NTR) (Johnson et al., 1987a: Florencio et al., 1988; Suske et al., 1979). The reduction of thioredoxin h by this system can be illustrated by the following equation:

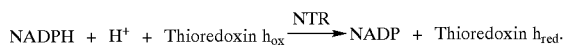

$$NADPH + H^+ + Thioredoxin\ h_{ox} \xrightarrow{NTR} NADP + Thioredoxin\ h_{red}.$$

Thioredoxin is a component of two types of enzyme systems in plants. Chloroplasts contain a ferredoxin/thioredoxin system comprised of ferredoxin, ferredoxin-thioredoxin reductase and thioredoxins f and m, that are involved in the light regulation of photosynthetic enzymes (Buchanan, 1991; Scheibe, 1991). The other enzyme system, the NADP-thioredoxin system or NTS, is analogous to the system established for animals and most microorganisms, in which thioredoxin (h-type in plants) is reduced by NADPH and NADPH-thioredoxin reductase (NTR) (Johnson et al., 1987a; Florencio et al., 1988; Suske et al., 1979). Thioredoxin h is widely distributed in plant tissues and exists in mitochondria, endoplasmic reticulum (ER) and cytosol (Bodenstein-Lang et al., 1989; Marcus et al., 1991).

Plant thioredoxin h is involved in a wide variety of biological functions. The presence of multiple forms of thioredexoin h protein has also been reported in plant seeds (Bestermann et al., 1983). In wheat, three different thioredoxin have been characterized (Vogt and Follman, 1986). Thioredoxin h functions in the reduction of intramolecular disulfide bridges of a variety of low molecular-weight, cystine-rich proteins, including thionins (Johnson et al., 1987b), protease inhibitors and chloroform/methanol-soluble proteins (CM proteins or alpha-amylase inhibitors) (Kobrehel et al., 1991). It is likely that cytoplasmic thioredoxins participate in developmental processes: for example thioredoxin h has been shown to function as a signal to enhance metabolic processes during germination and seedling development (Kobrehel et al., 1992; Lozano et al., 1996; Besse et al., 1996): Thioredoxin h has also been demonstrated to be involved in self-incompatibility in *Phalaris coerulescens* (Li et al., 1995) and *Brassica napus* (Bower et al., 1996). Several functions have been hypothesized for rice thioredoxin h, which is believed to be involved in translocation in sieve tubes (Ishiwatari et al., 1995).

The NTS has been shown to improve dough quality. The improvement in dough strength and bread quality properties of poor-quality wheat flour resulting from the addition of thioredoxin (Wong et al., 1993; Kobrehel et al., 1994) may be attributable to the thioredoxin-catalyzed reduction of intramolecular disulfide bonds in the flour proteins, specifically the glutenins, resulting in the formation of new intermolecular disulfide bonds (Besse and Buchanan, 1997). Thus, the addition of exogenous thioredoxin promotes the formation of a protein network that produces flour with enhanced baking quality. Kobrehel et al., (1994) have observed that the addition of thioredoxin h to flour of non-glutenous cereals such as rice, maize and sorghum promotes the formation of a dough-like product. Hence, the addition of exogenous thioredoxin may be used to produce baking dough from non-glutenous cereals.

In addition, it has been shown that reduction of disulfide protein allergens in wheat and milk by thioredoxin decreases their allergenicity (Buchanan et al., 1997; del Val et al., 1999). Thioredoxin treatment also increases the digestibility of the major allergen of milk (β-lactoglobulin) (del Val et al., 1999), as well as other disulfide proteins (Lozano et al., 1994; Jiao et al., 1992). Therefore, the manipulation of the NTS offers considerable promise for production of nutraceutical and pharmaceutical products. A more detailed discussion of the benefits of adding exogenous thioredoxin to food products is presented in U.S. Pat. No. 5,792,506 to Buchanan et at.

cDNA clones encoding thioredoxin h have been isolated from a number of plant species, including *Arabidopsis thaliana* (Rivera-Madrid et al., 1993; Rivera-Madrid et al., 1995), *Nicotiana tabacum* (Marty and Meyer, 1991; Brugidou et al., 1993), *Oryza sativa* (Ishiwatari et al., 1995), *Brassica napus* (Bower et al., 1996), *Glycine max* (Shi and Bhattacharyya, 1996), and *Triticum aestivum* (Gautier et al., 1998). More recently, two cDNA clones encoding wheat thioredoxin h have been isolated and characterized (Gautier et al., 1998). The *Escherichia coli* NTR gene has been first isolated (Russel and Model, 1988) and the three-dimensional structure of the protein has been analyzed (Kuriyan et al., 1991). Some other NTR genes have been isolated and sequenced from bacteria, fungi and mammals. Recently, Jacquot et al., (1994) have reported a successful isolation and sequencing of two cDNAs encoding the plant *A. thaliana* NTRs. The subsequent expression of the recombinant *A. thaliana* NTR protein in *E. coli* cells (Jacquot et al., 1994) and its first eukaryotic structure (Dai et al., 1996) have also been reported.

Here we disclose value-added traits in transgenic grains, such as barley (Cho et al., 1999b)., wheat, and sorghum, overexpressing thioredoxin

BRIEF DESCRIPTION OF THE DRAWINGS

FIG. 2 shows the thioredoxin activity profile of various barley grains transformed with wheat thioredoxin gene (wtrxh).

FIG. 6 shows the nucleic acid sequence of the B1-hordein promoter and the 57 base pair B1-hordein signal sequence (underlined)(SEQ ID NO: 1).

FIG. 7 shows the nucleic acid sequence of the D-hordein promoter and the 63 base pair D-hordein signal sequence (underlined)(SEQ ID NO: 3).

FIGS. 9A–D shows the change in the activity and abundance of amylases in transgenic and null segregant barley grains during germination and seedling development based on an activity gel. Panel A: abundance of alpha-amylases in null segregant based on western blot. Panel B: Total amylase activity in null segregant Panel C: abundance of alpha-amylases in thioredoxin overexpressing grains. Panel D: total amylase activity in thioredoxin overexpressed grains.

FIG. 20 shows the barley thioredoxin h nucleotide and amino acid sequence (SEQ ID NO:24, SEQ ID NO:25, respectively).

SEQUENCE LISTING

Figure 1:
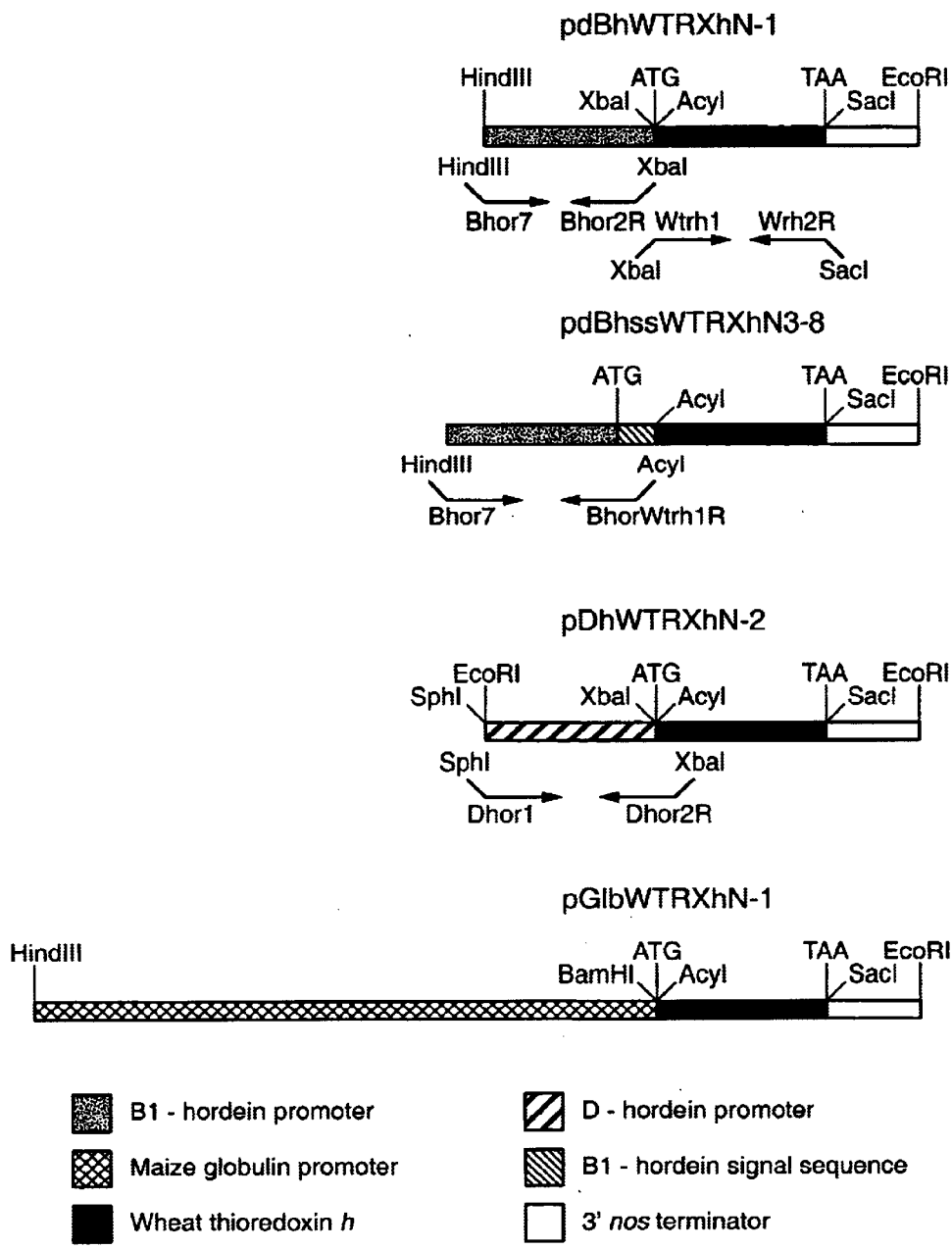
FIG. 1 shows the thioredoxin h constructs used for transformation.

The nucleic and amino acid sequences listed in the accompanying sequence listing are shown using standard letter abbreviations for nucleotide bases, and three letter code for amino acids. Only one strand of each nucleic acid sequence is shown, but it is understood that the complementary strand is included by any reference to the displayed strand. SEQ ID NO:1 shows the nucleic acid sequence of the barley B1-hordein promoter and signal sequence. SEQ ID NO:2 shows the amino acid sequence of the barley B1-hordein signal sequence. SEQ ID NO:3 shows the nucleic acid sequence of the barley D-hordein promoter and signal sequence. SEQ ID NO:4 shows the ammo acid sequence of the barley D-hordein signal sequence. Other sequences are identified below.

SUMMARY OF THE INVENTION

The present invention provides recombinant nucleic acids encoding thioredoxin and methods of use to produce transgenic plants overexpressing thioredoxin. Indeed, given the powerful reducing activity of thioredoxin, over-expression of this protein in a plant cell would be anticipated to have a serious detrimental effect on the cell. However, the inventors have discovered that thioredoxin can be expressed at a high level in plants, particularly cereal grains, without affecting the viability of the cells in which the protein is expressed, or the seeds themselves. By way of example, in certain embodiments the inventors have introduced a wheat thioredoxin gene (wtrxh) into wheat. Seeds of the transgenic-wheat plants can show an increase thioredoxin specific activity in comparison to non-transgenic-wheat plants.

The invention thus provides transgenic plants, wherein at least a part of a plant has an elevated level of thioredoxin protein and/or thioredoxin specific activity compared to the homologous part of non-transgenic plants of the same species. The level of thioredoxin specific activity in the parts of the transgenic plants may be at least about two times greater than the parts of non-transgenic plants of that species. While the invention is applicable to any plant species, it will be particularly beneficial as applied to the monocotyledons, for example cereal crops including, but not limited to rice, barley, wheat, oat, maize, rye, sorghum, millet, and triticale and the dicotyledons including, but not limited to soybeans, lima beans, tomato, potato, soybean, cotton, tobacco. In a preferred embodiment, thioredoxin specific activity is increased in the seeds of the transgenic plant.

Thioredoxin over-expression in a desired part of a plant, for example, a seed, is achieved by use of a seed-specific promoter operably linked to the thioredoxin coding sequence. In this example, "seed-specific" indicates that the promoter has enhanced activity in seeds compared to other plant tissues; it does not require that the promoter is solely active in the seeds. However, given the nature of the thioredoxin protein, it may be advantageous to select a seed-specific promoter that in some cases causes little or no protein expression in tissues other than seeds. In certain embodiments, the seed-specific promoter that is selected is a seed maturation-specific promoter. The use of promoters that confer enhanced expression during seed maturation (such as the barley hordein promoters) may result in even higher levels of thioredoxin expression in the maturing seed.

In an alternative embodiment, thioredoxin is overexpressed in the root, stem, tuber, fruit, leaf, flower, pollen etc or any one or more parts of a plant at the discretion of the practitioner.

In one embodiment of the invention, the provided transgenic plants comprise a recombinant nucleic acid molecule having a structure: P-T, wherein P is a seed-specific promoter, and T is an nucleic acid molecule encoding a thioredoxin polypeptide. In particular embodiments, the seed-specific promoter is a barley hordein gene promoter, such as a barley B1-hordein promoter, a barley D-hordein promoter or a maize embryo specific globulin promoter.

In another embodiment of the invention, the transgenic plants comprise a recombinant nucleic acid molecule having a structure: P-SS-T, wherein P is a seed-specific promoter, T is an nucleic acid molecule encoding a thioredoxin polypeptide and SS is a nucleic acid molecule that encodes a signal peptide that targets expression of the thioredoxin polypeptide to an intracellular body, and wherein P, SS and T are operably linked. Evidence presented herein indicates that the presence of the signal peptide can further enhance the level of thioredoxin expression in the transgenic plants. Suitable signal peptides include, but are not limited to, barley B1- and D-hordein signal peptides.

Parts of the transgenic plants overexpressing thioredoxin as provided by the invention may be harvested for direct processing into food products. For example, the seeds may be ground using conventional means to produce flour. Alternatively, the seeds or other plant parts may be used as a source of thioredoxin, which can be extracted from the immature or mature transgenic plant by standard protein extraction methods. Alternatively, crudely processed seed material may be used directly as a source of thioredoxin. Thus, another aspect of the invention is a method of producing thioredoxin protein, the method comprising harvesting thioredoxin from the seed of a transgenic plant having an elevated level of thioredoxin in its seeds.

Accordingly, in another aspect the invention provides an improved edible products for human and animal consumption, for example increased digestibility and/or reduced allergenicity and dough having increased strength and volume in comparison to dough produced from non-transgenic plant of the same species.

In yet another aspect, the invention provides of methods of making a transgenic plant having reduced allergenicity, increased digestibility, increased redox state (increased SH:SS ratio), in comparison to a non-transgenic plant of the same species.

In still yet another aspect, the invention provide a transgenic plant comprising a nucleic acid encoding *A. thaliana* NTR.

These and other aspects of the invention are further illustrated by the following description and Examples.

DETAILED DESCRIPTION OF THE INVENTION

I. Definitions

Unless otherwise noted, technical terms are used according to conventional usage. Definitions of common terms in molecular biology may be found in Lewin, Genes V published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology, a Comprehensive Desk Reference, published by VCH Publishers, Inc., 1995 (ISBN 1-56081-569-8); Ausubel et al. (1987) Current Protocols in Molecular Biology, Green Publishing; Sambrook et al. (1989) Molecular Cloning: A Laboratory Manual, Cold Spring Harbor, N.Y.

In order to facilitate review of the various embodiments of the invention, the following definitions are provided:

Thioredoxin protein or Thioredoxin polypeptide: A large number of plant, animal, and microbial thioredoxin proteins or polypeptides have been characterized, and the genes encoding many of these proteins have been cloned and sequenced. The present invention is preferably directed to the use of thioredoxin h proteins, although other thioredoxin proteins may also be employed to produce transgenic plants as described herein. Among the thioredoxin h proteins from plants that have been described to date are thioredoxin h proteins from *Arabidopsis thaliana* (Rivera-Madrid et al., 1993; Rivera-Madrid et al., 1995), *Nicotiana tabacum* (Marty and Meyer, 1991; Brugidou et al., 1993), *Oryza sativa* (Ishiwatari et al., 1995), *Brassica napus* (Bower et al., 1996), *Glycine max* (Shi and Bhattacharyya, 1996), and *Triticum aestivum* (Gautier et al., 1998). The amino acid sequences of these and other thioredoxin h proteins, and the nucleotide sequence of cDNAs and/or genes that encode these proteins, are available in the scientific literature and publicly accessible sequence databases. For example, a cDNA encoding thioredoxin h from *Picea mariana* is described in accession number AF051206 (NID g2982246) of GenBank, and located by a search using the Entrez browser/nucleotide sequence search of the National Center for Biotechnology Information website. The cDNA encoding the *Triticum aestivum* thioredoxin h protein used in the Examples described below is described on the same database under accession number X69915 (NID g2995377).

The present invention may be practiced using nucleic acid sequences that encode full length thioredoxin h proteins, as well as thioredoxin h derived proteins that retain thioredoxin h activity. Thioredoxin b derived proteins which retain thioredoxin biological activity include fragments of thioredoxin h, generated either by chemical (e.g. enzymatic) digestion or genetic engineering means; chemically functionalized protein molecules obtained starting with the exemplified protein or nucleic acid sequences, and protein sequence variants, for example allelic variants and mutational variants, such as those produced by in vitro mutagenesis techniques, such as gene shuffling (Stemmer et al., 1994a, 1994b). Thus, the term "thioredoxin h protein" encompasses full length thioredoxin h proteins, as well as such thioredoxin h derived proteins that retain thioredoxin h activity.

Thioredoxin protein may be quantified in biological samples (such as seeds) either in terms of protein level, or in terms of thioredoxin activity. Thioredoxin protein level may be determined using a western blot analysis followed by quantitative scanning of the image as described in detail below. Thioredoxin activity may be quantified using a number of different methods known in the art. Preferred methods of measuring thioredoxin biological activity attributable to thioredoxin h in plant extracts include NADP/malate dehydrogenase activation (Johnson et al., 1987a,b) and reduction of 2',5'-dithiobis(2-nitrobenzoic acid) (DTNB) via NADP-thioredoxin reductase (Florencio et al., 1988; U.S. Pat. No. 5,792,506). Due to the potential for interference from non-thioredoxin h enzymes that use NADPH, accurate determination of thioredoxin h activity should preferably be made using partially purified plant extracts. Standard protein purification methods (e.g. $(NH_4)_2SO_4$ extraction or heat) can be used to accomplish this partial purification. The activity of thioredoxin h may also be expressed in terms of specific activity, i.e., thioredoxin activity per unit of protein present, as described in more detail below.

In another embodiment, thioredoxin may be expressed in ternns of thioredoxin content, such as, mass/mass tissue (i.e., µg/gram tissue) or mass/mass soluble protein (i.e., µg/mg soluble protein)

Promoter: A regulatory nucleic acid sequence, typically located upstream (5') of a gene that, in conjunction with various cellular proteins, is responsible for regulating the expression of the gene. Promoters may regulate gene expression in a number of ways. For example, the expression may be tissue-specific, meaning that the gene is expressed at enhanced levels in certain tissues, or developmentally regulated, such that the gene is expressed at enhanced levels at certain times during development or both.

In a preferred embodiment, a transgenic of the invention is expressed in an edible part of a plant By "edible" herein is meant at least a part of a plant that is suitable for consumption by humans or animals (fish, crustaceans, isopods, decapods, monkeys, cows, goats, pigs, rabbits, horses, birds (chickens, parrots etc.). Accordingly, "edible" embraces food for human consumption and feed for animal consumption and includes, for example, dough, bread, cookies, pasta, pastry, beverages, beer, food additives, thickeners, malt, extracts made from an edible part of plants, animals feeds, and the like. An edible part of a plant includes for example, a root, a tuber, a seed, grain, a flower, fruit, leaf etc. The skilled artisan is aware that expression of the transgene is effected in any tissue, organ or part of a plant by employing a promoter that is active in the selected part of the plant the transgene is to be expressed. In a preferred embodiment the transgene is expressed in a seed, preferably under control of a seed- or grain-specific promoter.

The expression of a transgene in seeds or grains according to the present invention is preferably accomplished by operably linking a seed-specific or grain-specific promoter to the nucleic acid molecule encoding the transgene protein. In this context, "seed-specific" indicates that the promoter has enhanced activity in seeds compared to other plant tissues; it does not require that the promoter is solely active in the seeds. Accordingly, "grain-specific" indicates that the promoter has enhanced activity in grains compared to other plant tissues; it does not require that the promoter is solely active in the grain. Preferably, the seed- or grain-specific promoter selected will, at the time when the promoter is most active in seeds, produce expression of a protein in the seed of a plant that is at least about two-fold greater than expression of the protein produced by that same promoter in the leaves or roots of the plant. However, given the nature of the thioredoxin protein, it may be advantageous to select a seed- or grain-specific promoter that causes little or no protein expression in tissues other than seed or grain. In a preferred embodiment, a promoter is specific for seed and grain expression, such that, expression in the seed and grain is enhanced as compared to other plant tissues but does not require that the promoter be solely activity in the grain and seed. In a preferred embodiment, the promoter is "specific" for a structure or element of a seed or grain, such as an embryo-specific promoter. In accordance with the definitions provided above, an embryo-specific promoter has enhanced activity in an embryo as compared to other parts of a seed or grain or a plant and does not require its activity to be limited to an embryo. In a preferred embodiment, the promoter is "maturation-specific" and accordingly has enhanced activity developmentally during the maturation of a part of a plant as compared to other parts of a plant and does not require its activity to be limited to the development of a part of a plant.

A seed- or grain-specific promoter may produce expression in various tissues of the seed, including the endosperm, embryo, and aleurone or grain. Any seed or grain-specific promoter may be used for this purpose, although it will be advantageous to select a seed- or grain-specific promoter that produces high level expression of the protein in the plant seed or grain. Known seed or grain-specific promoters include those associated with genes that encode plant seed storage proteins such as genes encoding: barley hordeins, rice glutelins, oryzins, or prolamines; wheat gliadins or glutenins; maize zeins or glutelins; maize embryo-specific promoter; oat glutelins; sorghum kafirins; millet pennisetins; or rye secalins.

The barley hordein promoters (described in more detail below) are seed- or grain-specific promoters that were used in the illustrative Examples.

In certain embodiments, the seed- or grain-specific promoter that is selected is a maturation-specific promoter. The use of promoters that confer enhanced expression during seed or grain maturation (such as the barley hordein promoters) may result in even higher levels of thioredoxin expression in the seed.

By "seed or grain-maturation" herein refers to the period starting with fertilization in which metabolizable food reserves (e.g., proteins, lipids, starch, etc.) are deposited in the developing seed, particularly in storage organs of the seed, including the endosperm, testa, aleurone layer, embryo, and scutellar epithelium, resulting in enlargement and filling of the seed and ending with seed desiccation.

Members of the grass family, which include the cereal grains, produce dry, one-seeded fruits. This type of fruit, is strictly speaking, a caryopsis but is commonly called a kernel or grain. The caryopsis of a fruit coat or pericarp, which surrounds the seed and adhere tightly to a seed coat. The seed consists of an embryo or germ and an endosperm enclosed by a nucellar epidermis and a seed coat. Accordingly the grain comprises the seed and its coat or pericarp. The seed comprises the embryo and the endosperm. (R. Carl Hoseney in "Principles of Cereal Science and Technology", expressly incorporated by reference in its entirety).

Hordein promoter: A barley promoter that directs transcription of a hordein gene in barley seeds or grains A number of barley hordein genes and associated promoters have been described and characterized, including those for the B-, C-, D-, and Gamma-hordeins (Brandt et al., 1985; Forde et al., 1985; Rasmussen and Brandt, 1986, Sørensen et al., 1996). The activities of these promoters in transient expression assays have also been characterized (Entwistle et al., 1991; Muller and Knudesen, 1993; Sørensen et al., 1996). While any hordein promoter may be employed for this invention, the specific Examples provided describe the use of the promoter sequences from the $B_1$- and D-hordein genes of barley. The nucleic acid sequences of the barley $B_1$- and D-hordein genes are shown in SEQ ID NOs:1 and 3, respectively and in FIGS. 6 and 7 (the promoter region excludes those nucleotides that encode the hordein signal peptide that is shown underlined). Sørensen et al., (1996) describes plasmids that comprise the $B_1$- and D-hordein promoters operably linked to a beta-glucuronidase gene (uldA; gus) and the *Agrobacterium tumefaciens* nopaline synthase 3' polyadenylation site (nos). These plasmids may be conveniently utilized as sources of both the hordein promoters and the nos polyadenylation site.

One of skill in the art will appreciate that the length of the hordein promoter region may also be greater or less than the sequences depicted in FIGS. 6 and 7. For example, additional 5' sequence from the hordein gene upstream region may be added to the promoter sequence, or bases may be removed from the depicted sequences. However, any hordein promoter sequence must be able to direct transcription of an operably linked sequence in plant seed or grain. The ability of a barley hordein promoter to direct transcription of a protein in a plant seed may readily be assessed by operably linking the promoter sequence to an open reading frame (ORF) that encodes a readily detectable protein, such as the gus ORF, introducing the resulting construct into plants and then assessing expression of the protein in seeds of the plant (see Sørensen et al., 1996). A hordein promoter will typically confer seed-specific expression, meaning that expression of the protein encoded by the operably linked ORF will generally be at least about twice as high (assessed on an activity basis) in seeds of the stably transfected plant compared to other tissues such as leaves. More usually, the hordein promoter will produce expression in seeds that is at least about 5 times higher than expression in other tissues of the plant.

Functional homologs of the barley hordein promoters disclosed herein may be obtained from other plant species, such as from other monocots, including wheat, rice and corn. Such homologs may have specified levels of sequence identity with the prototype hordein promoters (e.g., at least 40% sequence identity). The functional homologs retain hordein promoter function, i.e., retain the ability to confer seed or grain-specific expression on operably linked ORFs when introduced into plants (Marris et al., 1988; Mena et al., 1998). Accordingly, where reference is made herein to a hordein promoter, it will be understood that such reference includes not only nucleic acid molecules having the sequences of the prototypical sequences disclosed herein (or variations on these sequences), but also promoters from hordein gene homologs. Also included within the scope of such terms are molecules that differ from the disclosed prototypical molecules by minor variations. Such variant sequences may be produced by manipulating the nucleotide sequence of hordein promoter using standard procedures such as site-directed mutagenesis or the polymerase chain reaction. Preferably, the seed- or grain-specificity of the promoter is retained. Examples of dicot promoters that can be used include for example soybean glycinins and con-glycinins, and kidney bean phaseolin promoters.

Signal peptide: As described in the Examples below, the inventors have discovered that the level of expression of thioredoxin in seed or grain can be enhanced by the presence of a signal peptide. In one of the Examples described below, the B1 hordein signal peptide was utilized. In particular, it was discovered that the expression of thioredoxin protein in seed or grain is enhanced when the ORF encoding the protein is operably linked to both a hordein promoter and a hordein signal sequence encoding the signal peptide. (For convenience, the nucleic acid sequence encoding a signal peptide; is referred to herein as a signal sequence.) While not wishing to be bound by theory, it is proposed that the hordein signal peptide directs expression of the thioredoxin protein to a protected subcellular location, such as a vacuole or protein body. It is further proposed that proteins directed to such vacuoles are protected from proteolysis during certain stages of seed or grain maturation. In addition, the sequestration of the thioredoxin protein to such a location may also serve to protect the maturing seeds or grain from detrimental effects associated with thioredoxin over-expression.

The hordein signal peptide typically comprises about the first 15–25 amino acids of the hordein gene ORF, more usually about 18–21 amino acids. The nucleotide and amino acid sequences of the hordein signal sequence and peptide of the prototypical barley B1- and D-hordein genes are shown in SEQ ID NOS: 1–4 and FIGS. 6 and 7. One of skill in the art will appreciate that while the B1-hordein signal sequence and signal peptide are utilized in the examples described below, the invention is not limited to these specific sequences. For example, homologous sequences may be used as effectively, as may sequences that differ in exact nucleotide or amino acid sequences, provided that such sequences result in enhanced levels of the encoded protein in immature seed or grain. Typically, "enhanced expression" will be expression that is about twice that observed with an equivalent construct lacking the signal sequence. Accordingly, the term "hordein signal sequence" and "hordein signal peptide" includes not only the particular sequences shown herein, but also homologs and variants of these sequences.

Furthermore, the invention is not limited to the use of hordein signal peptides. Other signal peptides that serve to localize the thioredoxin co-translationally or posttranslationally to a selected seed, grain or cell compartment may be employed. Other such signal sequences include those associated with storage proteins in maize, rice, wheat, soybeans, beans, and tobacco (see for example: Bagga et al., 1997; Torrent et al., 1997; Wu et al., 1998; Zheng et al., 1995; Grimwade et al., 1996; Conrad et al., 1998; and Takaiwa et al., 1995.)

Starch: A polysaocharide made up of a chain of glucose units joined by alpha-1,4 linkages, either unbranched (amylose) or branched (amylopectin) at alpha-1,6-linkages.

Dextran: Any of a variety of storage polysaecharides, usually branched, made of glucose residues joined by alpha-1,6 linkages.

Dextrin or Limit Dextrin: Any of a group of small soluble polysaccharides, partial hydrolysis products of starch, usually enriched in alpha-1,6-linkages.

Germination: A resumption of growth of a plant embryo in favorable conditions after seed maturation and drying (dessication), and emergence of young shoot and root from the seed.

Allergen: An antigenic substance that induces an allergic reaction in a susceptible host. Accordingly, a susceptible host has an immune status (hypersensitivity) that results in an abnormal or harmful immune reaction upon exposure to an allergen. In a preferred embodiment, the transgenic grains of the; invention have reduced allergenicity in comparison to nontransgenic grains. The immune reaction can be immediate or delayed; cell mediated or antibody mediated; or a combination thereof. In a preferred embodiment, the allergic reaction is an immediate type hypersensitivity.

Digestion: By "digestion" herein is meant the conversion of a molecule or compound to one or more of its components. Accordingly, "digestibility" relates to the rate and efficiency at which the conversion to one or more of its components occurs. In a preferred embodiment a "digestible compound" is, for example, a food, that is converted to its chemical components by chemical or enzymatic means. For example, dextran is converted to dextrin, polysaccharide, monosaccharides, limit dextrin etc; a protein is converted to a polypeptides, oligopeptides, amino acids, ammonia etc.; a nucleic acid is converted to oligonucleotides, nucleotides, nucleosides, purine, pyrimidines, phosphates etc. In a preferred embodiment, the transgenic grains of the invention have increased digestibility, i.e. are more efficiently or rapidly digested In comparison to nontransgenic grain.

Sequence identity: The similarity between two nucleic acid sequences, or two amino acid sequences is expressed in terms of sequence identity (or, for proteins, also in terms of sequence similarity). Sequence identity is frequently measured in terms of percentage identity; the higher the percentage, the more similar the two sequences are. As described above, homologs and variants of the thioredoxin nucleic acid molecules, hordein promoters and hordein signal peptides may be used in the present invention. Homologs and variants of the nucleic acid molecules will possess a relatively high degree of sequence identity when aligned using standard methods.

Methods of alignment of sequences for comparison are well known in the art. Various programs and alignment algorithms are described in: Smith and Waterman (1981); Needleman and Wunsch (1970); Pearson and Lipman (1988); Higgins and Sharp (1988); Higgins and Sharp (1989); Corpet et al., (1988); Huang et al., (1992); and Pearson et al., (1994). Altschul et al., (1994) presents a detailed consideration of sequence alignment methods and homology calculations.

The NCBI Basic Local Alignment Search Tool (BLAST) (Altschul et al., 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI website. A description of how to determine sequence identity using this program is also available at the website.

Homologs of the disclosed protein sequences are typically characterized by possession of at least 40% sequence identity counted over the full length alignment with the amino acid sequence of the disclosed sequence using the NCBI Blast 2.0, gapped blastp set to default parameters. The adjustable parameters are preferably set with the following values, overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. Proteins with even greater similarity to the reference sequences will show increasing percentage identities when assessed by this method, such as at least about 50%, at least about 60%, at least about 70%, at least about 75%, at least about 80%, at least about 90% or at least about 95% sequence identity.

Homologs of the disclosed nucleic acid sequences are typically characterized by possession of at least 40% sequence identity counted over the full length alignment with the amino acid sequence of the disclosed sequence using the NCBI Blast 2.0, gapped blastn set to default parameters. A preferred method utilizes the BLASTN module of WU-BLAST-2 (Altschul et al., 1996); set to the default parameters, with overlap span and overlap fraction set to 1 and 0.125, respectively. Nucleic acid sequences with even greater similarity to the reference sequences will show increasing percentage identities when assessed by this method, such as at least about 50%, at least about 60%, at least about 70%, at least about 75%, at least about 80%, at least about 90% or at least about 95% sequence identity.

The alignment may include the introduction of gaps in the sequences to be aligned. In addition, for sequences which contain either more or fewer amino acids than the protein encoded by the sequences in the figures, it is understood that in one embodiment, the percentage of sequence identity will be determined based on the number of Identical amino acids in relation to the total number of amino acids. Thus, for example, sequence identity of sequences shorter than that shown in the figures as discussed below, will be determined using the number of amino acids in the longer sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described herein for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

As will be appreciated by those skilled in the art, the sequences of the present invention may contain sequencing errors. That is, there may be incorrect nucleosides, frameshifts, unknown nucleosides, or other types of sequencing errors in any of the sequences; however, the correct sequences will fall within the homology and stringency definitions herein.

Vector: A nucleic acid molecule as introduced into a host cell, thereby producing a transformed host cell. A vector may include one or more nucleic acid sequences that permit it to replicate in one or more host cells, such as origin(s) of replication. A vector may also include one or more selectable marker genes and other genetic elements known in the art.

Transformed: A transformed cell is a cell into which has been introduced a nucleic acid molecule by molecular biology techniques. As used herein, the term transformation encompasses all techniques by which a nucleic acid molecule might be introduced into such a cell, plant or animal cell, including transfection with viral vectors, transformation by Agrobacterium, with plasmid vectors, and introduction of naked DNA by electroporation, lipofection, and particle gun acceleration and includes transient as well as stable transformants.

isolated: An "isolated" biological component (such as a nucleic acid or protein or organelle) has been substantially separated or purified away from other biological components in the cell or the organism in which the component naturally occurs, i.e., other chromosomal and extra-chromosomal DNA and RNA, proteins and organelles. Nucleic acids and proteins that have been "isolated" Include nucleic acids and proteins purified by standard purification methods. The term embraces nucleic acids including chemically synthesized nucleic acids and also embraces proteins prepared by recombinant expression in vitro or in a host cell and recombinant nucleic acids as defined below.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary, join two protein-coding regions in the same reading frame. With respect to polypeptides, two polypeptide sequences may be operably linked by covalent linkage, such as through peptide bonds or disulfide bonds.

Recombinant: By "recombinant nucleic acid" herein is meant a nucleic acid that has a sequence that is not naturally occurring or has a sequence that is made by an artificial combination of two otherwise separated segments of sequence. This artificial combination is often accomplished by chemical synthesis or, more commonly, by the artificial manipulation of of nucleic acids, e.g., by genetic engineering techniques, such as by the manipulation of at least one nucleic acid by a restriction enzyme, ligase, recombinase, and/or a polymerase. Once introduced into a host cell, a recombinant nucleic acid is replicated by the host cell, however, the recombinant nucleic acid once replicated in the cell remains a recombinant nucleic acid for purposes of this invention. By "recombinant protein" herein is meant a protein produced by a method employing a recombinant nucleic acid. As outlined above "recombinant nucleic acids" and "recombinant proteins" also are "isolated", as described above.

Complementary DNA (cDNA): A piece of DNA that is synthesized in the laboratory by reverse transcription of an RNA, preferably an RNA extracted from cells. cDNA produced from mRNA typically lacks internal, non-coding segments (introns) and regulatory sequences that determine transcription.

Open reading frame (ORF): A series of nucleotide triplets (codons) coding for amino acids without any internal termination codons. These sequences are usually translatable into a peptide.

Transgenic plant: As used herein, this term refers to a plant that contains recombinant genetic material not normally found in plants of this type and which has been introduced into the plant in question (or into progenitors of the plant) by human manipulation. Thus, a plant that is grown from a plant cell into which recombinant DNA is introduced by transformation is a transgenic plant, as are all offspring of that plant that contain the introduced transgene (whether produced sexually or asexually). It is understood that the tern transgenic plant encompasses the entire plant and parts of said plant, for instance grains, seeds, flowers, leaves, roots, fruit, pollen, stems etc.

The present invention is applicable to both dicotyledonous plants (e.g. tomato, potato, soybean, cotton, tobacco, etc.) and monocotyledonous plants, including, but not limited to graminaceous monocots such as wheat (Triticum spp.), rice (Oryza spp.), barley (Hordeum spp.), oat (Avena spp.), rye (Secale spp.), corn (Zea mays), sorghum (Sorghum spp.) and millet (Pennisetum spp). For example, the present invention can be employed with barley genotypes including, but not limited to Morex, Harrington, Crystal, Stander, Moravian III, Galena, Salome, Steptoe, Klages, Baronesse, and with wheat genotypes including, but not limited to Yecora Rojo, Bobwhite, Karl and Anza. In general, the invention is particularly useful in cereals.

Purified: The term purified does not require absolute purity; rather, it is intended as a relative term Thus, for example, a purified barley thioredoxin h protein preparation is one in which the barley thioredoxin h protein is more enriched or more biochemically active or more easily detected than the protein is in its natural environment within a cell or plant tissue. Accordingly, "purified" embraces or includes the removal or inactivation of an inhibitor of a molecule of interest. In a preferred embodiment, a preparation of barley thioredoxin h protein is purified such that the barley thioredoxin h represents at least 5–10% of the total protein content of the preparation. For particular applications, higher protein purity may be desired, such that preparations in which barley thioredoxin h represents at least 50% or at least 75% or at least 90% of the total protein content may be employed.

Ortholog: Two nucleotide or amino acid sequences are orthologs of each other if they share a common ancestral sequence and diverged when a species carrying that ancestral sequence split into two species, sub-species, or cultivars. Orthologous sequences are also homologous sequences.

II. Production of Plants with Elevated Seed Thioredoxin

Standard molecular biology methods and plant transformation techniques can be used to produce transgenic plants that produce seeds having an elevated level of thioredoxin protein. The following sections provide general guidance as to the selection of particular constructs and transformation procedures.

a. Constructs

The present invention utilizes recombinant constructs that are suitable for obtaining elevated expression of thioredoxin in plant seeds relative to non-transformed plant seeds. In their most basic form, these constructs may be represented as P-T, wherein P is a seed-specific promoter and T is a nucleic acid sequence encoding thioredoxin. In another embodiment, a peptide signal sequence that targets expression of the thioredoxin polypeptide to an intracellular body may be employed. Such constructs may be represented as P-SS-T, wherein SS is the signal peptide. Nucleic acid molecules that may be used as the source of each of these components are described in the Definitions section above.

Each component is operably linked to the next For example, where the construct comprises the hordein D-promoter (P), the hordein D-signal sequence (SS) encoding the hordein signal peptide, and an open reading frame encoding, preferably, the wheat thioredoxin h protein M), the hordein promoter is linked to the 5' end of the sequence encoding the hordein signal sequence, and the hordein signal sequence is operably linked to the 5' end of the thioredoxin open reading frame, such that C terminus of the signal peptide is joined to the N-terminus of the encoded protein.

The construct will also typically include a transcriptional termination region following the 3' end of the encoded protein ORF. Illustrative transcriptional termination regions include the nos terminator from Agrobacterium Ti plasmid and the rice alpha-amylase terminator.

Standard molecular biology methods, such as the polymerase chain reaction, restriction enzyme digestion, and/or ligation may be employed to produce these constructs comprising any nucleic acid molecule or sequence encoding a thioredoxin protein or polypeptide.

b. General Principles of Plant Transformation

Introduction of the selected construct into plants is typically achieved using standard transformation techniques. The basic approach is to: (a) clone the construct into a transformation vector; which (b) is then introduced into plant cells by one of a number of techniques (e.g., electroporation, microparticle bombardment, Agrobacterium infection); (c) identify the transformed plant cells; (d) regenerate whole plants from the identified plant cells, and (d) select progeny plants containing the introduced construct.

Preferably all or part of the transformation vector will stably integrate into the genome of the plant cell. That part of the transformation vector which integrates into the plant cell and which contains the Introduced P-T or P-SS-T sequence (the introduced "thioredoxin transgene") may be referred to as the recombinant expression cassette.

Selection of progeny plants containing the introduced transgene may be made based upon the detection of thioredoxin or NTR over-expression in seeds, or upon enhanced resistance to a chemical agent (such as an antibiotic) as a result of the inclusion of a dominant selectable marker gene incorporated into the transformation vector.

Successful examples of the modification of plant characteristics by transformation with cloned nucleic acid sequences are replete in the technical and scientific literature. Selected examples, which serve to illustrate the knowledge in this field of technology include:

U.S. Pat. No. 5,571,706 ("Plant Virus Resistance Gene and Methods");

U.S. Pat. No. 5,677,175 ("Plant Pathogen Induced Proteins");

U.S. Pat. No. 5,510,471 ("Chimeric Gene for the Transformation of Plants");

U.S. Pat. No. 5,750,386 ("Pathogen-Resistant Transgenic Plants");

U.S. Pat. No. 5,597,945 ("Plants Genetically Enhanced for Disease Resistance");

U.S. Pat. No. 5,589,615 ("Process for the Production of Transgenic Plants with Increased Nutritional Value Via the Expression of Modified 2S Storage Albumins");

U.S. Pat. No. 5,750,871 ("Transformation and Foreign Gene Expression In Brassica Species");

U.S. Pat. No. 5,268,526 ("Overexpression of Phytochrome in Transgenic Plants");

U.S. Pat. No. 5,780,708 ("Fertile Transgenic Corn Plants");

U.S. Pat. No. 5,538,880 ("Method For Preparing Fertile Transgenic Corn Plants");

U.S. Pat. No. 5,773,269 ("Fertile Transgenic Oat Plants");

U.S. Pat. No. 5,736,369 ("Method For Producing Transgenic Cereal Plants");

U.S. Pat. No. 5,610,049 ("Methods For Stable Transformation of Wheat").

These examples include descriptions of transformation vector selection, transformation techniques and the construction of constructs designed to express an introduced transgene.

c. Plant Types

The transgene-expressing constructs of the present invention may be usefully expressed in a wide range of higher plants to obtain seed- or grain-specific expression of selected polypeptides. The invention is expected to be particularly applicable to monocotyledonous cereal plants including barley, wheat, rice, rye, maize, triticale, millet, sorghum, oat, forage, and turf grasses. In particular, the transformation methods described herein will enable the invention to be used with genotypes of barley including Morex, Harrington, Crystal, Stander, Moravian III, Galena, Golden Promise, Steptoe, Klages and Baronesse, and commercially important wheat genotypes including Yecora Rojo, Bobwhite, Karl and Anza.

The invention may also be applied to dicotyledenous plants, including, but not limited to, soybean, sugar beet, cotton, beans, rape/canola, alfalfa, flax, sunflower, safflower, brassica, cotton, flax, peanut, clover, vegetables such as lettuce, tomato, cucurbits, cassava, potato, carrot, radish, pea, lentils, cabbage, cauliflower, broccoli, Brussels sprouts, peppers; and tree fruits such as citrus, apples, pears, peaches, apricots, and walnuts.

d. Vector Construction

A number of recombinant vectors suitable for stable transformation of plant cells or for the establishment of transgenic plants have been described including those described in Weissbach and Weissbach, (1989), and Gelvin et al., (1990). Typically, plant transformation vectors include one or more ORFs under the transcriptional control of 5' and 3' regulatory sequences and a dominant selectable marker with 5' and 3' regulatory sequences. The selection of suitable 5' and 3' regulatory sequences for constructs of the present invention is discussed above. Dominant selectable marker genes that allow for the ready selection of transformants include those encoding antibiotic resistance genes (e.g., resistance to hygromycin, kanamycin, bleomycin, G418, streptomycin or spectinomycin) and herbicide resistance genes (e.g, phosphinothricin acetyltransferase).

e. Transformation and Regeneration Techniques

Methods for the transformation and regeneration of both monocotyledonous and dicotyledonous plant cells are known, and the appropriate transformation technique will be determined by the practitioner. The choice of method will vary with the type of plant to be transformed; those skilled in the art will recognize the suitability of particular methods for given plant types. Suitable methods may include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and Agrobacterium mediated transformation. Typical procedures for transforming and regenerating plants are described in the patent documents listed at the beginning of this section.

f. Selection of Transformed Plants

Following transformation, transformants are preferably selected using a dominant selectable marker. Typically, such a marker will confer antibiotic or herbicide resistance on the seedlings of transformed plants, and section of transformants can be accomplished by exposing the seedlings to appropriate concentrations of the antibiotic or herbicide. After transformed plants are selected and grown to maturity to allow seed set, the seeds can be harvested and assayed for over-expression of thioredoxin.

III. Use of Plants, Seeds or Grains Expressing Elevated Levels of Thioredoxin In one embodiment, the transgene protein, for example thioredoxin expressed In plants, especially seeds or grains, using the methods described herein, is used in the production and synthesis of thioredoxin. The thioredoxin transgene expressed by the recombinant nucleic acid of the invention may be harvested at any point after expression of the protein has commenced. When harvesting from the seed or grain or other part of a plant for example, it is not necessary for the seed or grain or other part of the plant to have undergone maturation prior to harvesting. For example, transgene expression may occur prior to seed or grain maturation or may reach optimal levels prior to seed or grain maturation. The transgene protein may be isolated from the seeds or grain, if desired, by conventional protein purification methods. For example, the seed or grain can be milled, then extracted with an aqueous or organic extraction medium, followed by purification of the extracted thioredoxin protein. Alternatively, depending on the nature of the intended use, the transgene protein may be partially purified, or the seed or grain may be used directly without purification of the transgene protein for food processing or other purposes.

For example, the addition of thioredoxin promotes the formation of a protein network that produces flour with enhanced baking quality. Kobrehel et al., (1994) have shown that the addition of thioredoxin to flour of non-glutenous cereal such as rice, maize, and sorghum promotes the formation of a dough-like product. Accordingly, the addition of thioredoxin expressed in seeds using the methods described herein find use in the production of flour with improved baking quality such as increased strength and/or volume.

The enhanced expression of thioredoxin also produces a seed having an altered biochemical composition. For example, enhanced thioredoxin expression produces seed with increased enzymatic activity, such as, increased pullulanase and alpha-amylase A. Enhanced thioredoxin expression also produces seed with early alpha-amylase B activation. Pullulanase ("debranching enzyme") is an enzyme that breaks down branched starch of the endosperm of cereal seeds by hydrolytically cleaving alpha-1,6 bonds. Alpha-amylases break down starch 1–4 linkages. Pullulanase and amylases are enzymes fundamental to the brewing and baking industries. Pullulanase and amylases are required to break down starch in malting and in certain baking procedures carried out in the absence of added sugars or other carbohydrates. Obtaining adequate activity of these enzymes is problematic especially in the malting industry. It has been known for some time that dithiothreitol (DTT, a chemical reductant that reduces and sometimes replaces thioredoxin) activates pullulanase of cereal preparations (e.g., barley, oat, and rice flours). A method of adequately increasing the activity of pullulanase and alpha-amylase A and shortening the activation time of alpha-amylase B with a physiologically acceptable system, leads to more rapid malting methods and, owing to increased sugar availability, to alcoholic beverages such as beers with reduced carbohydrate content.

Accordingly, seeds or grains with enhanced thioredoxin expression provide advantages in the production of malt and beverages produced by a fermentation process. Enhanced pullulanase and alpha-amylase A and earlier induction of alpha-amylase B in grain increases the speed and efficiency of germination, important in malting, where malt is produced having increased enzymatic activity resulting in enhanced hydrolysis of starch to fermentable carbohydrates, thereby, improving the efficiency of fermentation in the production of alcoholic beverages, for example, beer and scotch whiskey. Early alpha-amylase B activation would reduce the total time for malting by about 20%. Enhanced fermentation processes also find use in the production of alcohols that are not intended for human consumption, i.e., industrial alcohols.

In another embodiment, seed or grains with enhanced thioredoxin expression provide advantages in enhancing the onset and efficiency of germination.

The overexpression of thioredoxin in seed or grains results in an increase in the total protein. It also promotes the redistribution of proteins to the most soluble albumin/globulin fraction and the production of flour and other food products, feed, and beverages with improved digestibility in comparison to edible products made from non-transformed grains. Such edible products find use in amelioration and treatment of food malabsorptive syndromes, for example, sprue or catarrhal dysentery. Sprue is a malabsorptive syndrome affecting both children and adults, precipitated by the ingestion of gluten-containing foods. Edible products that are more readily digested and readily absorbed avoid or ameliorate the disease symptoms. Edible products with improved digestibility also ameliorate or reduce symptoms associated with celiac disease in which storage proteins that are not readily digested in afflicated individuals result in inflammation of the GI tract.

The expression of thioredoxin in seed grains results in the production of foods and other edible products with reduced allergenicity in comparison to edible products made from non-transformed grains. Food allergies are a significant health and nutrition problem (Lehrer et al., 1998). Up to 2% of adults and 8% of children have a food allergy causing serious symptoms including death. Wheat protein is one of the principal allergens. Food allergies are defined by the American academy of Allergy and Immunology Committee on Adverse Reactions to Food as "an immunological reaction resulting from the ingestion of a food or a food additive" (Fenema, 1996; Lasztity, 1996). Most true allergic responses to food proteins appear to be caused by a type-I imunolobulin E (IgE)-mediated hypersensitivity reaction (Sicherer, 1999). These responses may occur within minutes or a few hours after eating the offending food (Furlong-Munoz, 1996). When the offending food is injested by allergy-sensitive individuals the body releases histamines and other biochemicals, resulting in itchy eyes, rash or hives; runny nose; swelling of the lips, tongue, and face; itching or tightness of the throat; abdominal pain: nausea; diarrhea; and shortness of breath. Some individuals have severe, anaphylactic reactions, resulting in approximately 135 deaths per year in the United States. In the United States over 2,500 emergency rooms visits per year are allergy-related. There is no cure for food allergies, only avoidance of the food will prevent symptoms. For example, patents with wheat allergy must avoid wheat- or gluten-containing foods; wheat gluten is a very common ingredient in many processed foods (Marx et al.,1999).

A feature common to many allergens is the presence of one or more disulfide bonds that contribute to the resistance of allergens to digestion (Astwood at al., 1996), allowing them to be mostly intact when they react the small intestine where they are presented to mucosal cells that mount an IgE immune response. The major allergens were found to be insoluble storage proteins, gliadins and glutenins. The soluble storage proteins, albumins and globulins were considerably weaker (Buchanan et al., 1997). Allergenicity of these proteins is substantially decreased after thioredoxin treatment and disulfide bond reduction.

Edible products, for example, bread, cookies, dough, thickeners, beverages, malt, pasta, food additives, including animal feeds, made using the transgenic plants or parts of a transgenic plant of the invention have decreased allergenicity and accordingly can be used to in the treatment of an allergic response. By "treatment" or "alleviating" symptoms herein is meant prevention or decreasing the probability of symptoms.

Increased digestibility of seeds or grains also provides wider consumption of grains by man and animals who otherwise can not consume such grains. For example, sorghum is the world's fifth leading grain in terms of metric tons after wheat, rice, maize, and barley and third in production in the Untied States after maize and wheat. The use of sorghum is constrained in part because of the difficulty associated with the digestibility of its protein and starch compared to other grains. This difficulty with the digestibility of sorghum protein and starch has to do with the structure of the seed and the manner in which the proteins are associated with the starch. The digestibility of the starch flour from sorghum cultivars is 15–25% lower in digestibility than, for example, maize. Perhaps more notable is the fact that, unlike other grains, the indigestibility of unprocessed sorghum flour increases dramatically after boiling in water, a common practice in Africa. A study with human subjects showed that protein digestibility in cooked sorghum porridge can be as low as 46%, whereas the percent digestibility for cooked wheat maize, and rice was 81%, 73%, and 66% respectively (Mertz et al. 1984, MacLean et al. 1981). Exogenous addition of reducing agents increases the digestibility of the starch (Hamaker et al. 1987). However, the efficacy of manipulating the thioredoxin system in vivo in the seed by expressing increased amounts of thioredoxin in a manner which does not adversely affect plant development or morphology had not previously been demonstrated. Accordingly, the transgenic plants of the invention provide wider use of seeds or grains as food sources by increasing the digestibility of the starch and/or protein component. The transgenic seeds or grains of the present invention also provide the advantage of increasing the digestibility of food products for human and feed for animals made of these grains without the addition of exogenous reducing agents. In addition, the increased digestibility results in greater utilization of the food or feed, i.e., a human or animal consuming an edible product comprising a transgenic seed or grain of the invention or an extract thereof more efficiently absorbs nutrients and therefore requires to consume less in comparison to a non-transgenic food product. In another embodiment the transgenic seed, grain or extracts thereof of the present invention and extracts or food products thereof are used as a food or feed additives. For example, an extract or flour or malt produced from a transgenic seed or grain of the invention is added to a non transgenic food or feed product to improve the digestibility or decrease the allergenicity of the nontransgenic food product or to improve the quality of the total food product, such as, by increasing the strength and/or volume of the food product.

Illustrative embodiments of the invention are described below,

EXAMPLES

Example 1

Expression of Wheat Thioredoxin h (WTRXh) in Transgenic Barley

Four different DNA constructs were produced, each containing a 384-bp wtrxh fragment encoding the 13.5-KDa WTRXh protein. The four constructs are illustrated in FIG. 1 and described below. Each construct comprised the 384-bp wtrxh fragment operably linked to a seed-specific promoter (either the barley endosperm-specific D-hordein or B1-hordein promoters or the maize embryo-specific globulin promoter). An additional construct comprised the 384-bp wtrxh fragment operably linked to the B1-hordein promoter and the B1-hordein signal sequence (FIG. 6). The transformation vector used included the bar gene, conferring resistance to bialaphos. Twenty-eight independent regenerable barley lines were obtained after bialaphos selection and all were PCR-positive for the bar gene. The presence of the wtrxh gene was confirmed in the genome of the 28 independent lines by PCR and DNA hybridization analyses. The expression of the WTRXh protein was assessed by western blot analysis, using purified wheat thioredoxin as a control. The WTRXh expressed in transgenic barley had a molecular mass that differed from native barley TRXh but was identical to WTRXh. The WTRXh was found to be highly expressed in developing and mature seed of transgenic barley plants although levels of expression varied among the transgenic events. On average, higher expression levels were observed in lines transformed with the DNA construct containing the B1-hordein promoter plus the signal peptide sequence than the same promoter without the signal peptide sequence. The WTRXh purified from transgenic barley seed was confirmed to be biochemically active.

A. Materials and Methods
Plant Materials for Transformation
A two-rowed spring cultivar of barley, Golden Promise, was grown in growth chambers as described previously (Wan and Lemaux 1994; Lemaux et al., 1996).
Construction of Wheat Thioredoxin h Expression Vectors and DNA Sequencing
Expression vectors were constructed containing the wheat thioredoxin h gene (wtrxh) driven by the barley endosperm-specific $B_1$- or D-hordein promoter or the maize embryo-specific globulin promoter. The plasmids were constructed as follows.
(1) pDhWTRXN-2: A 384-bp wtrxh coding region was amplified by PCR from pTaM13.38 (Gautier et al., 1998). This plasmid contained a cDNA of wtrxh, which was used as a template, creating XbaI and SacI sites with the following primers Wtrxh1 (5'-atatctaga<u>ATGGCGGCGTCGGCGGCGA</u>) (SEQ ID NO:5) and Wtrxh2R (5'-atagagctc<u>TTACTGGGCCGCGTGTAG</u>) (SEQ ID NO:6), respectively (FIG. 1). Small letters in the primes denote a restriction enzyme site for subcloning of the DNA fragment containing the wtrxh gene; underlined letters denote wtrxh sequences. The ATG initiation codon for wtrxh expression was included in the Wtrxh1 primer. PCR reactions were performed on a thermocycler (MJ Research Inc., Watertown, Mass.) using recombinant Taq DNA polymerase (Promega. Madison, Wis.) in a 100 μl reaction volume. The reaction buffer contained 10 mM Tris-HCl (pH 9.0), 50 mM KCl, 1.5 mM $MgCl_2$, 0.1% Triton-X-100, and 50 μM of each deoxyribonucleoside triphosphate. PCR conditions utilized 25 cycles of 94° C. for 1 min, 55° C. for 1 min and 72° C. for 2 min, with a final extension step 72° C. for 7 min. The wtrxh fragment, which was amplified with the primers Wtrxh1 and Wtrxh2R, was purified from a 0.7% agarose gel using a QIAquick® gel extraction kit (Qiagen Inc., Chatsworth, Calif.), digested with XbaI and SacI and ligated into XbaI/SacI-digested pUC19 to generate the pWTRXh-1 plasmid. Nucleotide sequences of the PCR-amplified wtrxh coding region fragment were determined by the dideoxynucleotide chain termination method using Sequenase according to manufacturer's instructions (United States Biochemical. Cleveland, Ohio) with double-stranded plasmid templates and regularly spaced primers.

pDhWTRXN-2 was made by replacing the uidA gene in pDhGN-2 (containing barley endosperm-specific D-hordein promoter (FIG. 7) and nos 3' terminator) with the XbaI/SacI fragment containing the wtrxh coding sequence from pWTRXh-1, which contains the PCR-amplified wtrxh coding sequence in pUC19. To construct pDhGN-2, a 0.4-kb D-hordein promoter was amplified by PCR from pDII-Hor3 (Sørenson et al., 1996; Cho et al., 1999a). This plasmid contained the D-hordein promoter sequence, which was used as a template, creating SphI and XbaI sites with the following primers: Dhor1 (5'-ggcgcatgcgaattcGATTCGATATCGATCTTCGA-3') (SEQ ID NO:23) and Dhor2 (5'-aactctagaCTCGGTGGACTGTCAATG-3') (SEQ ID NO:12), respectively. Small letters in the primers contain restriction enzyme sites for subcloning of the DNA fragment containing the D-hordein promoter; underlined letters denote D-hordein promoter sequences. The PCR amplified D-hordein promoter fragment was digested with SphI and XbaI and replaced with the cauliflower mosaic 35S (CaMV 35S) promoter in p35SGN-3 to generate the pDhGN-2 plasmid. p35SGN-3 was made by ligating the 3.04kb SphI-EcoRI fragment containing the CaMV 35S promoter, uidA (beta-glucuronidase, gus) gene and nos into the SphI/EcoRI-digested pUC18.

(2) pdBhWTRX-1 The construction of pdBhWTRXN-1 started by using pBhWTRXN-1. pBhWTRXN-1 was made by replacing the uidA gene in pBhGN-1, which contains uidA driven by the barley endosperm-specific B1-hordein promoter and terminated by the nos 3' terminator, with the XbaI/SacI fragment from pWTRXh-1, which contains the wtrxh coding sequence. The 120-bp HindIII-5' B1-hordein flanking region was deleted from the pBhWTRXN-1 and religated to make the pdBhWTRXN-1 construct.

(3) pdBhssWTRXN3-8: Primers Bhor7 (5' GTAAAGCTTTAACAACCCACACATTG) (SEQ ID NO:7) and BhorWtrxh1R (5'-CCGACGCCGCTGCAATCGTACTTGTTGCCGCAAT) (SEQ ID NO:8) containing HindIII and AcyI sites, respectively, were used for amplification of a 0.49kb $B_1$-hordein 5'-region, which included the B1-hordein signal peptide sequence (FIG. 6). λ2-4/HindIII plasmid containing a genomic clone of B1-hordein (Brandt et al., 1985; Cho and Lemaux, 1997) was used as a template for the amplification. The primer BhorWtrxh1R is an overlapping primer, which contains the wtrxh coding sequence (underlined) and a partial signal peptide sequence from the B1-hordein promoter, but lacks the ATG initiation codon for wtrxh. pdBhssWTRXN38 was made by replacing the D-hordein promoter (FIG. 7) in pDhWTRXN-2 with the 0.49kb PCR-amplified HindIII/AcyI fragment, which contains the B1-hordein promoter, its signal peptide sequence and the junction region from the 5' trxh gene. Thus, construct pdBhssWTRXN3-8 contains the barley endosperm-specific B1-hordein promoter with its signal peptide sequence (FIG. 6), wtrxh ,and nos (FIG. 1). The signal peptide sequence containing the ATG initiation codon was directly combined with the sequence of wtrxh, with no extra amino acid sequences being introduced between the two. This ensures that the WTRXh protein has a precise cleavage site in the lumen of the endoplasmic reticulum (ER). The authenticity of a PCR-amplified fragment from the chimeric product was confirmed by DNA sequencing.

(4) pGlb1WTRXN-1: The 1.42-kb HindIII/BamHI fragment containing the maize embryo-specific globulin promoter from the ppGlb1GUS plasmid (Liu and Kriz, 1996) was ligated into pBluescript II KS(+) to create HindIII and XbaI sites. pGlbWTRXN-1 was made by restricting pDhWTRXN-2 with HindIII and XbaI in order to remove the 0.494-kb HindIII/XbaI barley D-hordein promoter from the pDhWTRXN-2. In place of the 0.49-kb HindIII/XbaI D-hordein promoter fragment (FIG. 7), the 1.42-kb HindIII/, XbaI maize globulin promoter was ligated into the HindIII/XbaI digested pDhWTRXN-2 to form the pGlbWTRXN-1 plasmid.

Stable Barley Transformation

Stable transgenic lines of barley expressing WTRXh driven by the B1-hordein promoter with and without the signal peptide sequence (FIG. 6), by the D-hordein promoter (FIG. 7) and by the maize globulin promoter were obtained following modifications of published protocols (Wan and Lemaux 1994: Lemaux et al., 1996: Cho et al., 1998a–c). Whole immature embryos (IEs) (1.0–2.5 mm) were aseptically removed, placed scutellum-side down on DC callus-induction medium containing 2.5 mg/L 2,4-D and 5 μM $CuSO_4$ (Cho et al., 1998a–c). One day after incubation at 24±1° C. in the dark, the IEs were transferred scutellum-side up to DC medium containing equimolar amounts of mannitol and sorbitol to give a final concentration of 0.4 M. Four hours after treatment with the osmoticum the IEs were used for bombardment Gold particles (1.0 μm) were coated with 25 μg of a 1:1 molar ratio of pAHC20 (Christensen and Quail, 1996) and one of the following plasmids. pdBhWTRXN-1, pdBhssWTRXN3-8, pDhWTRXN-2 and pG1bWTRXN-1. The microprojectiles were bombarded using a PDS-1000 He biolistic device (Bio-Rad, Inc., Hercules, Calif.) at 1100 psi. Bombarded IEs were selected on DC medium with 5 mg/L bialaphos for 2 to 3 months. Bialaphos-resistant callus was transferred onto an intermediate culturing medium (DBC2; Cho et al., 1998a–c), containing 2.5 mg/L 2,4-D, 0.1 mg/L BAP and 5.0 μM $CuSO_4$, between the selection [DC medium plus bialaphos (Meiji Seika Kaisha, Ltd., Yokohama, Japan)] and regeneration (FHG medium; Hunter, 1988) steps. The culturing after callus induction and selection on DC medium were carried out under dim light conditions (approximately 10 to 30 μE, 16 h-light) (Cho et al., 1998a–c). Regenerated shoots were transferred to Magenta boxes containing rooting medium (callus-induction medium without phytohormones) containing 3 mg/L bialaphos. When shoots reached the top of the box, plantlets were transferred to soil in the greenhouse.

Cytological Analysis

For cytological analysis of transgenic barley plants, healthy root meristems were collected from young plants grown in the greenhouse. After pre-treatment at 4° C. in saturated 1-bromonaphthalene solution overnight, root meristems were fixed in 1:3 glacial acetic acid:ethanol and stored at 4° C. Root meristems were hydrolyzed in 1 M HCl at 60° C. for 5–7 min, stained in Feulgen solution and squashed on a glass slide in a drop of 1% aceto-carmine. Chromosomes were counted from at least five well-spread cells per plant.

Herbicide Application

To determine herbicide sensitivity of $T_0$ plants and their progeny, a section of leaf blade at the 4- to 5-leaf stage was painted using a cotton swab with 0.25% (v/v) Basta™ solution (starting concentration 200 g/L phophinothricin, Hoechst AG, Frankfurt, Germany) plus 0. 1% Tween 20. Plants were scored 1 week after herbicide application.

Polymerase Chain Reaction (PCR) and DNA Blot Hybridization

Total genomic DNA from leaf tissues was purified as described by Dellaporta (1993). To test for the presence of wtrxh in genomic DNA of putatively transformed lines, 250 ng of genomic DNA was amplified by PCR using one of two primer sets:

Set 1:
  Wtrxh1 (5'-ATATCTAGAATGGCGGCGTCGGCGGCGA) (SEQ ID NO:5) and
  Wtrxh2R (5'-ATAGAGCTCTTACTGGGCCGCGTGTAG) (SEQ ID NO:6); or Set 2:
  Wtrxh4 (5'-CCAAGAAGTTCCCAGCTGC) (SEQ ID NO:11) and
  Wtrxh5R (5'-ATAGCTGCGACAACCCTGTCCTT) (SEQ ID NO:19).

The presence of bar was determined using the primer set:
  BAR5F (5'-CATCGAGACAAGCACGGTCAACTTC3') (SEQ ID NO:13) and
  BAR1R (5'-ATATCCGAGCGCCTCGTGCATGCG) (SEQ ID NO:14) (Lemaux et al., 1996).

Amplifications were performed with Taq DNA polymerase (Promega, Madison, Wis.) in a 25 µl reaction (Cho et al., 1998a–c). Twenty-five microliters of the PCR product with loading dye were subjected to electrophoresis in a 1.0% agarose gel with ethidium bromide and photographed using exposure to UV light Presence of 0.4- and 0.14-kb fragments was consistent with intact and truncated wtrxh fragments, respectively; an internal 0.34-kb fragment was produced from the bar gene with bar primers. Hormozygous fines for wtrxh were screened by PCR and western blot analysis in $T_2$ or $T_3$ plants.

For DNA hybridization analysis, 10 µg of total genomic DNA form leaf tissue of each line was digested with HindIII and SacI, separated on a 1.0% agarose gel, transferred to Zeta-Probe GT membrane (Bio-Rad, Hercules, Calif.) and hybridized with a radiolabeled wtrxh-specific probe following the manufacture's instructions. The wtrxh-containing 0.4 kb XbaI-SacI fragment from pDhWTRXN-9 was purified by QIAEX gel extraction kit (QIAGEN, Chatsworth, Calif.) and labeled with $^{32}$P-dCTP using random primers.

Western Blot Analysis

Western blot analysis was performed on seeds from selected transgenic lines as well as from control barley seeds from non-transgenic Golden Promise grown under the same conditions as the transgenic plants and form control wheat seeds of a durum wheat cultivar, cv. Monroe, or a bread wheat cultivar cv. Capitale. Whole seeds were ground to a fine powder with a mortar and pestle under liquid nitrogen. Ten to 20 seeds were used for each sample; the volume of extraction buffer (50 mM Tris HCl or phosphate buffer, pH 7.8, 0.5 mM phenylmethyl sulfonyl fluoride [PMSF], 1 mM EDTA) varied from 2 to 4 ml depending on the number of seeds used and the viscosity of the extract. Grinding was continued for an additional minute after buffer addition; the mixture was then centrifuged at 14,000×g for 10 minutes and the supernatant solution was saved as the albumin-globulin fraction that contained the thioredoxin.

SDS-PAGE of the albumin-globulin fraction was performed in 12–17% polyacrylamide gradient gels at pH 8.5 (Laemmli, 1970). From each sample equal amounts of protein (~40 µg) quantitated according to Bradford (1976) were diluted 1:2 v/v in Laemmli sample buffer, boiled for 3 minutes, loaded onto gels and subjected to electrophoresis at a constant current of 15 mA. Proteins were transferred to nitrocellulose at a constant voltage of 40 V for 4 hours at 4° C. using a Hoefer Transphor Transfer Unit (Alameda, Calif.). Nitrocellulose was blocked with 5% powdered milk in TBS for 2 hours at room temperature (RT), incubated in primary antibody for 4 hours at RT and in secondary antibody for 1 hour at RT. Primary antibody was wheat anti-thioredoxin h II Ab (Johnson et al. ,1987b) diluted 1 to 500; secondary antibody was goat anti-rabbit alkaline phosphatase (Bio-Rad, Hercules Calif.) diluted 1:3000. Blots were developed in NBT/BCIP alkaline phosphatase color reagent (according to Bio-Rad instructions); gets were stained with Coomassie blue to assure transfer. Images were scanned using a Bio-Rad GelDoc 1000 (Hercules, Calif.) and analyzed using Bio-Rad Multi Analyst, version 1.0.2. All bands were scanned over the same area, using a rectangle of comparable density as background; results were expressed as % of volume scanned. The number shown represents the percent of the total volume (pixel density X area of scanned band).

WTRXh Activity Measurements

Preparation of Materials for Extraction.

Mature grains from various heterozygous and hormozygous transgenic lines served as starting materials for the assay. Heterozygous lines with a D-hordein promoter were: GPDhBarWtrx-5, GPDhBarWtrx-9-1, and GPDhBarWtrx-9-2. Heterozygous lines with a B-hordein promoter and no signal sequence were: GPdBhBarWtrx-2, -5, -9, -19 and GPdBhBarWtrx-20. Heterozygous lines with a B-hordein promoter plus a signal sequence were: GPdBhssBarWtrx-2, -7, GPdBhssBarWtrx-29, GPdBhssBarWtrx-20, GPdBhssBarWtrx-14, GPdBhssBarWtrx-22. Homozygous lines with a signal sequence were GPdBhssBarWtrx-2-17, GPdBhssBarWtrx-2-17-1, GPdBhssBarWtrx-293 and GPdBhssBarWtrx-29–32. Control materials included a non-transformed tissue culture derived line, 4-96, a transformed line containing only bar, GPBar-1, and null segregant lines, GPdBhssBarWtrx-29-11 and GPdBhssBarWtrx-29-11-10, derived from line GPdBhssBarWtrx-29.

Preparation of $NH_4)_2SO_4$ Extracts for Get Filtration

Approximately fifteen grams of barley grains were ground to powder in a coffee grinder and extracted with 80 ml (1:4 w/v) of buffer [(50 mM Tris-HCl buffer, pH 7.9, 1 mM EDTA, 0.5 mM PMSF (phenylmethysulfonyl fluoride)], 2 mM e-amino-n caproic acid, 2 mM benzamidine-HCl) by stirring for 3 hrs at 4° C. The slurry plus the rinse was subjected to centrifugation at 25,400×g for 20 min, the supernatant solution was decanted through glass wool, pellets were resuspended in a small volume of buffer and then clarified by centrifugation as before. The supernatant fractions were combined, an aliquot was removed and the remainder was subjected to acidification by adjusting the pH from 7.83 to 4.80 with 2 N formic acid; denatured proteins were removed by centrifugation as above prior to assay. The pH of the acidified supernatant solution was readjusted to 7.91 with 2 N $NH_4OH$ and an aliquot was removed for assay. Powdered $(NH_4)_2SO_4$ was added to a final concentration of 30% and the sample was stirred for 20 min at 4° C., followed by centrifugation as described above. The pellet was discarded. Additional $(NH_4)_2SO_4$ was added to bring the decanted supernatant solution to 90% saturation; the sample was stirred for 16 hrs at 4° C., followed by centrifugation as described above.

The supernatant solution was discarded, the 30–90% $(NH_4)S_2O_4$ pellets were resuspended in 30 mM Tris-HCl, pH 7.9 buffer and then subjected to centrifugation at 40,000×g for 15 min to clarify. The resulting supernatant (30–90% $(NH_4)_2SO_4$ fraction) was added to dialysis tubing (6,000–8,000 MW cut-off) and exposed to solid sucrose at 4° C. to obtain a 10-fold reduction in volume. An aliquot (1 ml) of the clarified and concentrated 30–90% $(NH_4)_2SO_4$) sample was saved and the remaining sample was applied to a pre-equilibrated (30 mM Tris-HCl, pH 7.9, 200 mM NaCl) Sephadex G-50 superfine column (2.5×90 cm; ~400 mL bed volume) with a peristaltic pump at a flow rate of 0.5 mL/min. Protein was eluted with the same buffer at the same flow rate; one hundred fifty drop-fractions were collected. Selected fractions were used to measure absorbance at 280 nm using a Pharmacia Biotech Ultrospec 4000 and to assay for TRXh activity following the NADP-MDH activation protocol (see below). Active fractions were pooled, stored at 4° C., and then assayed for total NADP-MDH activation activity.

Preparation of Heat-Treated Extracts

Approximately 10 grams of barley grains were ground to powder for about 30 sec in a coffee grinder and extracted by shaking for 1 hr at room temperature in 50 mL buffer as above. The slurry plus the rinse was subjected to centrifugation at 27,000×g for 20 min and the supernatant solution decanted through glass wool. A 20 mL aliquot of each sample was heated at 65° C. until sample temperature reached 6±1° C. (~10 min). The sample was held at 60° C. for 10 additional min, followed by cooling in an ice/water bath. The cooled sample was centrifuged and the supernatant solution was concentrated by sucrose as above and stored at −20° C. Frozen samples were thawed and clarified by centrifugation at 14,000 rpm for 10 min at 4° C. Total TRXh activity was estimated on the concentrated, supernatant fractions.

NADP-Malate Dehydrogenase Activation Assay

Thioredoxin h activity was assayed as previously described (Florencio et al., 1988; Johnson et al., 1987a). Fifty to 120 µl of extract (depending on activity) was preincubated with DTT, and 0.16 to 0.32 µl of the pre-incubation mixture was used for the NADP-MDH assay. Control assays were conducted on identical fractions in the absence of NADP-MDH. Western blot analysis was conducted as described above except that 10 to 20% SDS-polyacrylamide gels were used for electrophoresis and transfer to nitrocellulose paper was for 4 hrs at 40 V.

Sequential Extraction of Multiple Protein Fractions

Ten grams of barley grain were sequentially extracted for albumin ($H_2O$-soluble), globulin (salt-soluble), hordeins (alcohol-soluble) and glutelins (Shewry et al., 1980). Barley powder was stirred with 0.5 M NaCl for 1 h at 25° C. to remove salt-soluble proteins. Two sequential hordein fractions were extracted from the residue with 50% propanol in the absence (hordein-I) and presence (hordein-II) of 2% (v/v) 2-mercaptoethanol. Glutelins were extracted from the residue with 0.05 M borate buffer, pH 10, containing 1% (v/v) 2-mercaptoethanol and 1% (v/v) sodium dodecylsulphate.

In vitro Monobrmobimane (mBBr) Labeling of Proteins

Immature, mature, or germinating seeds from nontransformed and transgenic plants were ground in 100 mM Tris-HCl buffer, pH 7.9. Reactions were carried out following the protocol of Kobrehel et al., (1992). Seventy microliters of the buffer mixture containing a known amount of protein was either untreated or treated with DTT to a final concentration of 0.5 mM. After incubation for 20 min, 100 nmol of mBBr was added, and the reaction was continued for another 15 min. To stop the reaction and derivatze excess mBBr, 10 µl of 10% SDS and 100 µl of 100 mM 2-mercaptoethanol were added. The samples were applied to a 15% SDS-PAGE gel. Fluorescence of mBBr was visualized by placing gels on a light box fitted with a UV light source (365 nm). Protein determination was carried out by the Bradford dye binding method (Bradford 1976) using bovine serum albumin or gamma globulin as standards.

Assay of Pullulanase and its Inhibitor

To measure pullulanase activity, grain was germinated in a dark chamber and retained for up to 5 days at 25° C. as described (Kobrehel et al., 1992.; Lozano et al., 1996.). A set of plates from each line was removed for extract preparation each day. Cell-free endosperm extracts were prepared from lots of 10–20 germinated grains of equivalent root and coleoptile length within a given cohort. Endosperm was separated from the embryo and other tissues and added to Tris-HCl buffer (50 mM, pH 7.9) supplemented with 1 mM EDTA and 0.5 mM PMSF (1:3 to 1:6, wt/vol ratio of tissue to buffer depending on developmental stage). After grinding in a mortar on ice, the sample was clarified by centrifugation (10 min at 24,000×g); the supernatant fraction was recovered and stored in 0.5-ml aliquots −80° C. for pullulanase spectrophotometric or gel assays.

Pullulanase activity was determined spectrophotometrically at 37° C. by measuring dye released after 30 min at 534 nm using red pullulan (Megazyme, Bray, Ireland) as substrate in 50 mM citrate-phosphate buffer (pH 5.2) (Serre et al., 1990.). Pullulanase also was assayed on native activity gels of 7.5% acrylamide, 1.5 mm thickness, containing 1% red pullulan (Furegon et al., 1994.). Gels were scanned using a Bio-Rad Gel Doc 1000 and analyzed using Bio-Rad MULTI ANALYST, version 1.0.2. Pullulanase inhibitor activity was determined on fractions heated to inactivate pullulanase (70° C. for 15 min) by measuring their ability to inhibit added purified barley malt pullulanase. Endogenous pullulanase activity was shown to be completely eliminated by this heat-treatment while the inhibitor activity was not affected (Macri et al., 1993; Macregor et al., 1994).

Alpha-Amylase Activity in Barley Grain Overexpressing Thioredoxin h

Amylase activity from the null segregant and hormozygous barley grains was analyzed during germination and early seedling growth by using gels containing starch. Native polyacrylamide electrophoresis gels [6% acrylamide, 1.5 mm thick] were prepared and developed according to the method of Laemmil (1970) except that SDS was omitted from all solutions. The separating gel contained 0.5% soluble starch (Lintner potato starch, Sigma Chemical Co., St. Louis, Mo.). Lyophilized samples were dissolved in distilled $H_2O$ and mixed 1:1 with a buffer consisting of 0.25

M Tris-HCl, pH 6.8. 50% glycerol, 0.04% bromophenol blue, and 3 mM $CaCl_2$. Fifty micrograms of sample protein were loaded in each lane. Electrophoresis was carried out at 80 milliamps per gel at 4° C. until the dye front was at the edge of the gel (usually 4 to 5 hours). After electrophoresis, the gels were incubated in 100 ml of 0.1 M succinate buffer, pH 6.0, for 1–2 hours at 37° C. The gels were then stained for 5 min in a solution containing 2.5 mM $I_2$ and 0.5 M KI. Gels were washed in distilled $H_2O$. Except for the white regions containing amylase activity, gels were stained dark blue.

Isoelectricfocusing (IEF)

For determination of alpha-amylase isozyme patterns, extracts from both dry and germinating grain of transformed and control (untransformed) barley were separated by electrophoresis at 4° C. [1.0 mm thick, pH 3–10 isoelectric focusing (IEF) polyacrylamide gets, using the X cell II system (NOVEX, San Diego, Calif.]. Cathode buffer contained 20 mM arginine, and 20 mM lysine; anode buffer was 7 mM phosphoric acid. Samples were mixed 1:1 and 2× IEF sample buffer pH 3–10 (NOVEX). After sample application (20 μg/lane) gels were developed at constant voltage [100 V for 1 hr, 200 V for an additional 1 hr, and 500 V for 30 min]. IEF standards (Bio-Rad) were used to determine the pH gradient of the gels.

Multiple Antibody Probing of IEF Gels

Western blot analysis of alpha-amylase isozymes was performed using a Mini Trans-Blot Electrophoretic Transfer Cell (Bio-Rad). Seed extracts from the null segregant and homozygous lines overexpressing wheat thioredoxin h were separated by IEF gels as described above. Proteins were transferred to nitrocellulose at a constant voltage of 100 V for 1 hr at 4° C. using 0.75% acetic acid as blotting buffer. Nitrocellulose was blocked with 5% powdered milk in Tris buffer solution (20 mM Tris-HCl, pH 7.5, supplemented with 0.15 M NaCl) for 1 hr at room temperature, incubated with primary antibody for 4 hours at room temperature and then with secondary antibody for 1 hour at room temperature. Primary antibody was anti-barley alpha-amylase B diluted 1:1000; secondary antibody was goat anti-rabbit alkaline phosphatase (Bio-Rad) diluted 1:3000. Blots were developed in NBT/BCIP alkaline phosphatase color reagent (according to Bio-Rad instructions) thereby rendering the cross-reacted alpha-amylase bluish-purple. To achieve full identity of isozyme pattern, blots were probed a second time with another primary antibody, anti-alpha-amylase A (diluted 1:1000) and the secondary antibody (as above). This time blots were developed In Naphthol Phosphate/Fast Red alkaline phosphatase color reagent (according to Bio-Rad instructions) which gave a pink stain to the alpha-amylase A. The blot shown was subject to this dual probing procedure.

B. Results and Discussion

Production of Transgenic Plants

One day after bombardment, the whole embryos were transferred onto DC medium with 5 mg/L bialaphos. At transfer to the second selection plate (5 mg/L bialaphos), all material from individual callusing embryos was broken into small pieces (2–4 mm) using forceps and maintained separately. During the subsequent two to five selection passages on 5 mg/L bialaphos (at 10–20 d intervals), callus pieces showing evidence of more vigorous growth were transferred to new selection plates. During the second round of selection, some pieces of callus were inhibited in growth and in some cases pieces turned brown. In general, transformed tissues were observed after three or more rounds of selection. The bialaphos-resistant tissues were transferred onto an intermediate medium, DBC2 or DBC3 (Cho et al., 1998a–c) with bialaphos (5 mg/L), and grown for 1 to 2 months before regeneration on FHG medium containing 3 mg/L bialaphos. Green plantlets were transferred into Magenta boxes containing 3 mg/L bialaphos. Twenty-eight independent putatively transformed, regenerable lines were produced after bialaphos selection (shown in Table 1).

TABLE 1

Transgenic Barley Lines Transformed with Wheat Thioredoxin h Gene.

| Plasmids for Bombardment | Transgenic Barley Line | DNA PCR ($T_0$ leaf) bar | wtrxh | TRXh Expression in $T_1$ seeds | Ploidy | Comments |
|---|---|---|---|---|---|---|
| pdBhWTRXN-1 + pAHC20 | GPdBhBarWTRX-1 | + | + | n.d. | Tetraploid | |
| | GPdBhBarWTRX-2 | + | + | + | Tetraploid | |
| | GPdBhBarWTRX-3 | + | + | + | Diploid | |
| | GPdBhBarWTRX-5 | + | + | + | Tetraploid | Sterile |
| | GPdBhBarWTRX-16 | + | − | n.d. | Tetraploid | |
| | GPdBhBarWTRX-17 | + | + | n.d. | Tetraploid | |
| | GPdBhBarWTRX-19 | + | + | + | Diploid | |
| | GPdBhBarWTRX-20 | + | + | + | Diploid | |
| | GPdBhBarWTRX-22 | + | + | + | Diploid | |
| | GPdBhBarWTRX-23 | + | + | + | Diploid | |
| pdBhssWTRXN3-8 + pAHC20 | GPdBhssBarWTRX-1 | + | − | − | Diploid | |
| | GPdBhssBarWTRX-2 | + | + | + | Diploid | Homozygous |
| | GPdBhssBarWTRX-3 | + | + | − | Diploid | |
| | GPdBhssBarWTRX-7 | + | + | + | Diploid | |
| | GPdBhssBarWTRX-9 | + | + | n.d. | Tetraploid | |
| | GPdBhssBarWTRX-11 | + | + | − | Diploid | |
| | GPdBhssBarWTRX-13 | + | + | + | Tetraploid | |
| | GPdBhssBarWTRX-14 | + | + | + | Diploid | |
| | GPdBhssBarWTRX-20 | + | + | + | Tetraploid | |
| | GPdBhssBarWTRX-21 | + | + | n.d. | Tetraploid | Sterile |
| | GPdBhssBarWTRX-22 | + | + | + | Tetraploid | |
| | GPdBhssBarWTRX-29 | + | + | + | Diploid | Homozygous |
| pDhWTRXN-2 + pAHC20 | GPDhBarWTRX-5 | + | + | + | Tetraploid | |
| | GPDhBarWTRX-7 | + | + | + | Diploid | |
| | GPDhBarWTRX-8 | + | + | + | Diploid | |

TABLE 1-continued

Transgenic Barley Lines Transformed with Wheat Thioredoxin h Gene.

| Plasmids for Bombardment | Transgenic Barley Line | DNA PCR ($T_0$ leaf) bar | wtrxh | TRXh Expression in $T_1$ seeds | Ploidy | Comments |
|---|---|---|---|---|---|---|
| | GPDBhBarWTRX-9 | + | + | + | Diploid | Homozygous |
| | GPDBhBarWTRX-22 | + | + | + | Diploid | Sterile |
| pGlbWTRXN-1 + pAHC20 | GPGlbBarWTRX-1 | + | + | + | Diploid | |

*n.d.: not determined

Analysis of $T_0$ Plants and Their Progeny

PCR analysis was performed using two sets of WTRXh primers and one set of BAR primers (see FIG. 1). PCR amplification resulted in 0.4-kb intact wtrxh or 0.14 kb truncated wtrxh and 0.34-kb internal bar fragments from transgenic lines. Of the 28 lines tested, 28 yielded bar fragments from $T_0$ leaf tissue and 26 produced PCR-amplified fragments for wtrxh, giving a 93% co-transformation frequency. Nine lines were transformed with pdBhWTRXN-1, eleven with pdBhssWTRXN-8, five with pDhWTRXN-2 and one with pG1bWTRXN-1 (see Table 1). Three lines (GPdBhBarWtrx-5, GPdBhssBarWtrx-21 and GPDhBarWtrx-22) were sterile. Seeds of $T_0$ plants and their progeny from selected wtrxh-positive lines were planted in order to screen for homozygous lines. Homozygous lines and null segregants were obtained from GPdBhssBarWtrx-2, -29 and GPDhBarWtrx-9 (see Table 1).

Cytological Analysis of Transgenic Plants

Chromosomes were counted in root meristems cells of independently transformed $T_0$ barley plants. Out of 28 independent transgenic lines examined, 17 lines had the normal diploid chromosome complement (2n=2x=14), while the remaining 11 lines were tetraploid (2n=4x=28) (see Table 1).

Characterization and Content of WTRXh Produced in Transgenic Seed

As discussed above, several stably transformed barley lines were obtained that express wheat thioredoxin h. As seen In FIG. 2, the stable introduction of the wtrxh linked to the B1-hordein promoter with the signal peptide sequence resulted in greatly enhanced expression of active WTRXh in transgenic barley seed.

Analysis by western blot of soluble protein fractions of the three fines in which the thioredoxin gene was linked to a signal sequence (GPdBhssBarWtrx-22, GPdBhssBarWtrx-29 and GPdBhssBarWtrx-7) showed differences in the level of expression (shown in Table 2). Line GPdBhssBarWtrx-22, GPdBhssBarWtrx-29 and GPdBhssBarWtrx-7, respectively, showed 22 times, 10 times and 5.5 times more WTRXh protein than nontransformed control seeds. The analyses showed that the thioredoxin content of the null segregant (GPdBhssBarWtrx-29-11) was approximately half that of the corresponding control. The three lines generated from the construct in which the thioredoxin gene was not associated with a signal sequence were also compared to nontransformed control barley seed and they exhibited the following increases in TRXh levels as indicated by the western blot analyses: GPDhBarWtrx-9: 12 times; GPDhBarWtrx-5: 6.3 times; GPdBhBarWtrx-2: 6.4 times. When probed on Western Blots, the transgenic lines show two bands while the control barley generaly shows only one and in some cases a second minor band. Furthermore, the tissues from the transgenic lines were characterized by a band that did not correspond to either of the barley bands but did correspond to wheat thioredoxin h. These data indicate that the protein introduced by transformation is wheat thioredoxin h.

TABLE 2

Western Blot Analyses of Overexpression of Wheat Thioredoxin h in Barley.

| Barley Line | % Volume Scanned | Fold Increase (or Decrease) |
|---|---|---|
| Non-Transformed Control: | | |
| Golden Promise | 1.46 | 1.0 |
| Transformed with Signal Sequence: | | |
| GPdBhssBarWtrx-22 | 32.44 | 22 |
| GpdBhssBarWtrx-29 | 14.62 | 10 |
| GpdBhssBarWtrx-7 | 7.99 | 5.5 |
| Transformed without Signal Sequence: | | |
| GPDhBarWtrx-9 | 17.69 | 12 |
| GPDhBarWtrx-5 | 9.20 | 6.3 |
| GPDhBarWtrx-2 | 9.29 | 6.4 |
| Null Segregant: | | |
| GPdBhssBarWtrx-29-11-10 | 0.93 | (0.64) |

The Wheat Thioredoxin h in Barley Grains is Biologically Active

Because of interference from other enzymes that oxidize NADPH, the activity of TRXh cannot be accurately assayed in crude extracts, thereby necessitating its partial purification. Partially purified extracts of the different transgenic and control lines were prepared from 15 grams of seed using ammonium sulfate fractionation and gel filtration chromatography. Activity was measured with an NADP-MDH activation assay. Profiles based on these assays show that the activity of TRXh in the transformed seed is much higher than in the nontransformed control (see FIG. 2). The activity results are summarized in Table 3.

Total WTRXh activity from the seeds of two lines transformed with the B1-hordein promoter and the signal sequence (GPBhssBarWtrx-3; GPdBhssBarWtrx-29) is about 4- to 10-fold higher, respectively, than that of control, nontransformed seed. Total activity from a line transformed with the D-hordein promoter without the signal sequence (BGPDhBbarWtrx-5) is only slightly higher (1.25-fold) than that of the nontransformed control (see Table 3). In the transgenics, the specific activity of thioredoxin is generally about 0.128 $A_{340\ nm}$/min/mg protein or about two fold over null segregants.

TABLE 3

Summary of Total Buffer-Extracted Protein and Total Thioredoxin Activity from Active Fraction after Gel Filtration.

| Barley Line | Total Protein, mg | Total Activity, $A_{340}$/min | Specific Activity, $A_{340}$/min/mg |
|---|---|---|---|
| Control (GP 4-96) | 102.6 (1.00)* | 7.4 (1.00)* | 0.064 (1.00)* |
| GPDhBarWtrx-5 | 171.2 (1.67) | 9.2 (1.2) | 0.054 (0.8) |
| GpdBhssBarWtrx-29 | 149.1 (1.45) | 72.0 (9.7) | 0.483 (7.5) |
| GpdBhssBarWtrx-3 | 231.3 (2.25) | 27.7 (6.4) | 0.794 (12.4) |

*Numbers in brackets are fold increase over that of the control.

The transformed barley grains analyzed so far appear to have more total buffer-extracted protein than control, non-transformed seed (Table 3).

The transformed grains have a thioredoxin content of at least about 10–15 μg thioredoxin/mg soluble protein(about 2–8 μg thioredoxin/mg tissue) or about two-fold higher than the null segregant.

Figure 3:
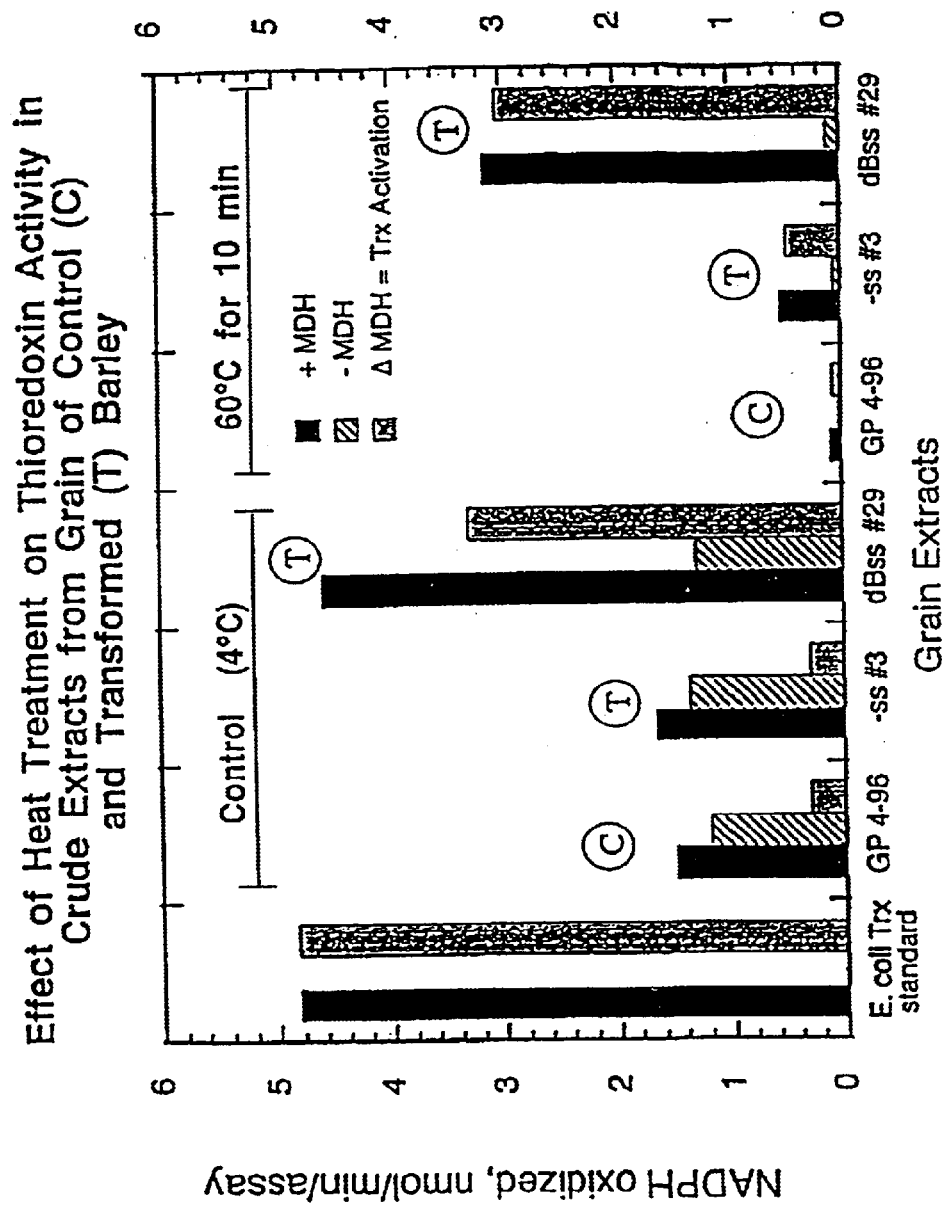
FIG. 3 shows the effects of heat treatment on thioredoxin activity of crude extracts from barley grains.

Because of the tediousness of the $(NH_4)_2SO_4$ procedure and the requirement for large quantities of seed, the original extraction procedure was modified to include a heat treatment step. This change was based on the fact that E. coli WTRXh is stable after treatment at 60° C. for 10 min (Mark and Richardson, 1976). Results on WTRX from two different transgenic barley seeds (GPdBhBarWtrx-3, GPdBhssBarWtr-29) showed no significant difference in activity between the heat treated and non-heat treated extracts (FIG. 3). In addition heat-treatment decreased the endogenous, nonspecific activity in this assay, thereby increasing the reliability of the measurements.

Ten different barley lines (transformed and nontransformed) were extracted using the heat-treatment step and assayed with the NADP-MDH assay; the results are summarized in Table 4. In general, total WTRXh activities in seeds from lines transformed with the B-hordein promoter and signal sequence linked to wtrxh are much higher (4- to 35-fold) than in seeds from lines transformed with the same promoter without signal sequence linked to wtrxh or in seeds from the nontransformed control (Table 4). At this point it is not known whether all expressed wheat WTRXh in barley seeds is heat stable

TABLE 4

Relative Total Thioredoxin Activity in Different Transgenic Barley Lines.

| Line Designation | Total Protein (%) | Total Activity (%) | Specific Activity (%) |
|---|---|---|---|
| Non-transgenic control | | | |
| GP4-96 | 100 | 100 | 100 |
| Bar Gene Only | | | |
| GPBar-1 | 92 | 120 | 131 |
| Without Signal Sequence | | | |
| GPdBhBarWtrx-1 | 101 | 192 | 190 |
| GPdBhBarWtrx-22 | 113 | 151 | 133 |
| GPdBhBarWtrx-23 | 118 | 180 | 153 |
| With Signal Sequence | | | |
| GPdBhssBarWtrx-2 | 137 | 1650 | 1203 |
| GPdBhssBarWtrx-14 | 122 | 1723 | 1418 |
| GPdBhssBarWtrx-20 | 147 | 440 | 299 |
| GPdBhssBarWtrx-22 | 154 | 3470 | 2245 |
| GPdBhssBarWtrx-29 | 108 | 1316 | 1219 |

One hundred percent of (a) total protein, mg; (b) total activity, nmol/min; and (c) specific activity, nmol/min/mg protein of the non-transgenic control are: (a) 116.4; (b) 157.38 (c) 1.52, respectively.

Of the stably transformed lines that expressed wheat thioredoxin h, on average, its level was found to be higher in transformants that had the signal peptide-containing constructs than to those that did not (Table 4). Western blot analysis of soluble protein fractions from heterozygous mixtures of seeds from three of the lines, GPdBhssBarWtrx-7, GPdBhssBarWtrx-29, and GPdBhssBarWtrx-22 showed 5.5 times, 22 times, and 10 times more thioredoxin h, respectively, than nontransformed control grain (Table 2). The thioredoxin content of the null segregant (GPdBhssBarWtrx-29-11-10) was about half that of the corresponding, nontransformed control.

Figure 4:
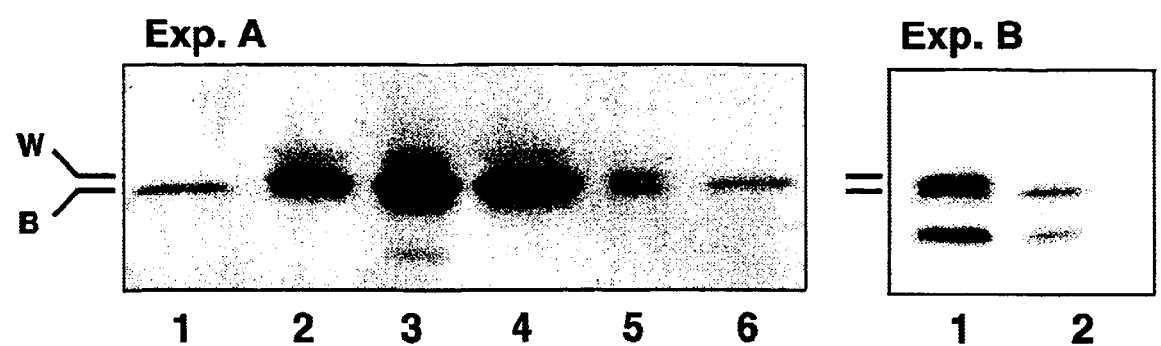
FIGS. 4A–B shows a western blot analysis of extract from segregating $T_1$ barley grain of stable transformants containing wtrxh. Panel A: lanes 1 and 6, control barley extract (cv. Golden Promise); lane 2, bread wheat extract (*Triticum aestivum*, cv. Capitole); lane 3, extract from GPdBhss Bar-Wtrx 22; lane 4, extract from GPdBhssBarWtrx 29; lane 5, extract from GPdBhBarWtrx 2. Panel B: lane 1, GPdBh-BaarWtrx 2; lane 2 control barley extract W, wheat; B, barley.

Extracts from barley typically showed one immunologically reactive band (identified by B in FIG. 4A, lanes 1 and 6) but in some transfers showed a second faint, faster moving band (FIG. 4B, lane 2). Tissues from transgenic lines overexpressing wtrxh were characterized by a band that did not correspond to either of the two counterparts in barley, but rather to thioredoxin h from wheat The difference between the overexpressed 13.5-kDa wheat and the endogenous 13.1-kDa barley thioredoxin h is particularly pronounced in the barley line transformed with the nontargeted thioredoxin h gene (FIG. 4A, line 5 and FIG. 4B, lane 1). Repeated analyses of the various transgenic lines by SDS/PAGE led to the conclusion that the band identified in FIGS. 4A–B by W corresponds to the bread wheat wtrxh introduced by barley. Independent biochemical assays with 5,5'-dithiobis(2-nitrobenzoic acid) (DTNB) (Florencio et al., 1988.) confirmed the ability of barley NTR to reduce wheat thioredoxin h (data not shown).

Figure 5:
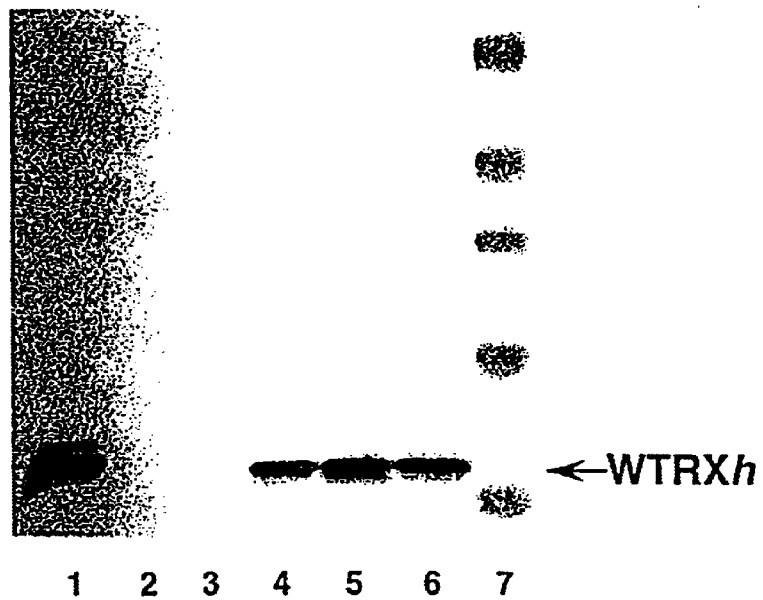
FIG. 5 shows western blot analysis of extracts of $T_1$, $T_2$ and $T_3$ barley grain transformed with wtrxh. Forty micrograms of soluble proteins extracted from 10–20 grains of each line were fractionated by SDS/PAGE. Lane 1, wheat germ thioredoxin h; lane 2, nontransgenic control of GP4-96; lane 3, null segregant $T_2$ grain of GPdBhssBarWtrx-29-11-10; lane 4, heterozygous $T_1$ grain of GPdBhssBarWtrx-29; lane 5, homozygous $T_2$ grain of GPdBhssBarWtrx-29-3; lane 6, homozygous $T_2$ grain of GPdBhssBarWtrx-29-3-2; lane 7, prestained standards (aprotinin, 0.9 kDa; lysozyme, 17.8 kDa; soybean trypsin inhibitor, 30.6 kDa, carbonic anhydrase, 41.8 kDa; BSA, 71 kDa).

Because of their value in assessing biochemical attributes of the grain, homozygous wtrxh lines were identified and analyzed by Western blot. The two lines identified as homozygous showed both enhanced expression of thioredoxin h relative to that of their heterozygous parents and nontransformed controls. Analysis of GPdBhssBarWtrx-29-3 is shown in FIG. 5. It is noted that demonstration of the thioredoxin h present in the nontransgenic control and null segregant grains (not apparent in the exposure shown in FIG. 4) required conditions that led to overexposure of the enriched transgenic preparations. Thioredoxin in the parent heterozygous grain was shown to be biochemically active.

Pullulanase and Pullulanase Inhibitor Activity in Barley Grain Overexpressing Thioredoxin h Pullulanase is an amylolytic enzyme present in cereal grain, which has a disulfide inhibitor protein (Macri et al., 1993.; MacGregor et al., 1994.), the activity of which is linked to thioredoxin (Wong et al., 1995.). Thioredoxin reduced by NADPH via NTR, reduces the disulfide bonds of the inhibitor, allowing the targeted pullulanase enzyme to be active. Because of this relationship, it was of interest to determine the activity of pullulanase in the thioredoxin h-overexpressing transformants.

Figure 8A:
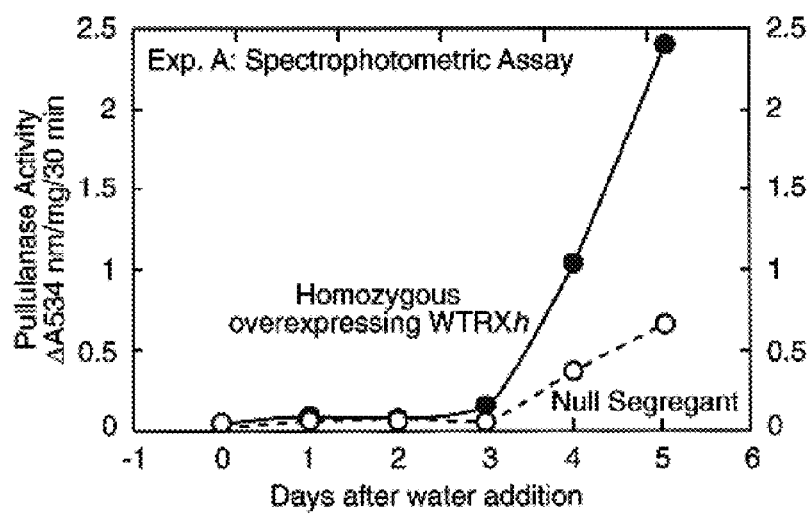
FIGS. 8A–C shows the effect of overexpressed thioredoxin h on pullulanase activity in transgenic barley grain during germination and seedling development. A hormozygous line, GPdBhssBarWtrx-29-3, and a null segregant, GPdBhssBarWtrx-29-11-10, were used for the pullulanase assays. Panel A: Pullulanase was assayed spectrophotometrically by measuring the dye released from red pullulan substrate at 534 nm. Panel B: Pullulanase was separated on native 7.5% polyacrylamide gels containing the red pullulan substrate. Activity, identified by comparison with purified barley pullulanase, is seen as clear areas that developed on incubating the gel in 0.2 M succinate buffer, pH 6.0, for 1 hr at 37° C. Panel C: The gel in Panel B was scanned and analyzed by integration of the activity bands.
Figure 8B:
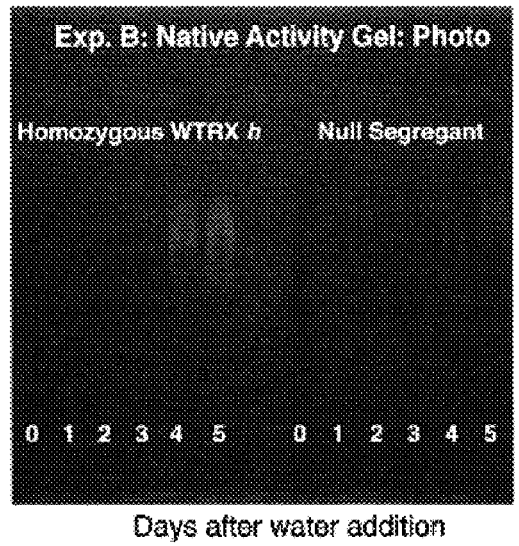
Figure 8C:
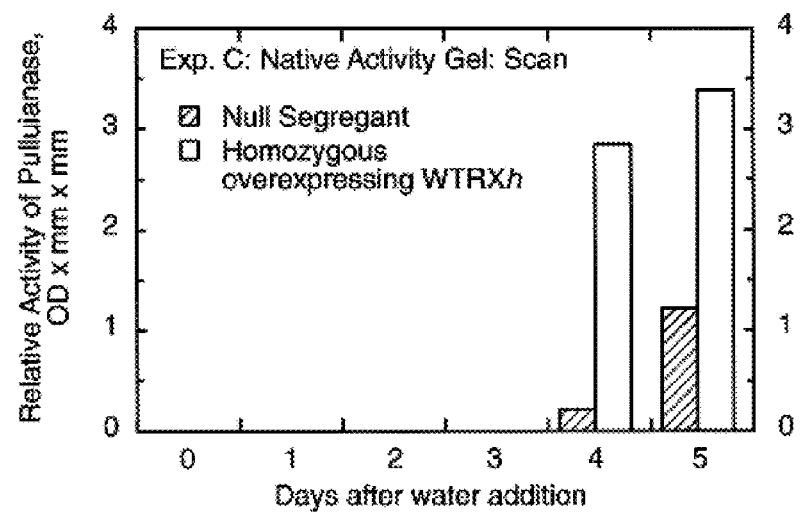

Spectrophotometric assays (FIG. 8A) of extracts from transformed grain of a homozygous line (GPdBhssBarWtrx- 29-3) overexpressing thioredoxin h showed a 3- to 4-fold increase in pullulanase activity on the fifth day after initiation of germination relative to its null segregant. Confirmatory results were obtained in a separate experiment with native activity gels. The increase in activity was apparent either when gels were viewed directly (FIG. 8B) or when the activity on the gels was assessed by scanning and integrating the clarified bands (FIG. 8C). A homozygous line isolated from a different, independent transformation event (GPdBssBarWtrx-2-1-15) showed a similar response (data not shown). The transgenic plants expressed an pullulanase activity of about 1–2 Absorbance units at 534 nm/30 min/mg protein, which is about twofold higher than null segregants.

Pullulanase inhibitor activity was determined on fractions heated to inactivate pullulanase (70° C. for 15 min) by measuring the inhibition of the fractions on added purified barley malt pullulanase. The endogenous pullulanase activity was shown to be completely eliminated by this heat treatment whereas inhibitor activity was not affected (Macri et al., supra; MacGregor et al., supra). Analysis of comparable grain extracts revealed that the pullulanase inhibitor was inactive on the fourth and fifth days after water addition in both the transformant and null segregants. These results thus demonstrate that the increase in pullulanase activity observed after the third day is not caused by enhanced inactivation of the inhibitor in the transgenic grain. It is possible that thioredoxin acts either by increasing the de novo synthesis of pullulanase (Hardie et al., 1975.) or by lowering the binding of the mature enzyme to the starchy endosperm. There is evidence that some of the pullulanase of the mature endosperm is present in bound form and can be solubilized by reducing conditions (Sissons et al., 1993.; Sissons et al., 1994.).

Alpha-Amylase Activity in Barley Grain Overexpressing Thioredoxin h

Alpha-amylase, also an amylolytic enzyme that is induced by gibberellic acid like pullulanase, has long been considered key to germination. The synthesis of the major (B) and minor (A) forms of this enzyme are known to be triggered by the hormone, gibberellic acid (GA). In addition, alpha-amylase activity is increased in vitro by the reductive inactivation of its disulfide inhibitor protein by thioredoxin h (in the presence of NADPH and NADP-thioredoxin reductase). The present results with transformed barley seeds show that, like pullulanase, thioredoxin h expression alters alpha-amylase activity. In this case, the appearance of the enzyme during germination is accelerated and its abundance and activity are increased.

Figure 10:
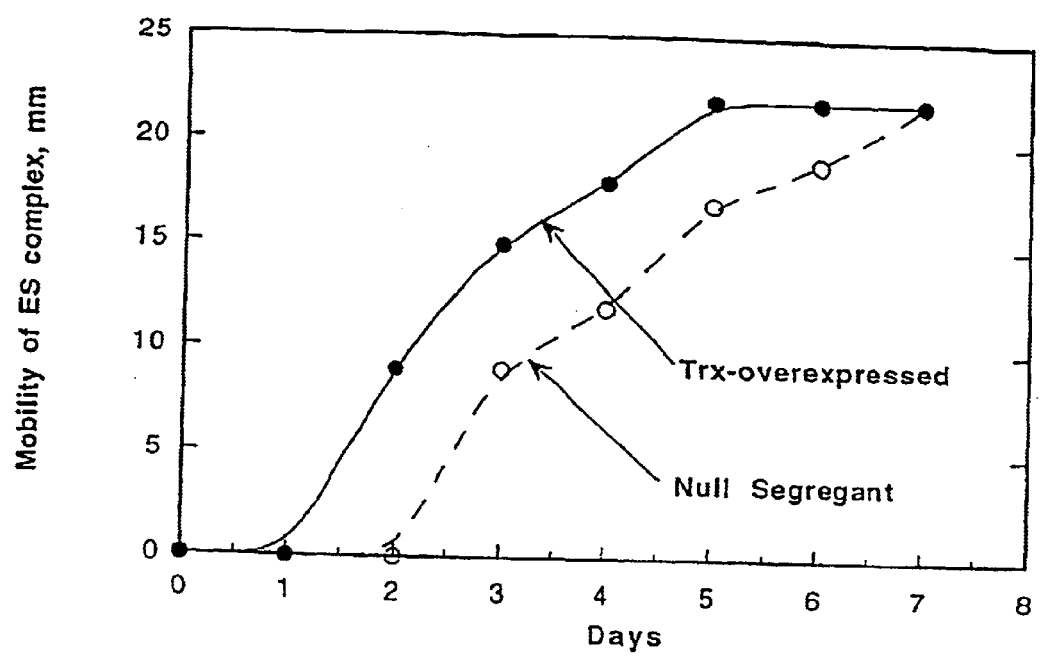
FIG. 10 shows the effect of overexpressed thioredoxin h on the activity of the major form of alpha-amylase during germination and seeding development. The size of the major alpha-amylase activity band in FIG. 9 was estimated by its rate of mobility during electrophoresis.
Figures 11A, 11B:
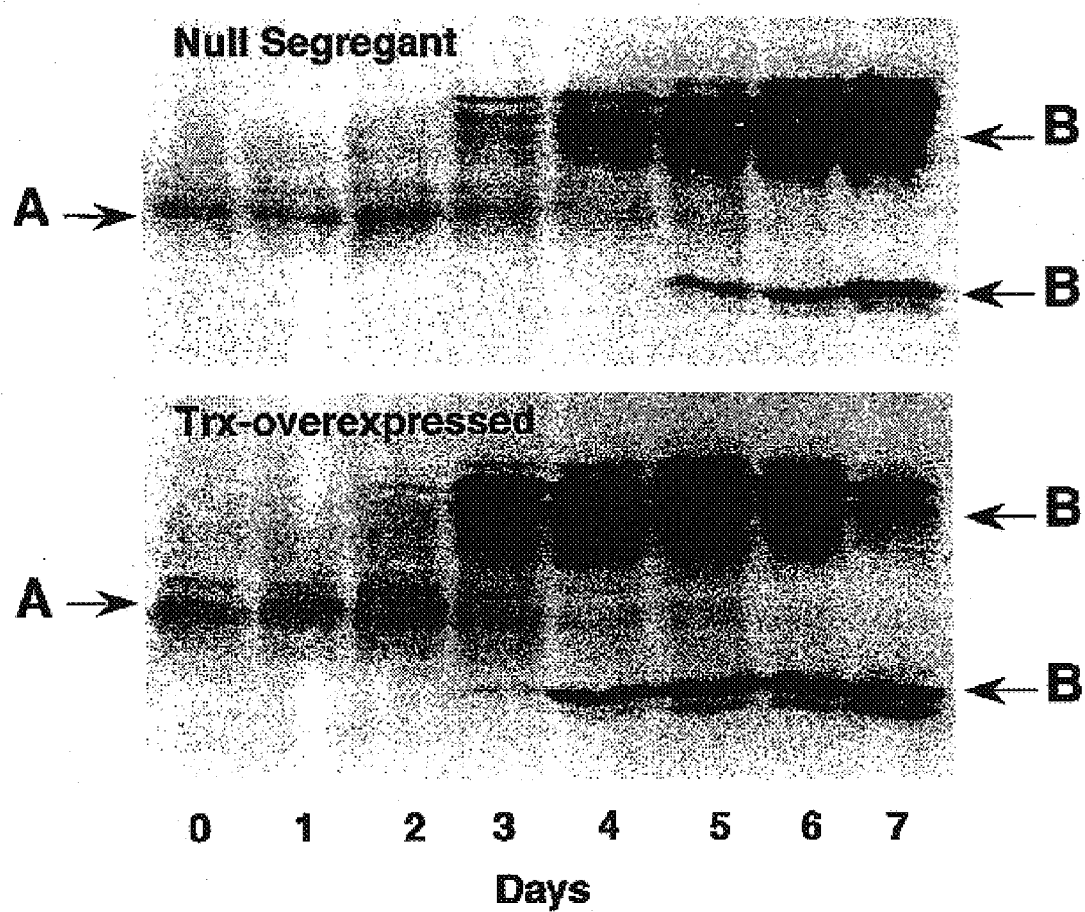
FIGS. 11A–B shows the effect of overexpressed thioredoxin h on the abundance of alpha-amylase A and B isozymes during germination and seedling development. The figure represents western blots of IEF gels developed for the null segregant and transgenic barley grains. Panel A: Null segregant. Panel B: Transgenic with thioredoxin overexpressed.

FIG. 9A–D shows the early increase in both the abundance and activity of alpha-amylase (A+B forms) during germination and seedling development. Based on the antibody response in western blots, alpha-amylase was first detected 3 days after the onset of germination in the transgenic grain FIG. 9C) whereas the enzyme did not appear until the fourth day in the null segregant (FIG. 9A). The onset of activity (based on the activity gel) followed a similar pattern (FIG. 9B and FIG. 9D). The mobility of the enzyme in the activity gel also reflected the early induction of activity in the transgenic grain (FIG. 10). That much of this increase in activity seen early on was due to the B (a gibberellic acid-linked form) is supported by FIG. 11. Here, one can also see that the level of the minor A form of the enzyme (also gibberellic acid dependent) was Increased in grain overexpressing thioredoxin h. Again, the appearance of significant levels of the major (B form) alpha-amylase enzyme was advanced by 1 day.

Germination of Barley Grains Overexpressing Thioredoxin h

All operations were carried out at 25° C. (unless otherwise specified below) under conditions described by Kobrehel et al. 1992 and Lozano et al. 1996. Grains were surface sterilized by continuous stirring in 0.25% bleach for 30 min. Bleach was removed by extensive washing with sterilized distilled water. Thirty sterilized null segregant (GPdBhssBarWtrx-29-22-10, in which the transgene was removed by crossing with a self-polinated plant from the same line) and thirty sterilized homozygous (GPdBhssBarWtrx-29-3) seeds were placed In each of a series of plastic Petri dishes (12.5 cm diameter) fitted with three layers of Whatman #1 filter paper moistened with 15 ml sterile distilled water. Plates were wrapped with aluminum foil and grain was germinated in a dark chamber at 20° C. for up to 7 days. One plate was read at each time point shown in FIG. 21. Percent germination, in the first day (from the start of incubation up to 24 hours), was determined by observing the emergence of the radicle. On the subsequent days, percent germination represents seedling growth as determined by measuring the length of coleoptile and roots of the germinated grains.

Figure 21:
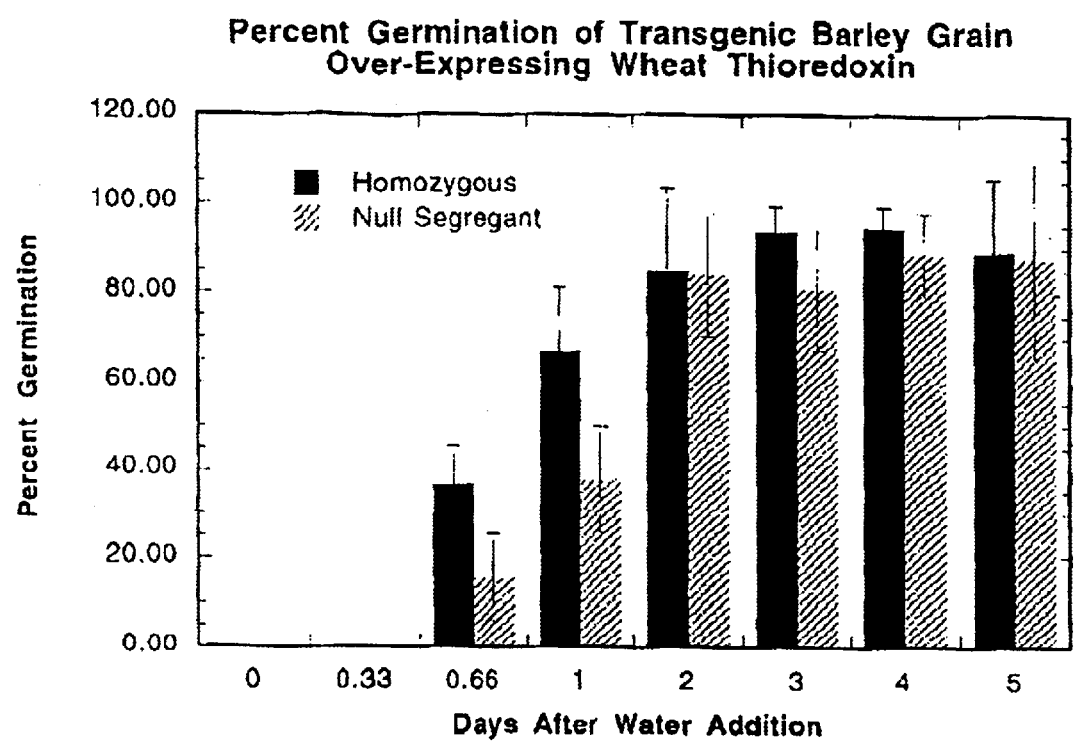
FIG. 21 shows the effect of overexpressed wheat thioredoxin h on the germination of null segregant and transgenic (homozygous) barley grains.

The results, shown in FIG. 21, indicate that germination in transgenic barley overexpressing wheat thioredoxin h is detected about 16 hours after the onset of incubation in about 25–30% of the seeds. In contrast, no germination in the null segregant was detected at 16 hours but is first detected 8 hours later, on Day 1. Therefore, in the transgenic germination is advanced about 8 hours. However, on Day 1 germination was detected in approximately 70% or about twice the number of transgenic grains in comparison to their null segregant counterparts. It is interesting to note that the onset of germination in the transgenics parallels the onset of the detection of alpha amylase as shown in FIG. 10.

Sequential Extraction of Grain Proteins from Transgenic Barley Grains.

Isolated endosperm from 10 dry grains or seedlings (germinated as described above) were ground with mortar and pestle at 4° C. with 3 ml Tris-HCl buffer as indicated below. The separate mixtures of homozygous GPdBhssBarWtrx-29-3 and null segregant GPdBhssBarWtrx-29-22-10 grains were placed in a 5-ml screw-top centrifuge tube. Grains were mechanically shaken for 30 minutes and then centrifuged for 10 min at 24,000×g. The supernatant fraction (buffer-soluble) was decanted and saved for analysis and the residue was extracted sequentially with the following solvents for the indicated times: [1] 0.5 M NaCl (30 min); [2] water (30 min) [3] 2×50% propanol (2 hr); [4] 2×50% propanol+2% 2-mercaptoethanol (MET) (2 hr); and [5] 0.5 M borate buffer, pH 10, containing 1% SDS and 2% 2-mercaptoethanol (2 hr). Supernatant fractions of all extracts were determined for volume and protein content (by Coomassie dye binding method), then were stored at −20° C. until use. By convention, the fractions are designated: [1] albumin/globulin (buffer/salt/water); [2] Hordein I (propanol); [3] Hordein II (propanol+MET); and [4] glutelin (Borate/SDS/MET) (Shewry et al., 1980). These fractions were used to determine, protein content, the distribution of proteins between the water soluble and insoluble fractions, the total extractable protein, and reduction with NADPH.

To determine the in vivo redox status of protein from transgenic barley grain during germination and seedling development, the extraction procedure was repeated except that 2 mM mBBr was included in the Tris grinding buffer and the grinding was under liquid nitrogen. The mBBr derivatized proteins were eletrophoresed on SDS-polyacrylamide gels (1.5 mm thickness, 10–20% gels, pH 8.5 (Laemmli, 1970). Gels were developed for 16 hr at a constant current of 8 mA Following electophoresis, gels were placed in 12% (w/v) trichloroacetic acid and soaked for 4 to 5 hr with one change of solution to fix the proteins; gels were then transferred to a solution of 40% methanol/10% acetic acid for 8 to 10 hr with agitation to remove residual mBBr. The fluorescence of mBBr (both free and protein bound mBBr), was visualized by placing gels on a light box fitted with an ultraviolet light source (365 nm). Following removal of the excess (free) mBBr, images of gels were captured by Gel Doc 1000 (Bio-Rad).

To ascertain the equivalent protein amount of loaded extracts, SDS-gels were stained with Coomassie Brilliant Blue G250 in 10% acetic acid for 30 min, and destained in 10% acetic acid for 30 min with the aid of a microwave oven. Protein stained gels were captured by Gel Doc 1000 as above.

The quantification of fluorescence (pixel×mm×mm) and protein (optical density×mm×mm) on gels were carried out by a software program for image analysis—Multi-Analyst, version 1.0 (Bio-Rad). Relative reduction was expressed as the ratio of fluorescence to protein.

The results of two experiments shown in Table 5, Table 6, and Table 7 demonstrate an increase in the total protein on a percent grain and a percent weight basis in the transgenic barley as compared to the null segregant. The transgenic have a thioredoxin content that is at least twofold higher (10–15 μg/mg soluble protein; 2–8 μg/gram tissue) than the null segregant. The data indicate that this increase in total extractable protein is the result in redistribution of the protein to the most soluble albumin/globulin fraction. The redistribution of the protein to the soluble fraction increase in the transgenics is at least 5% higher than the controls.

TABLE 5

Protein Content of Various Fractions in Transgenic Barley Grain Overexpressing Wheat Thioredoxin h Experiment I*

|  | Null Segregant | | Homozygous | |
| --- | --- | --- | --- | --- |
| Protein Fraction | mg/seed | mg/gram | mg/seed | mg/gram |
| Albumin/Globulin | 0.462 | 12.25 | 0.548 | 13.58 |
| Hordein I | 0.239 | 6.34 | 0.322 | 8.01 |
| Hordein II | 0.136 | 3.61 | 0.094 | 2.34 |
| Glutelin | 0.110 | 2.92 | 0.097 | 2.41 |
| Total Extractable Protein | 0.947 | 25.12 | 1.059 | 26.34 |

*Weight per 10 seeds is 0.377 and 0.402 full null segregant and homozygous line of transgenic barley

TABLE 6

Protein Content of Various Fractions in Transgenic Barley Grain Overexpressing Wheat Thioredoxin h Experiment II**

|  | Null Segregant | | Homozygous | |
| --- | --- | --- | --- | --- |
| Protein Fraction | mg/seed | mg/gram | mg/seed | mg/gram |
| Albumin/Globulin | 0.691 | 20.03 | 1.044 | 27.12 |
| Hordein I | 0.373 | 10.81 | 0.368 | 10.03 |
| Hordein II | 0.254 | 7.36 | 0.240 | 6.23 |
| Glutelin | 0.066 | 1.91 | 0.062 | 1.61 |
| Total Extractable Protein | 1.384 | 40.11 | 1.732 | 44.99 |

**Weight per 10 seeds is 0.377 and 0.402 for null segregant and homozygous line of transgenic barley

TABLE 7

Percent Increase of Extractable Protein in Homozygous Line

|  | %/grain basis | %/mass basis |
| --- | --- | --- |
| Experiment I | 12 | 4.9 |
| Experiment II | 25 | 12 |

Figure 22:
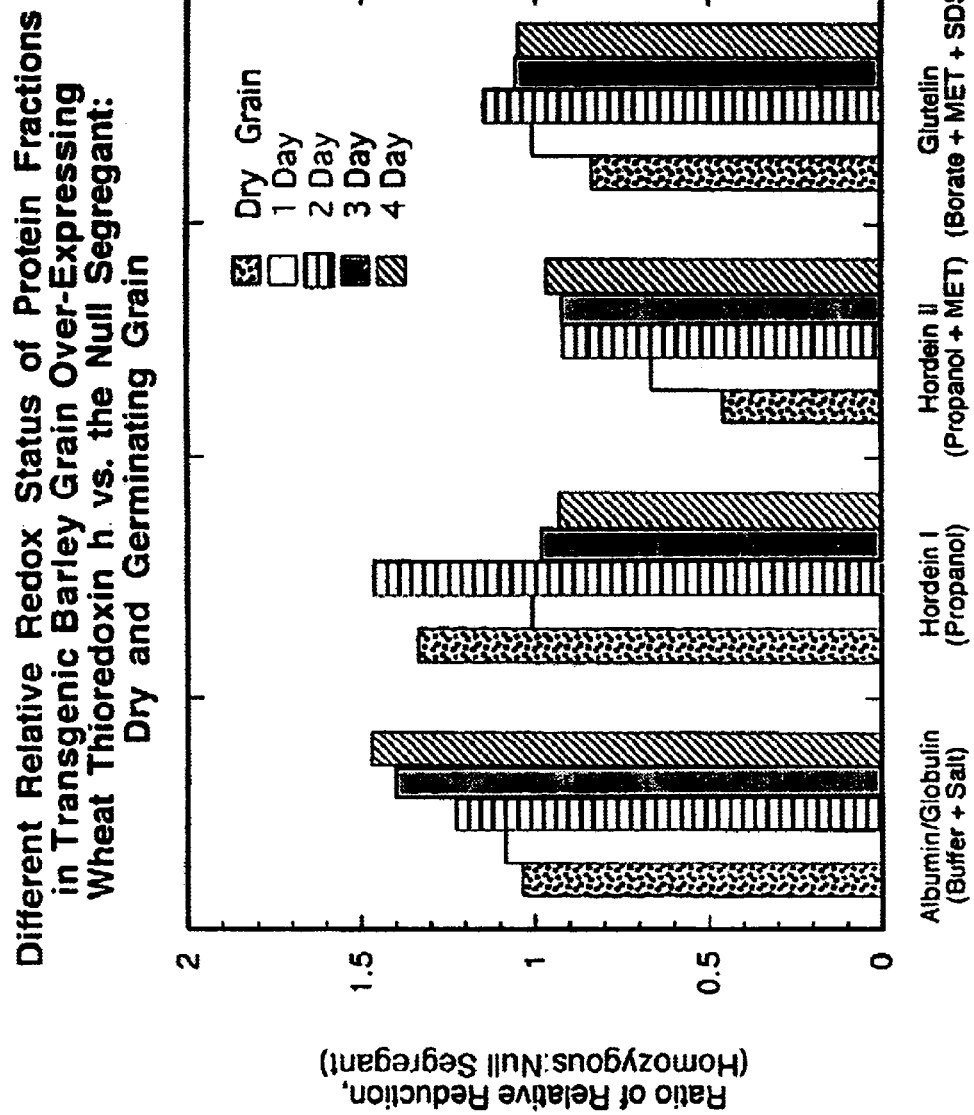
FIG. 22 shows the relative redox status of protein fractions in transgenic barley grain overexpressing wheat thioredoxin h in comparison to the null segregant in dry and germination grain.

Analysis of the relative redox status (SH:SS) of protein fractions in transgenic and null segregant barley grains during germination and as dry grains are shown in FIG. 22. In dry transgenic grain, the greatest increase in reduction relative to the null segregant was observed in the hordein I fraction. This increase was paralleled by decreases in the relative redox status in the hordein II and glutelin fractions while the relative redox status of the albumin/globulin fraction was unchanged. The relative redox status of the transgenic in comparison to the null segregant is at least 5:1.

During germination, the albumin/globulin fraction progressively increases, reaching a relative redox ratio of about 1.5 on Day 4. The relative redox status of the hordein II and glutelin fractions also increased during germination but only reached parity with the null segregant. In contrast the relative redox status of the hordein I fraction was highly variable.

According to the above example, other types of plants, are transformed in a similar manner to produce transgenic plants overexpressing thioredoxin, such as transgenic wheat, described below, rice, maize, oat, rye sorghum (described below), millet, triticale, forage grass, turf grass, soybeans, lima beans, tomato, potato, soybean, cotton, tobacco etc. Further, it is understood that thioredoxins other than wheat thioredoxin or thioredoxin h can be used in the context of the invention. Such examples include spinach h; chloroplast thioredoxin m and f, bacterial thioredoxins (e.g., *E. coli*) yeast, and animal and the like.

Example 2

Transgenic Wheat Grain Overexpressing Thioredoxin h and Arabidopsis NTR

A. Materials and Methods

Plant Materials

Spring cultivar of wheat, Bobwhite, Anza and Yecora Rojo, were grown in the greenhouse as described previously (Wan and Lemaux 1994; Lemaux et al. 1996). Ten- to 14-day-old germinating plants of a winter—wheat cultivar, Karl, were incubated at 4° C. for 45 to 60 days in the dark for vernalization treatment.

Wheat Expression Vectors

For wheat transformation, synthetic green fluorescent protein gene [sfgp(S65T)], wheat thioredoxin h (wtrxh) or Arabidopsis ntr expression vectors driven by barley endosperm-specific B$_1$- or D-hordein were constructed as follows:

(1) pDhSSsGFPN3–4: the chimeric DNA construct containing the D-hordein promoter-signal sequence-sgfp (S65T)-nos was obtained using a modified method of site-directed mutagenesis by PCR (Cho and Lemaux 1997). The three-primer strategy was used. A shorter fragment of 0.5-kb DHORSS was produced by PCR in the first reaction using primers, Dhor4 (5'-agaaagcttggtaccCTTCGAGTGCCCGCCGAT-3'; SEQ ID NO:9) and DhorSSsGFP1 R (5'-AACAGCTCCTCGCCCTTGCTCA CAGCGGTGGTGAGAGCCACGAGGGC-3'; SEQ ID NO:10), with the template pHor3-1 containing a genomic clone of D hordein (Sørensen et al., 1996), and this first PCR product (megaprimer) was diluted 50 times. DhorSSsGFP1R is an overlapping primer which contain the sgfp(S65T) coding sequence and a partial signal peptide sequence (underlined) from the D-hordein promoter. For the second PCR reaction, five μl of the diluted megaprimer (DHORSS), twenty ng of template (pAct1IsGFP-1; Cho et al., 2000) and 40 pmol of external primers [Dhor4 and Nos1R (5'-cggaattcGATCTAGTMCATAGATGACA-3': SEQ ID NO:17)] were mixed to a final volume of 100 μl in 1×PCR buffer; pAct1IsGFP-1 contains synthetic gfp gene [sgfp(S65T)] (Chiu et al., 1996) controlled by the rice actin 1 promoter and its intron and terminated by nos. The resulting chimeric PCR product was digested with HindII and EcoRI and ligated into the HindII/EcoRI-digested pBluescript II KS(+) vector, further confirmed by DNA sequencing of the PCR-amplified fragment [D-hordein promoter with its signal peptide sequence plus the junction region with the 5' sgfp(S65T)], and used for stable transformation of wheat.

(2) pDhWTRXhN-2: the 384-bp wtrxh coding region was amplified by PCR utilizing the plasmid pTaM13.38 (Gautier et al., 1998) containing cDNA clone of wtrxh gene as a template to create XbaI and SacI sites with primers Wtrxh1 (5'-atatctagaATGGCGGCGTCGGCGGCGA-3'; SEQ ID NO:5) and Wtrxh2R (5'-atagagctc TACTGGGCCGCGTGTAG-3'; SEQ ID NO:6), respectively (FIG. 12); small letters contain a restriction enzyme site for subcloning of the DNA construct containing the wtxh gene and underlined letters indicate the wrtxh sequences. The ATG initiation codon for wtrxh expression was included in the Wtrxh1 primer. PCR reactions were performed on a thermocycler (MJ Research Inc., Watertown, Mass.) using recombinant Taq DNA polymerase (Promega, Madison, Wis.) in a 100-μl reaction volume. The reaction buffer contained 10 mM Tris-HCl (pH 9.0), 50 mM KCl, 1.5 mM MgCl$_2$, 0.1% Triton-X-100, and 50 μM of each deoxyribonucleoside triphosphate. PCR conditions were 25 cycles of 94° C. for 1 min, 55° C. for 1 min and 72° C. for 2 min, with a final extension step at 72° C. for 7 min. The wtrxh fragment amplified with primers Wtrxh1 and Wtrxh2R was purified from a 0.7% agarose gel using QIAquick® gel extraction kit (Qiagen Inc., Chatsworth, Calif.), digested with XbaI and SacI and ligated into XbaI/SacI digested pUC19 to generate the pWTRXh-1 plasmid. Nucleotide sequences of the PCR-amplified wtrxh coding region were determined by dideoxynucleotide chain termination method using Sequenase according to manufacturers instructions (United States Biochemical, Cleveland, Ohio) with double-stranded plasmid templates and regularly spaced primers. pDhWTRXN-2 was made by replacing the uidA gene in pDhGN-2 (containing barley endosperm-specific D-hordein promoter and nos 3' terminator; M. -J. Cho, unpublished) with the XbaI/SacI fragment containing wtrxh coding sequence from the pWTRXh 1.

Figure 12:
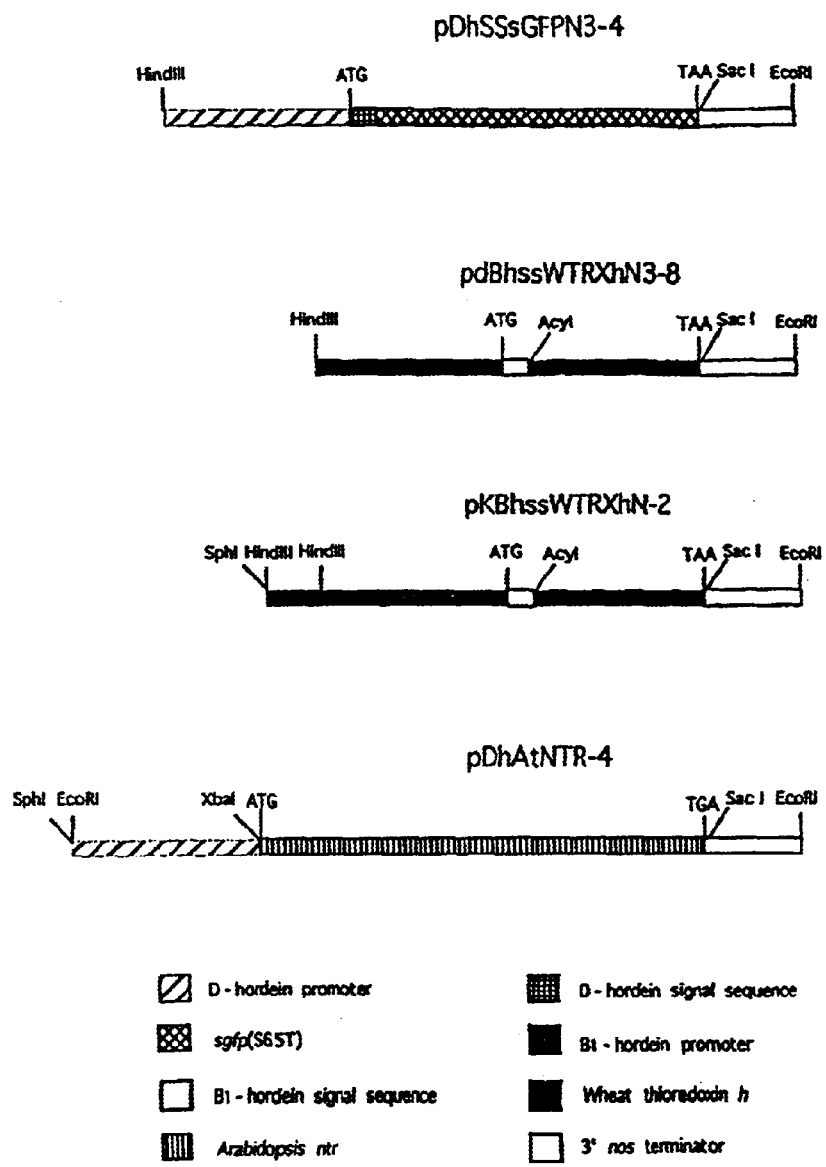
FIG. 12 depicts the DNA constructs used for wheat transformation.

(3) pdBhssWTRXhN3-8: primers Bhor7 (5'-GTAAAGCTTTAACAACCACACATTG-3'; SEQ ID NO:7) and BhorWtrxh1 R (5'-CCGACGCCGCTGCMTCGTACTTGTTGCCGCMT-3'; SEQ ID NO:8) containing HindIII and AcyI sites, respectively, were used for amplification of 0.49kb B$_1$-hordein 5' region including the B$_1$-hordein signal peptide sequence using the λ2-4/HindIII plasmid containing genomic clone of B$_2$hordein (Brands et al., 1985; Cho et al., 1997) as a template. The primer BhorWtrxhIR is an overlapping primer containing the wtrxh coding sequence (underlined) and a partial signal peptide sequence from the B$_1$-hordein promoter without the ATG initiation codon for wtrxh. pdBhssWTRXhN3-8 was made by replacing the D-hordein promoter in pDhWTRXN-2 with the 0.49-kb PCR-amplified HindIII/AcyI fragment containing B$_1$-hordein promoter with its signal peptide sequence plus the junction region with the 5' wtrxh. Thus, construct pdBhWTRXN3-8 contains the barley endosperm-specific B$_1$-hordein promoter with its signal peptide sequence, wtrxh and nos (FIG. 12). The signal peptide sequence containing the ATG initiation codon was directly combined with the sequence of the wtrxh gene (Gautier et al., 1998), without having extra amino acid sequences between the two, in order to make WTRXh, protein provide a precise cleavage site in the lumen of endoplasmic reticulum (ER). The PCR-amplified fragment of the chimeric product was confirmed by DNA sequencing.

(4) pKBhssWTRXN-2:pBhor-1 was digested with SphI and SacI in order to obtain the 0.55-kb 5'-flanking region of B$_1$-barley hordein promoter. The 0.55 kb SphI/SacI fragment was ligated into pSPORT 1 (GIBCO BRL, Gaithersburg, Md.) to make pSPBhor4. pdBhssWTRXN3-8 was digested with HindIII/EcoRI and the HindIII/EcoRI fragment containing the 0.43-kb barley endosperm-specific B$_1$-hordein promoter plus its signal peptide sequence, wtrxh and nos was ligated into the HindIII/EcoRI-digested pSPBhor-4 to generate the pSPBhssWTRXN-4 plasmid. In order to remove ampicillin resistance gene, the 1.3-kb SphIEcoRI fragment of pSPBhssWTRXN4 was ligated into SphIEcoRI-digested pJKKmf(−) containing kanamycin resistance gene to form pKBhssWTRXN-2. Thus, the kanamycin-backbone construct pKBhssWTRXN-2, contains the 0.55-kb 5'-flanking region of the B$_1$-barley hordein promoter plus its signal pepbde sequence, wtrxh and nos (FIG. 12).

(5) pDhAtNTR-4: pDhAtNTR-4 was made by replacing the wtrxh gene in pDhWTRXN-2 (described above) with the PCR-amplifled XbaI/SacI fragment containing Arabidopsis ntr coding sequence from pAtNTR (a gift from Dr. S. Y. Lee). Primers, AtNTR1 (5'-ggtctaga ATGGAAACTCACAAAACC-3'; SEQ ID NO:18) and AtNTR2R (5'-gggagctcTCAATCACTCTTACCCTC-3'; SEQ ID NO:20), were used for amplification of the 1.009-Kb XbaI/SacI fragment containing 0.993 Kb Arabidopsis ntr coding sequence; small leters contain a restriction enzyme site for subcloning of the DNA construct containing Arabidopsis ntr gene and underlined letters indicate the Arabidopsis ntr sequences. The Arabidopsis ntr fragment was purified from a 0.7% agarose gel using QIAquick® gel extraction kit, digested with XbaI and SacI and ligated into XbaI/SacI—digested pDhWTRXN-2 to generate the pDhAtNTR-4 plasmid. Nucleotide sequences of the PCR-amplified Arabidopsis ntr coding region were determined by DNA sequencing.

Stable Wheat Transformation

Stable transgenic lines of wheat transformed with pDhSSsGFPN3-4, pdBhssWTRXhN3-8, pKBhssWTRXN-2 or pDhAtNTR4 were obtained using highly regenerative, green tissues as transformation targets. Highly regenerative tissues have a high percentage of totipotent cells capable of sustained cell division and competent for regeneration over long period. In order to induce highly regenerative green tissues, whole immature embryos (IEs; 1.0–2.5 mm) were aseptically removed, placed scutellum side down on DBC3 medium (callus-induction medium containing 1.0 mg/L 2,4-dichlorophenoxyacetic acid, 0.5 mg/L BAP and 5.0 $\mu$M $CuSO_4$; Cho et al., 998a–c). Five to 7 days after initiation, germinating shoots and roots were removed by manual excision. After 3 weeks of incubation at 24±1° C. under dim light conditions (approximately 10 to 30 $\mu$E, 16 h-light), highest quality tissues from the scutellum was selected and maintained on DBC3 medium. Attentively, highly regenerative, green tissues were obtained from daughter tissues, oval-shaped tissues with highly embryogenic structures which were emerged at the base of germinating shoots or from the outside layer of the tissues near the base of germinating shoots. Seven to 14 days after initiation, daughter tissues (2–4 mm in length) were isolated from germinating IEs by manual excision and transferred to fresh DBC3 medium. After an additional 3- to 4-week incubation, the tissues were selected again, broken into 2 to 4 pieces of about 3 to 5 mm in size and transferred onto fresh medium. The tissues were maintained on fresh medium, subculturing at 3- to 4-week intervals.

Only good quality tissues were selected for bombardment. The highly regenerative tissues (preferably about 3 to 4 mm in size) were transferred for osmotic pretreatment to DBC3 medium containing equimolar amounts of mannitol and sorbitol to give a final concentration of 0.4 M Four hours after treatment with the osmoticum, the tissues were bombarded as previously described (Wan and Lemaux 1994; Lemaux et al. 1996). Gold particles (1.0 $\mu$m) were coated with 25 $\mu$g of a 1:1 or 1:2 molar ratio of a mixture of pact1IHPT-4 (or pUbiINPTII-1) and and one of 4 plasmids, pDhSSsGFPN3-4, pdBhssWTRXhN3-8, pKBhssWTRXN-2 or pDhAtNTR4, followed by bombardment using a PDS-1000 He biolisfic device (Bio-Rad, Inc., Hercules, Calif.) at 600 or 900 psi. The plasmid pAct1 IHPT4 contains the hygromycin phosphotransferase (hpt) coding sequence under control of the rice actin 1 promoter (Act1), its intron and the nos 3' terminator (Cho et al., 1998 a–c). pUbiINPTII-1 contains the neomycin phosphotransferase (nptII) gene under control of the maize ubiquitn promoter and first intron and terminated by nos. Sixteen to 18 hr after bombardment, the bombarded tissues were placed to DBC3 medium without osmoticum and grown at 24±1° C. under dim light.

Following the initial 10- to 14-day culturing period, each regenerative tissue was broken into 1 to 3 pieces depending on tissue size and transferred to DBC3 medium supplemented with 20–25 mg/L hygromycin B (Boehringer Mannheim, Mannheim, Germany) for selection for hpt or 30 mg/L G418 (Sigma, Saint Louis, Mo.) for nptII. Three weeks after the first round of selection, the cultures were transferred to fresh DBC3 medium containing 30 mg/L hygromycin B or 40 mg/L G418. From the third round selection, the tissues were subcultured and maintained on DBC3 medium containing 30 mg/L hygromycin B or 40 mg/L G418 at 3 to 4-week intervals. After the fourth or Fifth round of selection, surviving tissues were transferred to DBC3 medium without selective agent. Following the identification of green tissues with sufficient regenerative structures on DBC3, the tissues were plated on solid regeneration medium without selective agent and exposed to higher intensity light (approximately 45–55 $\mu$E). After four weeks on regeneration medium (callus-induction medium without phytohormones), the regenerated shoots were transferred to Magenta boxes containing the same medium without selective agent. When the shoots reached the top of the box plantlets were transferred to the soil.

Polymerase Chain Reaction (PCR) and DNA Hybridization

Total genomic DNA from leaf tissues was purified as described (Dellaporta, 1993). To test for the presence of wtrxh in genomic DNA of putatively transformed lines, 500 ng of genomic DNA was amplified by PCR using either of two primer sets, Wtrxh1 (5'-ATATCTAGAATGGCGGCGTCGGCGGCGA-3'; SEQ ID NO:5) and Wtrxh2R (5'-ATAGAGCTCTTACTGGGCCGCGTGTAG-3'; SEQ ID NO:6) or Wtrxh4 (5'-CCAAGAAGTTCCCAGCTGC-3'; SEQ ID NO:11) and Wtrxh5R (5'-ATAGCTGCGACMCCCTGTCCTT-3'; SEQ ID NO:19). The presence of hpt and nptII was tested by using each of the primer sets, $HPT_6F$ (5AAGCCTGAACTCACCGCGACG3'; SEQ ID NO:21) plus HPT5R (5'-AAGACCAATGCGGAGCATATAC-3': SEQ ID NO:22) (Cho et al., 1998a–c) and NPT1F (5'-CMGATGGATTGCACGCAGGTTCT-3'; SEQ ID NO:15) plus NPT2R (5'-ATAGAAGGCGATGCGCTGCGAAT-3'; SEQ ID NO:16). Amplifications were performed with Taq DNA polymerase (Promega, Madison, Wis.) in a 25 $\mu$l reaction (Cho et al., 1998a–c). Twenty-five $\mu$l of the PCR product with loading dye was electrophoresed on a 1.0% agarose gel with ethidium bromide and photographed using exposure to UV light Presence of 0.4- and 0.14 kb fragments was consistent with an intact and truncated wtrxh fragments, repectively; 0.81-kb hpt and 0.76-kb nptII fragments for the pAct1HPT-4 and pUbiINPTII-1 plasmids, were produced with hpt and nptII primers, respectively. Homozygous lines for wtrxh were screened using $T_1$, $T_2$ or $T_3$ plants by PCR anlaysis.

GFP Expression Detection by Fluorescence Microscopy

GPF expression was monitored at higher magnification using a Nikon Microphot-5A fluorescent microscope equipped with a Nikon B-2A filter block containing a 450–490 excitation filter and a BAS20 emission barrier filter (Cho et al., 2000).

Western Blot Analysis

Western blot analysis was performed on seeds from selected transgenic wheat lines as well as from control counterparts grown under the same conditions. Thioredoxin h purified from seeds of a bread wheat cultivar, cv. Capitole, was used as a reference. Whole seeds were ground to a fine powder with a mortar and pestle under liquid nitrogen. Ten seeds were used for each sample; the volume of extraction buffer [50 mM Tris HCl or phosphate buffer, pH 7.8, 0.5 mM phenylmethyl sulfonyl fluoride (PMSF), 1 mM EDTA] varied from 2 to 4 ml depending on the number of seeds used and the viscosity of the extract. Grinding was continued for an additional min after buffer addition, the preparation was centrifuged at 14,000×g for 10 min and the supernatant solution was saved as the soluble (albumin-gobulin) fraction. SDS-PAGE of the soluble fraction was performed in 12–17% polyacrylamide gradient gels at pH 8.5 (Laemmli, 1970). Equal amounts of protein (40 $\mu$g) of each sample quantitated according to Bradford (1976) were diluted 1:2 v/v in Laemmli sample buffer, boiled for 3 minutes, loaded onto gels and subjected to electrophoresis at a constant current of 15 mA. Proteins were transferred to nitrocellulose at a constant voltage of 40 V for 4 hours at 4° C. using a Hoefer Transphor Transfer Unit (Alameda, Calif.) (all at 25° C.). Nitrocellulose was blocked with 5% powdered milk in TBS for 2 hours, incubated in primary antibody for 4 hours and in secondary antibody for 1 hour. The primary antibody was wheat anti-thioredoxin h II (Johnson et al., 1987b) diluted 1 to 500; secondary antibody was goat anti-rabbit alkaline phosphatase (Bio-Rad, Hercules, Calif.) diluted 1:3000. Blots were developed in NBT/BCIP alkaline phosphatase color reagent (Bio-Rad, Hercules, Calif.). Images were scanned using a Bio-Rad GelDoc 1000 (Hercules, Calif.) and analyzed using Bio-Rad Multi Analyst, version 1.0.2.

B. Results and Discussion

Construction of Expression Vectors

To overexpress sGFP(S65T), WTRXh and AtNTR in wheat seed, five expression constructs containing wtrxh driven by endosperm-specific hordein promoters, pDhSSsGFPN3-4, pDhWTRXN-2, pdBhssWTRXhN3-8, pKBhssWTRXN-2 or pDhAtNTR-4, were made. Out of five constructs, four (pDhSSsGFPN3-4, pdBhssWTRXhN3-8, pKBhssWTRXN-2 or pDhAtNTR4; FIG. 12) were used for stable transformation of wheat.

Production of Transgenic Plants

Highly regenerative tissues (at least 1 tissue, preferably 50, and most preferably 500 of 3–4 mm in length) were bombarded and cultured on DBC3 medium for the first 10 to 14 days in the absence of selection. For the second transfer (1st round selection), selection was on DBC3 medium supplemented with 25–30 mg/L hygromycin B for hpt selection or 30 mg/L G418 for nptII selection. At the second round selection, DBC3 medium with 30 mg/L hygromycin B or 40 mg/L G418 was used. From the 4th transfer (3rd round selection) onward, the selection pressure was maintained at the same level. In general, hygromycin- or G418-resistant tissues with some green sectors were observed at the third round selection. Putative transgenic calli with green sectors were maintained and proliferated on the same medium without selective agent from after the fourth or fifth round of selection, until the green sectors formed fully developed regenerative structures. Green regenerative tissues were regenerated on regeneration medium and the plantlets transferred to soil approximately 3 to 4 weeks after growth on the same medium of the Magenta boxes. To date using this transformation protocol, we obtained two independent Bobwhite lines, four transgenic Anza lines, two transgenic Yecora Rojo lines transformed with pdBhssWTRXhN3-8, one Bobwhite line transformed with pKBhssWTRXN-2 and one Yecora Rojo line transformed with pDhAtNTR4 (Table 8). We also obtained two independent Bobwhite lines transformed with pDhSSsGFPN3-4 (data not shown).

Endosperm-Specific Expression of Barley Hordein Promoter In Transgenic Meat

Figure 13:
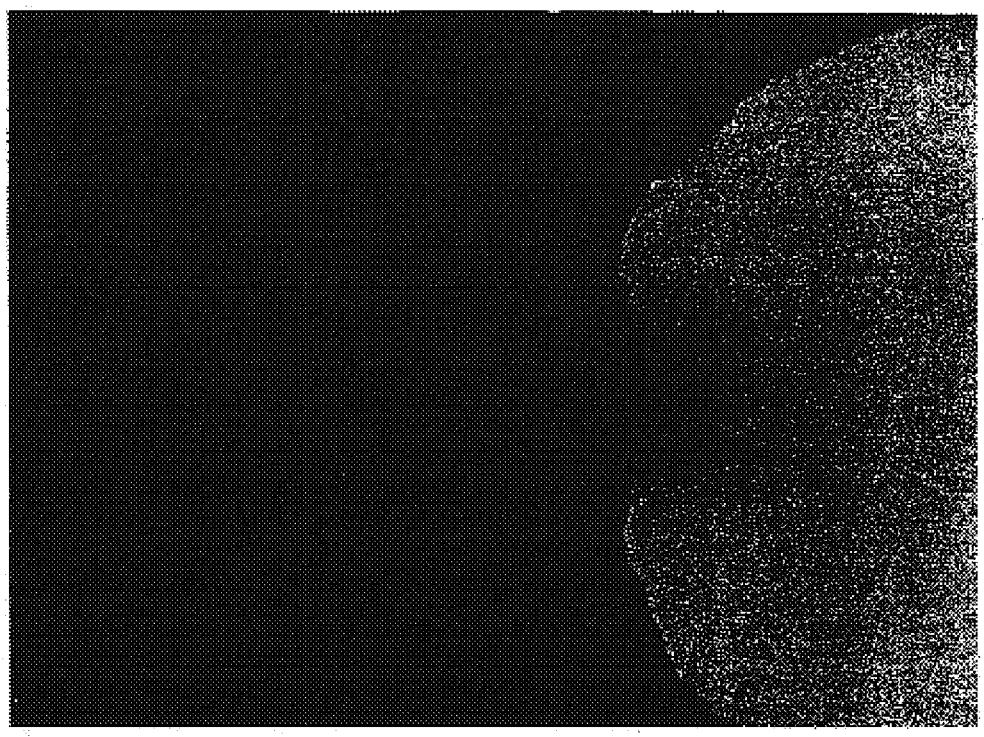
FIG. 13 shows the endosperm-specific expression of barley D-hordein promoter sgfp(S65T) in transgenic wheat plants. Transgenic endosperm is at the right, transgenic embryo is at the left.

Expression of GFP driven by barley D-hordein promoter was found specifically in the endosperm tissue of developing wheat grains; GFP expression was not observed in immature embryo tissues (FIG. 13).

Analysis of $T_0$ Plants and Their Progeny

Figure 14:
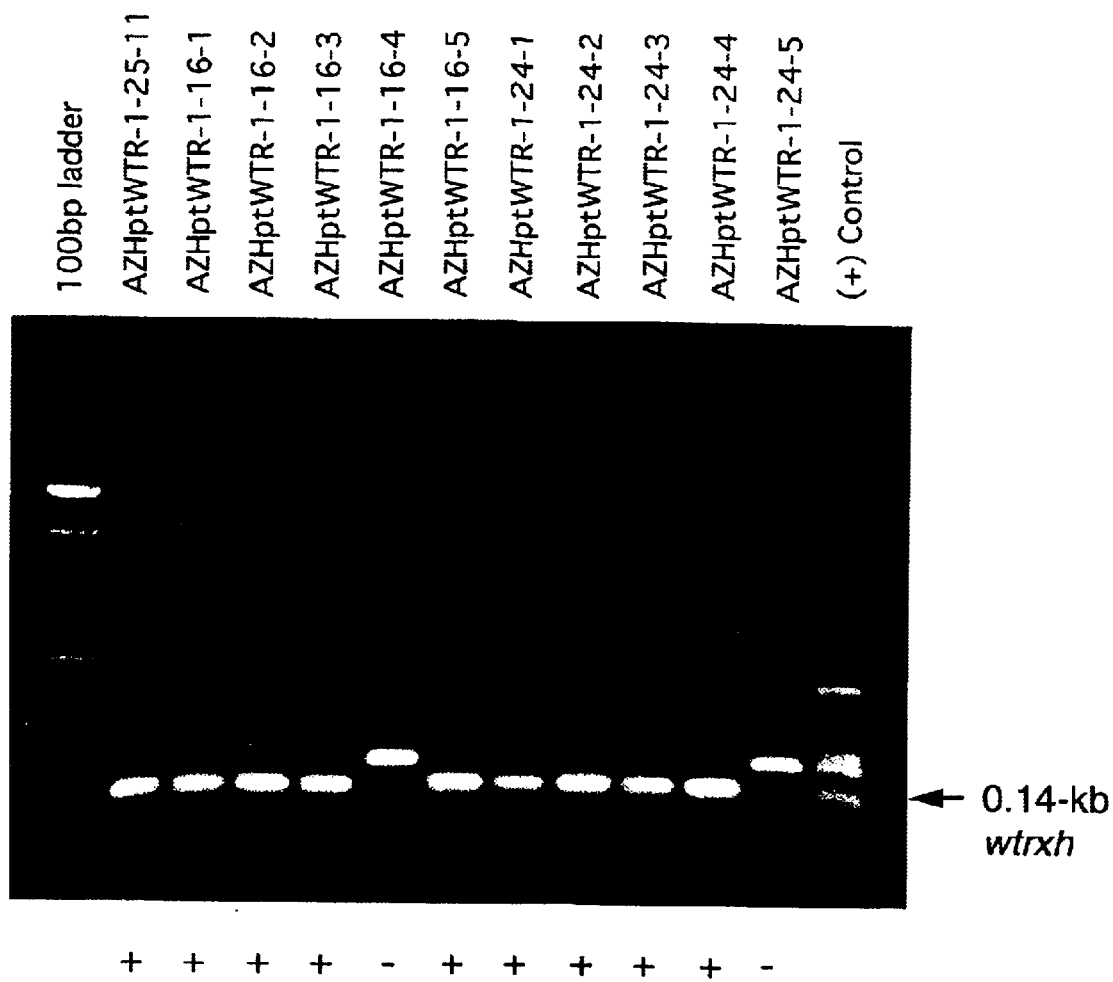
FIG. 14 shows the PCR analysis of genomnic DNA from transgenic wheat plants.

PCR analysis was performed using two sets of WTRXh primers and one set of AtNTR primers. PCR amplification resulted in 0.4-kb intact wtrxh or 0.14-kb truncated wtrxh (FIG. 14) and 0.5-kb internal Atntr fragments from transgenic lines. Seeds of $T_1$ and their progeny from some wtrxh-positive lines were planted in order to screen homozygous lines. Homozygous lines and null segregants were obtained from AZHptWTR-1, AZHptWTR-21 and YRHptWTR-1 (Table 8). Other lines are currently being screened for homozygous lines.

Characterization of Wheat Thioredoxin h Produced in Transgenic Grain

Figure 15:
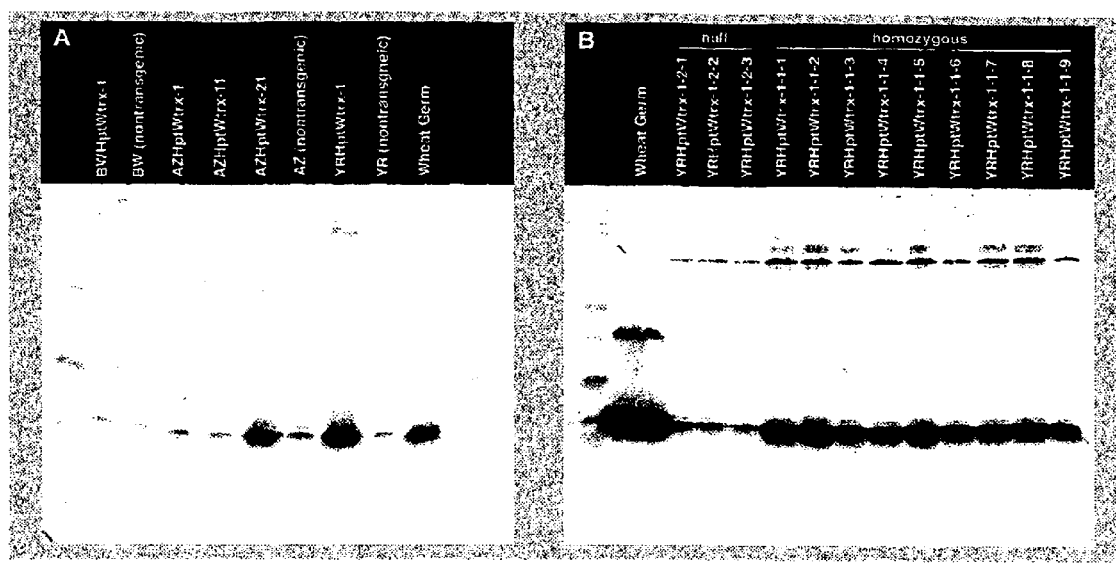
FIG. 15A–B shows wheat thioredoxin h-overexpressing wheat lines screened by western blot analyses. Panel A: $T_0$ wheat lines. Panel B $T_3$ homozygous line.

Of the stably transformed lines that expressed wheat thioredoxin h, on average, its level was found to be higher in transformants. Western blot analysis of soluble protein fractions from heterozygous mixtures of seeds from three of these lines, AZHptWTR-1, AZHptWTR-21 and YRHptWTR-1, showed approximately 5 times, 20 times, and 30 times more thioredoxin h, respectively, than nontransformed control grain (FIG. 15A). The thioredoxin content of the null segregant (YRHptWTR-1-2-1 to -3) was similar to that of the corresponding, nontransformed control (FIG. 15A and B).

TABLE 8

Summary of Transformation Experiments for Three Wheat Cultivars: Bobwhite Anza and Yecora Rojo

| Cultivars/Plasmids for bombardment | Transgenic wheat lines | DNA PCR ($T_0$ leaf) | | | WTRXh or NTR expression in $T_1$ seeds | Comments |
|---|---|---|---|---|---|---|
| | | hpt | wtrx | ntr | | |
| BW/pAct1IHPT-4 + pdBhssWTRXhN3-8 | BWHptWTR-1 | + | + | | n.d. | |
| | BWHptWTR-3 | + | − | | n.d. | |
| | BWHptWTR-4 | + | + | | n.d. | |
| | BWHptWTR-5 | + | − | | n.d. | |
| AZ/pACT1IHPT-4 + pdBhssWTRXhN3-8 | AZHptWTR-1 | + | + | | + | homozygous |
| | AZHptWTR-11 | + | + | | + | |
| | AZHPtWTR-13 | + | + | | n.d. | |
| | AZHptWTR-21 | + | + | | + | homozygous |
| YR/pACT1IHPT-4 + pdBhssWTRXhN3-8 | YRHptWTR-1 | + | + | | + | homozygous |
| | YRHptWTR-2 | + | − | | n.d. | |
| | YRHptWTR-8 | + | + | | n.d. | |
| BW/pUbilNPTII-1 + pKBhssWTRN-2 | BWNptBhWTR-10 | + | + | | n.d. | |
| YR/pAct1IHpt-4 + pDHAtNTR-4 | YRHptAtNTR-1 | + | | + | n.d. | |

BW, AZ and YR represent Bobwhite, Anza, Yocora Rojo, respectively
n.d.: not determined

Example 3

Effect of Thioredoxin Reduction on Digestion of Wheat Glutenins by Trypsin and Pancreatin Sequential Extraction of Grain Proteins from Transgenic Wheat Grains Transgenic grain (YRHptWTR-1-1) and null segregant (YRHptWTR-1-2) grain were ground with a coffee grinder at room temperature. Ground powder from 10 grams of each line was placed in a 250 ml screw-top centrifuge bottle and 60 ml of each extraction solution indicated below was added. The mixture was shaken mechanically and then centrifuged for 30 min at 5,000×g. The supernatant faction was decanted and saved for analysis, and the residue was mixed with the next solution. The powdered grain was extracted sequentially with the following solvents for the indicated times: [1] 2×0.5 M NaCl (30 min), [2] 2×70% ethanol (2 hr); [3] 2×0.1 M acetic acid (2 hr). Supernatant fractions of all extracts were analyzed for protein by the Coomassie dye binding method (Bradford, 1976) and then were stored at −20° C. until use. By convention, the fractions are designated: [1] albumin/globulin (water/salt-water); [2] gliadin (ethanol); and [3] glutenin (acetic acid) (Kruger et al., 1988; Shewry et al., 1986). These fractions were used for digestion and skin tests in Example 5, below.

Digestion of Glutenins

For reduction of glutenins extracted as above from non-transgenic green house plants, 4.2 $\mu$g NTR, 2.4 $\mu$g thioredoxin (both from $E.\ coli$), and 1 mM NADPH were added to 240 $\mu$g of target protein and incubated in a 37° C. water bath for 45 minutes. NTS (NTR/thioredoxin/NADPH) treated and untreated glutenins were incubated in 100 $\mu$l of simulated intestinal fluid (SIF) (Board of Trustees (ed.), 1995, Simulated Gastric Fluid, TS., pp 2053, The United States Pharmacopeia, 23, The National Formulary 18, United States Pharmacopeial Convention, Inc., Rockville, Md.) as described below. SIF contained 5 $\mu$g trypsin (or 20 $\mu$g pancreatin), 48.9 mM monobasic potassium phosphate, and 38 mM sodium hydroxide. After addition of the enzyme, the pH was brought to 7.5 with 0.2 M sodium hydroxide. Digests were incubated in a 37° C. water bath for 0, 20, 60, or 80 minutes. To stop the reaction, 100 mM PMSF and leupeptin (1 $\mu$g/ml) was added for trypsin digests and 1 N HCl for pancreatin digests. SDS-PAGE analysis of the digested samples was performed in 8–16% gradient gels as described by Laemmli (1970). Gels of 1.5 mm thickness were developed for 16 hr at a constant current of 7 mA SDS gels were stained with Coomassie brilliant blue R-250 in 10% acetic acid for 30 min, and destained in 10% acetic acid for 30 min with the aid of a microwave oven. Protein stained gels were captured by Gel Doc 1000. The quantification of protein (optical density×mm×mm) on the gels was carried out with a software program for image analysis-Multi-Analyst, version 1.0 (Bio-Rad). Relative digestion was expressed as the percentage of zero time undigested protein.

Figure 16:
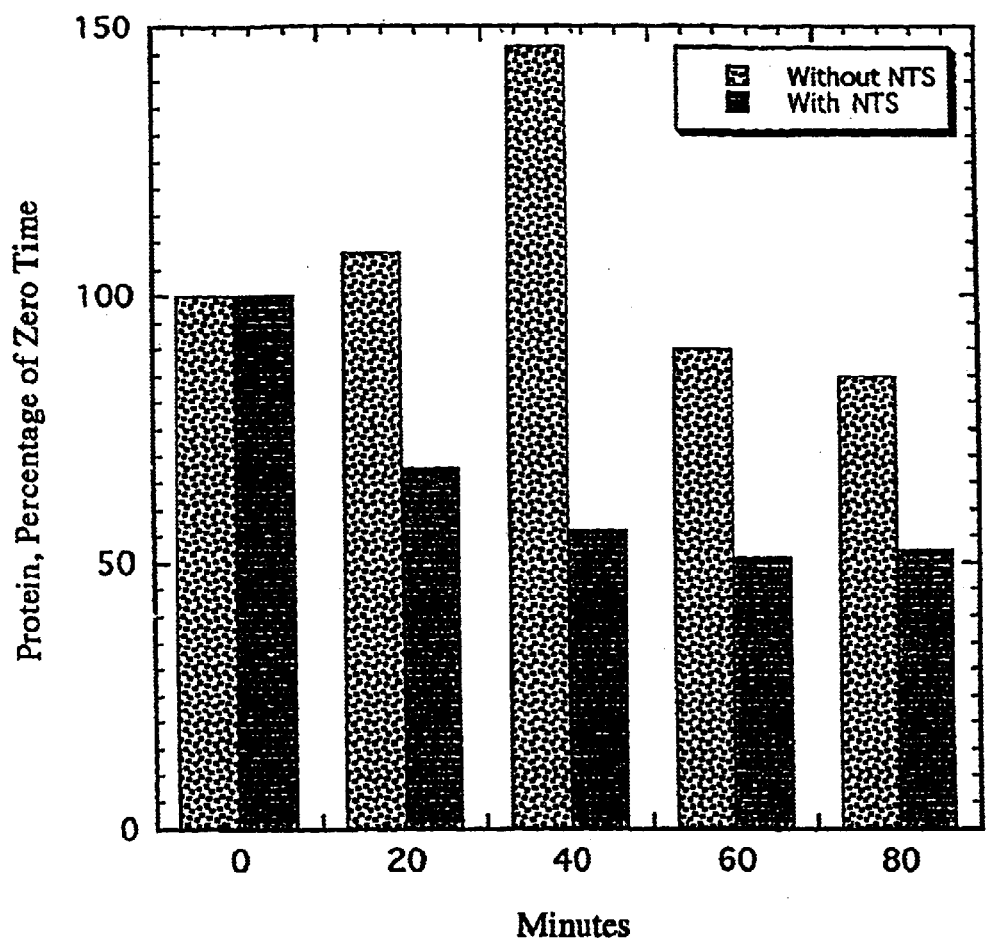
FIG. 16 shows the effect of thioredoxin reduction on digestion of wheat glutenins by trypsin.
Figure 17:
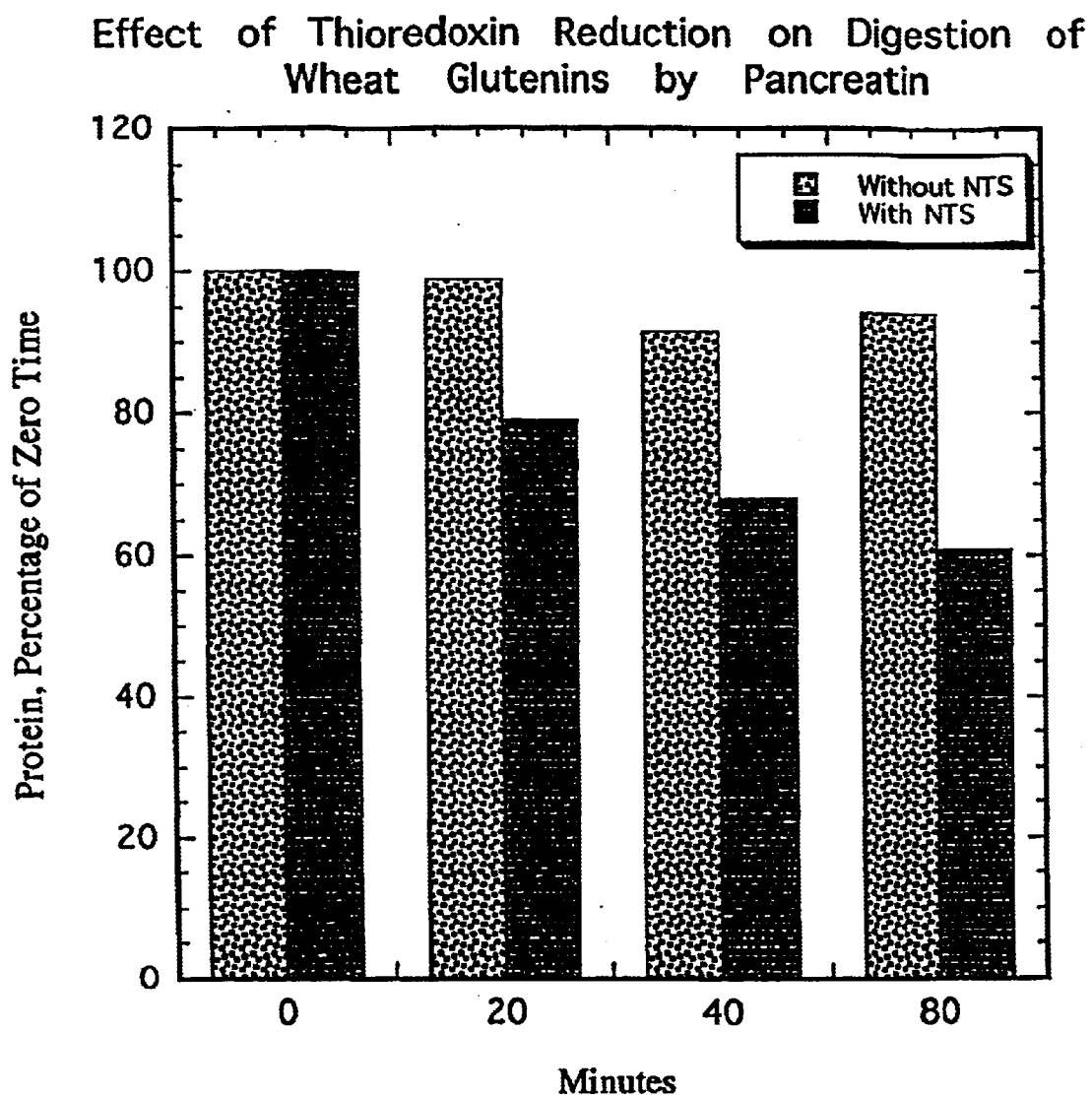
FIG. 17 shows the effect of thioredoxin reduction on digestion of wheat glutenins by pancreatin.

The results shown in FIGS. 16 and 17 demonstrate that thioredoxin reduction results in enhanced susceptibility of glutenins to protease digestion by trypsin and pancreatin, respectively. The most pronounced effects were observed with trypsin where about 55% of protein remained at 60 minutes post-digestion in the NTS treated sample in comparison to about 90–95% of the starting protein remained in the non-NTS treated sample. In the trypsin digestions, proteolysis progressed for 60 minutes and apparently plateaued. In the pancreatin digests, proteolysis progressed less rapidly. At 80 minutes post-pancreatin treatment, about 60% of the starting proteins remained in the NTS treated sample in comparison to 95% protein remaining in the non-NTS sample. Thus the transgenic grains of the present invention are more susceptible to digestion and are hyperdigestible. The increase in the digestibility is at least 5% in the transgenic plants in comparison to the non-transgenic grains.

Example 4

Effect of NTR on the Reduction of Proteins in Extracts of Wheat Grains Overexpressing Thioredoxin h In vitro Reduction of Proteins by NADPH or NTR or NADPH & NTR Aliquots of the albumin/globulin fraction from the homozygous lines overexpressing thioredoxin h as described in Example 2 and null segregant lines were used. The reaction was carded out in 30 mM Tris-HCl buffer, pH 7.9. As indicated the treatments were: (i) control, (ii) 1.25 mM NADPH, (iii) 3.0 $\mu$g Arabidopsis NTR, (iv) NADPH & NTR combined, and (v) 5 mM dithiothreitol (DTT). The above reagents were added to 70 microliters of this buffer containing 60 $\mu$g of protein. Total reduction by dithiothreitol (DTT) was achieved by boiling for 5 min. After incubation for 60 min at 37° C., 100 nmoles of mBBr were added and the reaction was continued for another 15 min at room temperature. To stop the reaction and derivative, excess mBBr, 10, $\mu$l of 100 mM MET was added. The reduced samples, after adding 25 $\mu$l of 4×Laemmli sample buffer, were analyzed as described by mBBr/SDS-PAGE (Kobrehel, K. et al. 1992).

Figure 18:
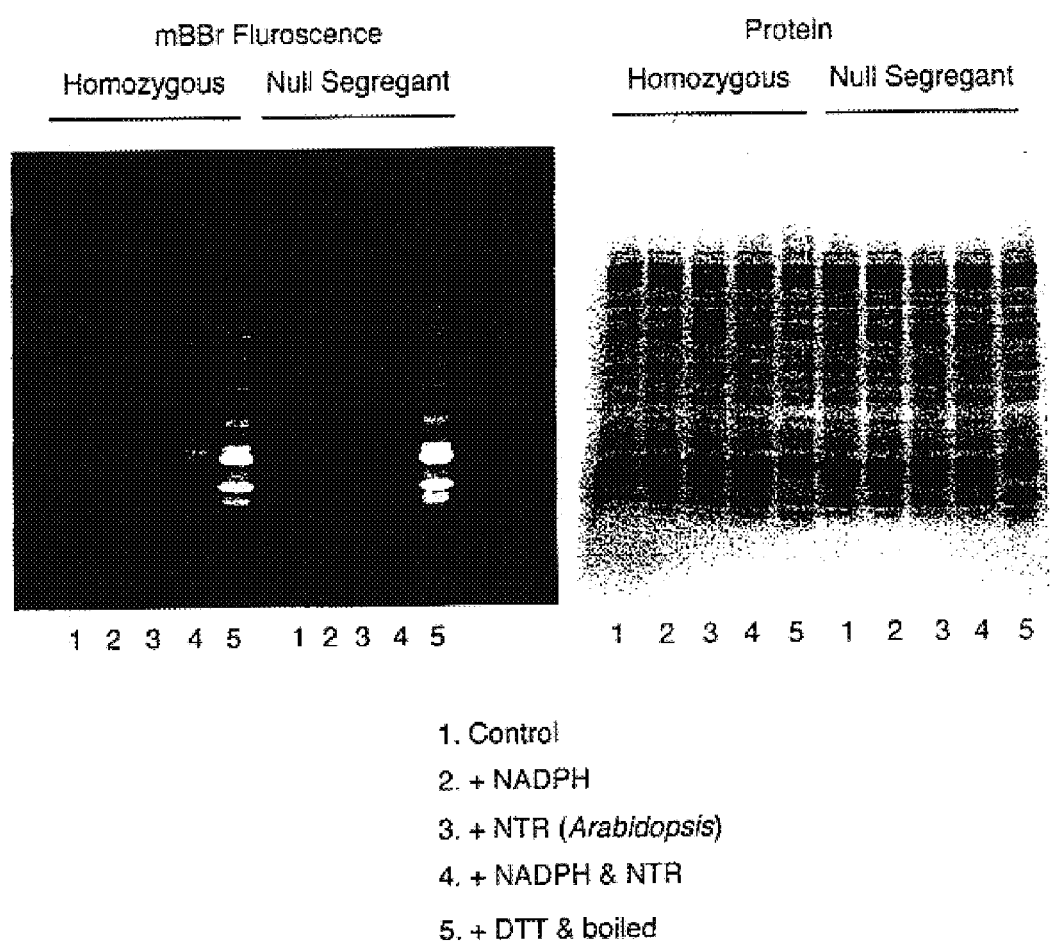
FIG. 18 show the effect of NTR on the reduction of proteins in extracts of transgenic wheat overexpressing thioredoxin h verses a null segregant.

The results shown in FIG. 18 indicate that the albumin/globulin proteins in the homozygous transgenics overexpressing thioredoxin h are more efficiently reduced than the albumin/globulin fraction of grain from their null segregant counterparts.

Example 5

Effect of Overexpressed Thioredoxin h on Allergenicity of Proteins from Wheat Grain The following protocol was approved by the appropriate committees at both the University of California-Davis (Animal Use and Care Administrative Advisory Committee, effective Jan. 21, 1999–Jan. 21, 2000 and the University of California-Berkeley (Animal Care and Use Committee, effective May 1, 1999–Apr. 30, 2000.

Dogs from the UC-Davis sensitized Dog Colony (Ermel et al. 1997) that were senitized to commercial whole wheat grain extract (Bayer), were selected as strong reactors from two groups: 1) 2 year-old, designated "young dogs," and 2) 7 year-old, "old dogs." Before starting the skin tests, each animal received an intravenous injection of 5 ml sterile saline solution containing 0.5% Evans Blue (0.2 ml/kg). After 5 min, skin tests were performed by 100 $\mu$l intradermal injections of log dilutions of each wheat protein fraction in PBS buffer on the ventral abdominal skin. The quantity of protein injected ranged from 33 pg to 10 $\mu$g. The fractions tested were: 1) salt water-soluble (albumins and globulins); 2) ethanol-soluble (gliadins); acid acetic-soluble (glutenins). After 20 min, length and width of wheal areas were measured by a blinded reader. The total area was calculated as an ellipse ($\pi$/4×L×W). Protein allergenicity of the null segregant (control) and the hormozygous wheat lines was obtained by comparison of the total wheal area generated by the different dilutions of each extract.

Figure 19:
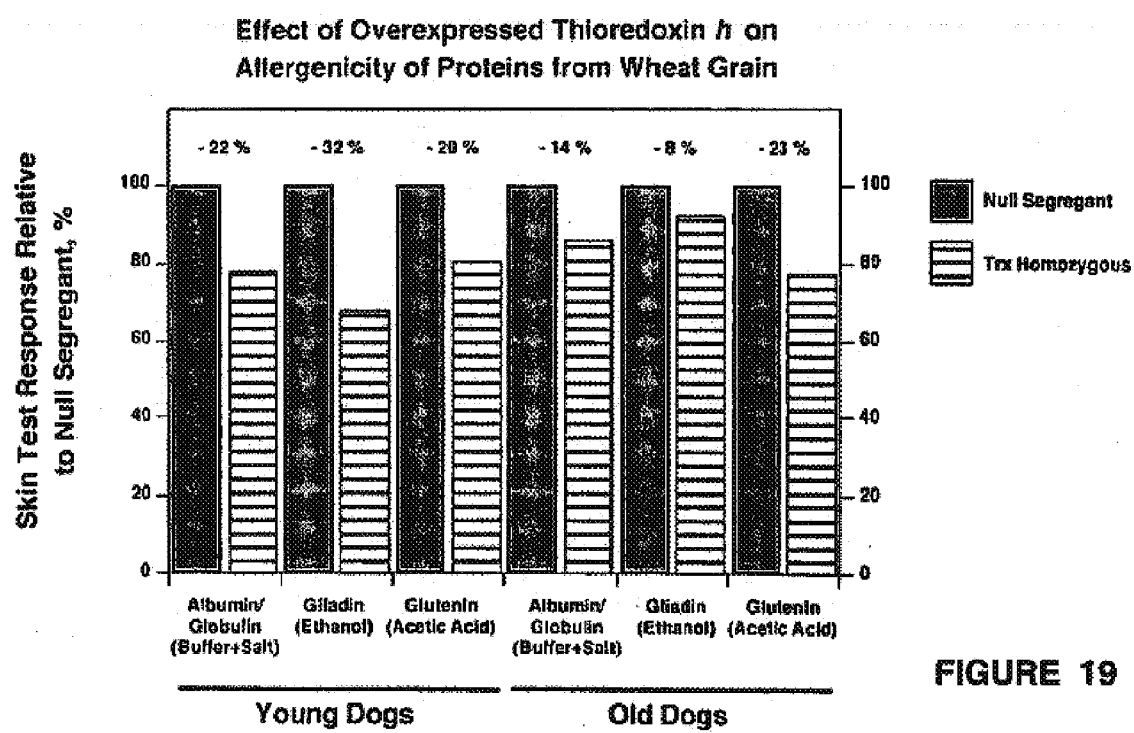
FIG. 19 shows the effect of overexpressed thioredoxin h on allergenicity of proteins from wheat grain.

The responses of the animals are shown in FIG. 19 and indicate that the proteins obtained from the transgenic wheat are less allergenic that the protein obtained from the null segregant. For each fraction tested, both young and old animals were less responsive to proteins from transgenic wheat The allergenicity with the transgenics were decreased at least 5% in comparison to nontransgenic controls. The allergenicity in the young dogs was more substantially reduced, ranging from 20 to 32% decrease. In contrast, the allergenicity in older animals was reduced by 8 to 23%.

To demonstrate the hypoallergenicity of malt produced from the transgenic wheat grain, malt is produced according to standard protocols known in the art from the transgenic seeds. Extracts of the malt are produced according to the above procedure. Young and old sensitized dogs, as described above, are injected intravenously with about 5 ml sterile saline solution containing 0.5% Evans Blue (0.2 ml/kg). After about 5 min, skin tests are performed by 100 µl intradermal injections of log dilutions of each malt protein fraction in PBS buffer on the ventral abdominal skin. The quantity of protein injected is about 33 pg to 10 µg. The fractions are as described above. After about 20 min, the length and width of the wheal areas are measured by a blinded reader and the total area is calculated as an ellipse. Malt protein allergenicity of malt produced from a null segregant (control) and malt from homozygous wheat lines are obtained by comparison of the total wheal area as described above. The allergenicity in the young dogs is more substantially reduced, and range from about 20–30% decrease. The older animals allergenicity is reduced by about 5–20%.

Accordingly, a food product such as beer produced from the hypoallergenic malt also is hypoallergenic.

Example 6

Transgenic Sorghum Expressing Barley Thioredoxin h

A. Seed Digestibility

Seeds from ten major cultivars of Sorghum vulgare are screened for a thioredoxin-dependent increase in digestibility of constituent proteins using simulated gastric (pepsin), and intestinal (pancreatin) fluids. The cultivars are representative of those grown in the United States, Australia and different parts of Africa.

Albumin, globulin, kafirin, and glutelin protein fractions are isolated according to their differential solubilities. Seed, 3 g, is ground in a coffee grinder, extracted sequentially with 30 ml of: [1] 0.5 M NaCl, [2] 60% (v/v) 2-propanol, and [3] 0.1 M sodium borate buffer, pH 10, on a shaker at 25° C. for 30 min, 4 hours, and 4 hours, respectively. The extracted fractions correspond, respectively, to [1] albumin plus globulin [2] kafirin, and [3] glutelin. Total kafirins or cross-linked kafirins are extracted with 60% 2 propanol plus 1% 2-mercaptoethanol (Shull et al., 1992). Each suspension is clarified by centrifugation at 10,000×g for 20 min at 4° C.; three successive extractions are performed with the salt solution followed by two water washes. The remaining extractions are repeated twice. Resulting supernatant solutions are pooled and the digestibility of each fraction is tested on the same day as isolation.

Aliquots of individual sorghum protein fractions are reduced either with the NADP/thioredoxin or the NADP/glutathione system prior to digestion and the results compared with untreated control preparations. Alternatively, total protein extracted with sodium myristate, a nonreducing detergent that solubilize wheat gliadins and glutenins in a biochemically active form (Kobrehel and Buchuk, 1978) can be tested for digestibility. Reduction of the disulfide bonds of proteins is performed using mBBr/SDS-PAGE as previously described (del Val et al., 1999) in a volume of 100 µl with either (i) the NADP/thioredoxin system, consisting of 5 µl of 25 mM NADPH, 8 µl of 0.3 mg/ml $E.$ $coli$ thioredoxin and 7 µl of 0.3 mg/ml $E.$ $coli$ NTR; or (ii) the NADP/glutathione system composed 5 µl of 25 mM NADPH, 10 µl of 30 mM glutathione and 15 µl of 0.1 mg/ml glutathione reductase. Reactions are carried out in a 30 mM physiological buffered saline (PBS) solution containing 50 µg of each protein. The reaction mixtures are incubated at 4° C. overnight or at 37° C. and 55° C. for 15 min (Kobrehel et al., 1992; del Val et al., 1999). The temperature found to work best is used for subsequent experiments. For complete reduction, samples are incubated in PBS with 5 µl 100 mM DTT and boiled 5 min. Protein fractions (albumin-globulin, kafirin, glutelin: 240 µg protein) is subjected to simulated digestion, either untreated or reduced with NADP/thioredoxin or NADP/glutathione, by pepsin (gastric simulation) or trypsin/chymotrypsin/carboxypeptidase (pancreatin: intestinal simulation).

Pepsin Assay

Each fraction, 500 µg of protein, is added to 100 µl of simulated gastric fluid [0.32% pepsin (w/v) and 30 mM NaCl adjusted to pH 1.2 with HCl] (Astwood et al., 1996). The reaction mixture is incubated for up to 60 min at 37° C. and stopped with 0.375-fold volume of 160 mM $Na_2CO_3$ to give neutral pH. The protein mixture is subjected to SDS-PAGE and stained for protein with Coomassie blue as described below.

Pancreatin Assay

Each fraction, 500 µg protein, is added to 100 µl of simulated intestinal fluid (1% porcine pancreatin (w/v), 48.9 mM monobasic potassium phosphate and 38 mM NaOH adjusted to pH 7.5 with NaOH) (see United States Pharmacopeiai, 1995). The reaction mixture is incubated for up to 60 min at 37° C. and stopped with ¹⁄₁₀ volume of 100 mM phenylmethyl sulfonyl fluoride (PMSF) plus 1 µg/ml leupeptin. The protein mixture is subjected to SDS-PAGE and stained with Coomassie blue as described below.

Two widely grown cultivar showing the most improved susceptibility to proteolytic and starch digestion after reduction by the thioredoxin system are used for the transformation work.

B. Isolation and Digestibility of Starch

Starch Granule Isolation

Starch granules from dry mature sorghum grain are extracted as described (Sun and Henson 1990). Sorghum grain is washed with distilled water and steeped for 48 h in 20 mM Na-acetate buffer, pH 6.5, containing 0.02% NaAzide. Softened kernels are ground first with a motar and pestle and then with a VirTis homogenizer for 6 min at 80% full speed and the grist passed through two sieves (250 and 75 µm). Crude starch that passes through both sieves is purified by centrifugation (60×g for 2.5 min) through a layer of 65% (w/v) sucrose. Pelleted starch granules are recentrifuged one or two times under the same conditions and resuspended in 20 mM sodium acetate buffer, pH 6.5 containing 0.02% sodium azide.

Starch Digestion

Starch digestibility is measured based on enzymatic hydrolysis using porcine pancreatic alpha-amylase (Type VI-B, Sigma Chemical Co., St Louis, Mo.). Incubation mixtures containing 2% (w/v) starch, 0.5% (w/v) BSA, 0.02% (w/v) azide, 25 mM NaCl, 5 mM $CaCl_2$, and 10 units of alpha-amylase in 10 mM sodium phosphate buffer, pH 6.9, are incubated 37° C. Aliquots (50 to 100 µl) of reaction mixture is periodically removed for determination of glucose and total reducing sugars released from starch granules. Reducing sugar concentration is measured by the dinhtrosalicylic acid method (Bernfeld, 1955) and total starch content by the enzymatic procedure of McClear et al. (1994).

Reduction of Protein on Starch Granules

Aliquots of the isolated 2% (w/v) starch are incubated with the NTS system to reduce the proteins on the surface of the granule as described above (Examples 3 and 4). Following reduction, the starch granules are tested for digestibility by alpha-amylase (McCleary et al. 1994) and stimulated intestinal fluid (Board of Trustees 1995)

C. Production of Stably Transformed Sorghum Lines and $T_1$ Plants Containing Barley trxh Using a cDNA library from scutellum tissues of barley (constructed by R. Schuurink, UCB), a full-length gene for thioredoxin h (trxh; FIG. 20) was isolated and characterized (Calliau, del Val, Cho, Lemeaux, Buchanan, unpublished). The full-length cDNA clone has been placed into expression vectors with the hordein promoters plus the targeting sequence as described (Cho et al., unpublished) is used for sorghum transformation. This vector, pdBhssBTRXN-2, contains the 0.43-kb $B_1$-hordein promoter plus its signal sequence, barley trxh (btrxh) and nos.

Sorghum is transformed by the methods of Cho et al., (1998b, 1999b, 1999c, 1999d, 2000) to give rise to highly regenerative green tissues. These tissues contain multiple, light-green, shoot meristem-like structures, which were charactrized as such in barley because they expressed a gene associated with maintenance of the shoot meristematic state, a knotted I homologue (Zhang et al., 1998). Target tissues such as these highly regenerative tissues, which a high percentage of totipotent cells capable of sustained cell division and competent for regeneration over long period, represent a high-quality target tissue for transformation. They can be maintained for more than a year with minimal loss in regenerability (Cho et al., 1998b, 1999b, 1999c, 1999d, 2000; Kim et al., 1999; Ha et al., 2000). In addition, the result from genomic DNA methylation analyses (Zhang et al. 1999b) showed that barley plants regenerated from these highly regenerative tissues were less variable in terms of methylation pattern polymorphism and agronomic performance than those regenerated from callus maintained in the embryogenic state.

Media developed for the other cereals and grasses are utilized for optimizing the response of the sorghum variety, TX430, to produce high quality, green regenerative tissues with sorghum similar to those observed with other cereals and grasses. Such tissues have been used successfully for stable transformation with all varieties tested. Briefly, this method, the development of green, regenerative tissues, involves the initiation of embryogenic cultures from immature embryos of cultivar TX430. The medium giving the highest quality tissue is D'BC2 and DBC3 (Cho et al., 1998a–c, 1999d). Such media, containing copper, maltose, and cytokinins have been found to improve the quality and long-term regenerability of tissue from other cereal and grasses. Tissue developed on this medium is used as transformation targets using bombardment.

The desired DNA construct(s) containing barley trxh are introduced into target cells via bombardment. Selection to identify transformants is via bialaphos, kanamycin, or other appropriate selection agents according to published procedures (Cho et al., 1998a–c; Lemaux et al 1999). Small portion of putatively transformed calli are analyzed by PCR (Cho et al., 1998a–c) for barley trxh and transformed tissue is manipulated to regenerate plants (Cho et al., 1998a–c). Leaf tissue is tested for resistance to the selective agent, if possible, and as appropriate is analyzed by PCR for the transgene(s). Plants are grown to maturity to obtain $T_1$ seeds and homozygous $T_2$ plants.

D. Determination of Amounts and Activity of TRXh in Stably Transformed Sorghum

The activity of the barley thioredoxin h from the different production systems (targeted vs. nontargeted, i.e. with or without the signal sequence, repectively) and obtained with different fractionation procedures, as described above, is assayed using the DTNB [2',5-dithiobis (2-nitrobenzoic acid)] method (Florencio et al., 1988) as described (Cho et al., 1999e). The NTR and thioredoxin controls are prepared from wheat grains as described by Johnson et al. (1987a, b).

Western Blot Analysis

Western blots are performed on extracts from selected transgenic lines as well as control seeds. Lots of 10 to 20 intact seeds are processed and analyzed for content of TRXh and NTR by SDS-PAGE and western blot procedures (Cho et al., 1999e).

Preparation of Seed Extract, Heat Treatment and Column Chromatography

Extracts are prepared, heat treated, and fractionated by column chromatography as described by Cho et al., (1999e).

Measurement of Thioredoxin h Activity

Thioredoxin h is assayed by the chloroplast NADP-malate dehydrogenase procedure as adapted for barley (Cho et al., 1999).

Protein Determination

Protein is determined or measured according to Bradford (1976) using the Coomassie blue method with gamma-globulin as a standard. Protein content is confirmed by measuring total nitrogen in an automated gas analyzer or by standard micro-kjeldahl procedure.

E. Measurements in Changes in Abundance and Redox State of Endosperm Proteins Transgenic sorghum seeds overexpressing barley thioredoxin h are the staring material used to demonstrate that increased levels of this protein cause altered digestibility. Preliminary mBBr measurements are also made with the genetically engineered grain. Changes in the redox state of endosperm protein are determined using the mBBr/SDS-PAGE procedure (Krobehel et al., 1992). As the major indigenous storage proteins in sorghum are known to be insoluble, propanol as well as the different aqueous endosperm extracts are monitored in the grain. Residues are extracted sequentially, as described above (A. Seed Digestibility) for the various protein fractions. Supernatant fractions of each extract is analyzed for protein and fluorescence by the mBBr/SDS-PAGE technique.

Dry grain, 1 g, from transgenic and null segregant lines are ground with a mortar and pestle in liquid nitrogen. When the liquid nitrogen evaporates, 3–6 ml of 30 mM Tris-HCl, pH 7.9 buffer containing 1 mM EDTA and 1 mM mBBr is added and mixed for 1 min. After thawing the extract is incubated 15 min, centrifuged (10 min at 12,000×g), extracted sequentially with salt, propanol, and borate solutions as described above (A. Seed Digestibility). Sixty μg protein samples are loaded onto a 10–20% SDS-polyacrylamide gradient gel as described above. Following electrophoresis (1 h, constant current of 30 mA), gels are soaked for 2 h in 12% (w/v) trichlobracetic acid and transferred to a solution containing 40% methanol and 10% acetic acid for 12 h to remove excess mBBr. Gels are scanned for fluorescence with a UV light source (365 nm) and stained for protein with Coomassie blue.

F. Measurements of Change in Digestibility and Solubility of Endosperm Proteins in $T_1$ Heterozygous and $T_2$ Homozygous Sorghum Grain In parallel with the in vitro experiments (Ori et al., 1995), the extent that in vivo thioredoxin-mediated reduction contributes to the digestibility and solubility of sorghum endosperm proteins is determined. The extent of solubilization of protein is measured using the ratio of the soluble to the insoluble protein in the transgenic, relative to a null segregant. Extracts are prepared in parallel without mBBr labeling and tested for susceptibility to digestion by simulated gastric and intestinal fluids are described above (Example 3). The proteins from the different transgenic grain also are reduced with thioredoxin and glutathione as described above (A. Seed Digestibility).

G. Measurements of Change in Digestibility of Starch in $T_1$ Heterozygous and $T_2$ Homozygous Sorghum Grain As in the case of the kafirin storage proteins, the ability of the overexpressed thioredoxin h to enhance the digestibility of starch with alpha-amylase is determined. The starch is isolated from both transgenic and null segregant lines and its digestibility tested in vitro with alpha-amylase as described above (B. Isolation and Digestibility of Starch). Because of their association with starch granules, an increase in the digestibility of the kafirin proteins is accompanied by an increase in the digestibility of the starch.

H. Thioredoxin h Overexpressed in Sorghum to Improve Digestibility of Grain Protein The above-noted digestibility of the different protein fractions (albumin/globulin, kafirin, glutelin) is tested with simulated gastric and intestinal fluids. The results from the transgenic grain overexpressing barley TRXh is compared to those with the null segregant to demonstrate improvement in digestibility in the transgenic grain.

Example7

Improvement of Dough Quality

In U.S. application Ser. No. 08/211,673 (expressly incorporated by reference), dough quality was improved by reducing the flour proteins using the NADP/thioredoxin system. Without being bound by theory, reduced thioredoxin specifically breaks intramolecular sulfur-sulfur bonds that cross-link different parts of a protein and stabilize its shape. When these cross-links are broken the protein can unfold and supposedly link with other proteins in dough, creating an interlocking lattice that forms an elastic network. The dough rises because the network helps trap carbon dioxide produced by yeast during the fermentation process. It was proposed that the reduced thioredoxin reduced the gliadins and glutenins in flour letting them recombine in a way that strengthened the dough. Reduced thioredoxin facilitated their forming a protein network during dough making. Treatment of intermediate or poor quality wheat flour (Apollo cultivar) with *E. coli* thioredoxin, NADP-thioredoxin reductase, and NADPH showed dough strengthening (higher farinograph measurements) and improved loaf volume and viscoelasticity in comparison with untreated flour. Higher farinograph measurements of dough correspond to improved dough strength and improved baked good characteristics such as better crumb quality, improved texture and higher loaf volume.

Wheat Bread Baking Studies and Farinograph Measurements

The baking tests are carried out by using a computer operated PANASONIC bread maker to demonstrate improved quality of dough made using flour prepared from the transgenic seeds of the present invention.

Composition of bread:

| Control: | |
| --- | --- |
| Flour*: | 200 gm (dry) |
| Water: | 70% hydratation |
| Salt (NaCl): | 5.3 g |
| Yeast: | 4.8 g (*S. cerevisiae*) (dry yeast powder) |

*Flour samples are obtained from transgenic and non-transgenic wheat (cv. Thesee Apollo, Arbon, and other animal feed grade and other grades having from poor to good baking quality), sorghum, corn, and rice.

Experimental conditions

Flour and salt are weighed and mixed

The volume of water needed to reach a hydration of 70% was put into the bread maker.

The mixture of flour and salt is added to the water and the baking program; is started by the computer. The complete program lasts about 3 hrs 9 min and 7 secs.

Yeast is added automatically after mixing for 20 min and 3 secs.

The program operating the Panasonic apparatus is:

| | | Mixing | |
| --- | --- | --- | --- |
| Segments | Duration | Conditions | Heating |
| Mixing | 00:00:03 | T1 | off |
| Mixing | 00:05:00 | T2 | off |
| Mixing | 00:05:00 | T1 | off |
| Rest | 00:10:00 | TO | off |
| Mixing | 00:17:00 | T2 | off |
| Mixing | 00:07:00 | T1 | off |
| Rest | 00:30:00 | TO | to reach 32° C. |
| Mixing | 00:00:04 | T1 | 32° C. |
| Rest | 01:15:00 | TO | 32° C. |
| Baking | 00:14:00 | TO | to reach 180° C. |
| Baking | 00:26:00 | TO | 180° C. |

Mixing Conditions: TO = no mixing (motor at rest)
T1 = normal mixing
T2 = alternately 3 second mixing, 3 second rest After the dough is formed, farinograph readings are taken as described in U.S. application Ser. No. 08/211,673. Bread loaf volume is measured at the end of the baking, when bread loaves reach room temperature.

Farinograph readings of dough produced from flour made from transgenic wheat seeds of the invention are at least about 10–20% higher and are maintained about 40% longer than dough produced from flour made from non-transgenic seeds. Bread produced from flour made from transgenic seeds of the invention has at least about 5% and up to about 20% increased volume in comparison to bread produced from flour made from non-transgenic seeds. Bread-like products made from transgenic flour of cereals that normally produce a nonglutenous flour, for example, rice, hold together and hold gas better than products produced from the flour of their nontransgenic counterparts. They also show at least a 3% increase in loaf volume when compared to their nontransgenic counterparts.

Example 8

Effect of Glucose-6-Phosphate Dehydrogenase on Reduction of Proteins in Exacts of Homozygous vs. Null Segregant Wheat Grain Overexpressing Thioredoxin h Samples were from the salt-soluble fractions (albumin and globulin) of the transgenic and null segregant wheat grain overexpressing wheat thioredoxin h. Reactions were carried out in 30 mM Tris-HCl buffer, pH 7.9, in a final volume of 100 μl. The complete reaction mixture contained 10 μmol glucose-6-phosphate, 0.25 μmol NADP, 2 units glucose-6-phoshate dehydrogenase (Bakers Yeast, Type XV, Sigma, St Louis, Mo.), plus or minus 1.5 μg NTR (Arabidopsis), and 80 μg protein. Other treatments, where omission of one or two component(s) of the NADPH generating system, were as indicated. The negative control was the extracted protein alone. As a positive control NADPH was used in place of NADP/glucose-6-phoshate/ glucose-6-phosphate dehydrogenase.

After incubation at 37° C. for 60 min, 100 nmol mBBr was added tot he reaction mixture, and the reaction was continued for 15 min. Ten μl of 100 mM 2-mercaptoethanol was added to stop the reaction and derivative excess mBBr. An appropriate amount of 4×Laemmeli sample buffer was added and the samples were applied onto 10–20% polyacrylamide gel in the presence of SDS. Electrophoresis was carried out at room temperature at 7 mA/gel for 16 hours. Flourescence of sulfhydryl containing proteins on gels was captured by Gel Doc 1000 (Bio-Rad), protein was stained by 0.025% Coomassie Brilliant Blue G250 in 10% acetic acid.

For visualizing the effect of glucose-6-phosphate dehydrogenase (FIG. 23): in the presence of NTR, comparison of lanes 2 vs. 4 (−NADP) and lanes 5 vs. 7 (+NADP) (+NTR gel on the left); in the absence of NTR, compare lanes 1 vs. 3 (−NADP) and lanes 2 vs. 4 (+NADP) (−NTR gel on the right). The maximal increase in reduction effected by glucose-6-phosphate dehydrogenase was observed in the presence of NTR, without NADP (lane 2 vs. lane 4, gel on the left). Note also the greater reduction of NTR in lane 4 vs. lane 2.

Figure 23:
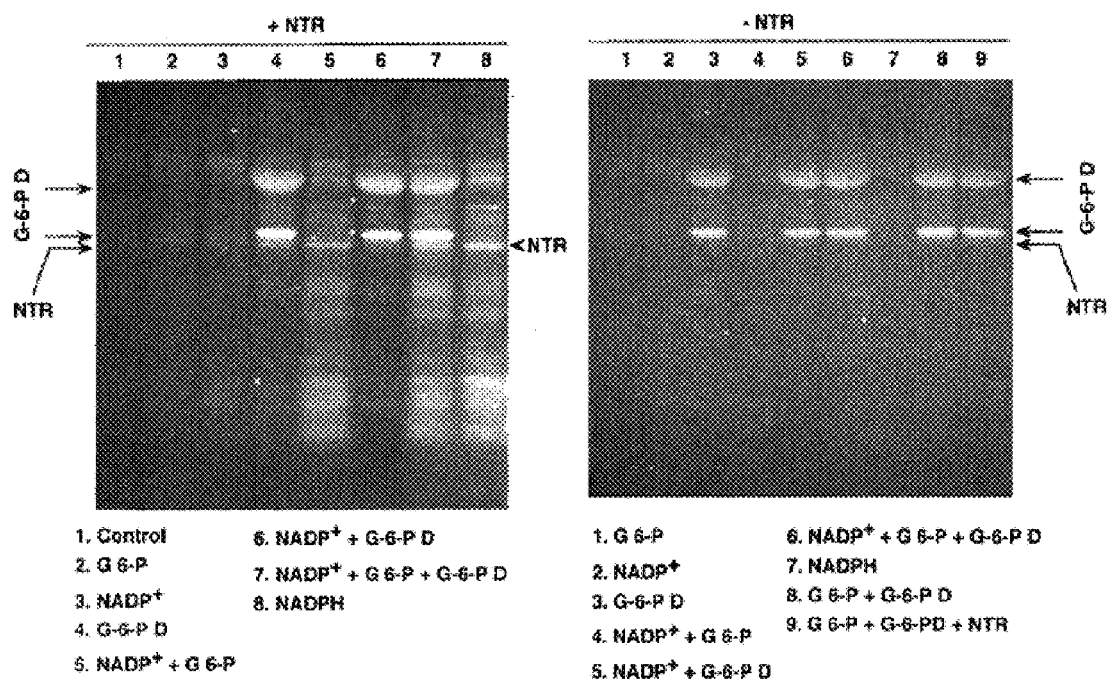
FIG. 23 shows the effect of glucose-6-phosphate dehydrogenase on the reduction of proteins in extracts of transgenic wheat grain overexpressing thioredoxin h in the presence of glucose 6-phosphate and Arabidopsis NTR:+/–NTR.
Figure 24:
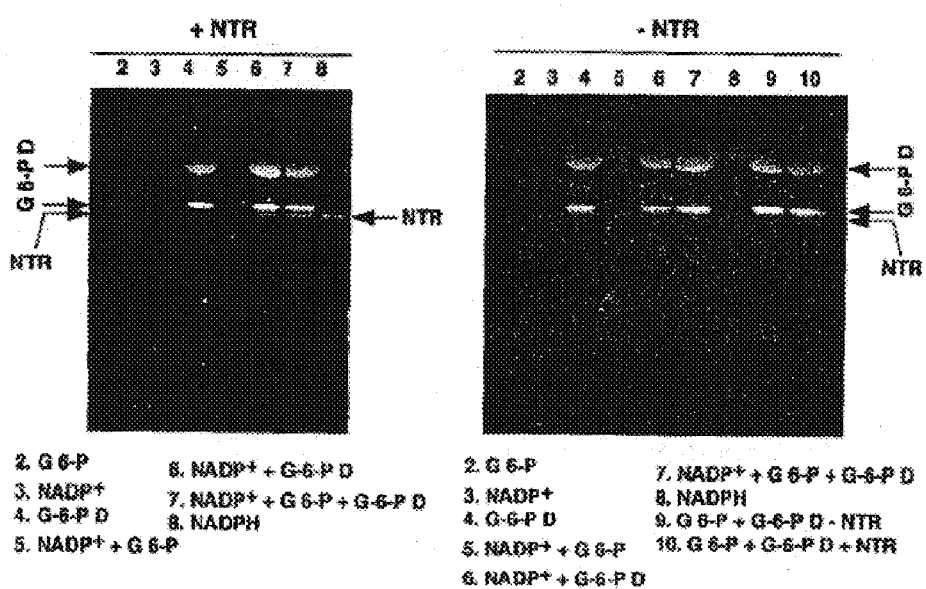
FIG. 24 shows the effect of glucose-6-phosphate dehydrogenase on the reduction of proteins in extracts of extracts of null segregant derived from wheat grain overexpressing thioredoxin h in the presence of glucose 6-phosphate and Arabidopsis NTR:+/–NTR.

With the null segregant (FIG. 24), note the greater reduction of NTR in the presence of glucose-6-phosphate dehydrogenase (lane 4 vs. lane 2) but a lower extent of the reduction of the smaller target proteins (lane 4) compared to the corresponding treatment (lane 4) with the transgenic extract (FIG. 23).

This invention has been detailed both by example and by description. It should be apparent that one having ordinary skill in the relevant art would be able to surmise equivalents to the invention as described in the claims which follow but which would be within the spirit of the foregoing description and examples. It should be realized that those equivalents and various modifications as may be apparent to those of skill in the art to which the invention pertains also fall within the scope of the invention as defined by the appended claims. All herein cited patents, patent applications, publications, references, and references cited therein are hereby expressly incorporated by reference in their entirety.

References

All references, patents, patent applications, publications, and references cited therein are hereby expressly incorporated by reference in their entirety.

Altschul et al. (1990) J. Mol. Biol. 215:403–10.
Altschul et al. (1994) Nature Genet. 6:119–29.
Altschul et al. (I 996) Methods in Enzymology 266:460–480.
Astwood et al. (1996) Nature Biotech. 14:1269–1273.
Ausubel et al. (1987) In: Current Protocols in Molecular Biology, Greene Publishing Associates and Wiley-Intersciences.
Bagga et al. (1997) Plant Cell 9:1683–1696.
Bemfeld P (1955) Amylases, alpha and beta. Methods Enzymol. 1:149–158.
Besse and Buchanan (1997) Bot. Bull. Acad. Sin. (Taipei) 38:1–11.
Besse I, Wong J H, Kobrehel K, Buchanan B B (1996) Thiocalsin: A thioredoxin-linked, substrate-specific protease dependent on calcium. Proc. Natl. Acad. Sci. USA 93:3169–3175.
Berstermann A, Vogt K, Follmann H (1983) Plant seeds contain several thioredoxins of regular size. Eur/ J,/ Biochem. 131:339–344.
Bondenstein-Lang J, Buch A, Follman H (1989) Animal and plant mitochondria contain specific thioredoxins. FEBS LetL 258:22–26.
Bower M S, Matias D D, Fernandes-Carvalho E, Mazzurco M, Gu T, Rothstein S J, Goring D R (1996) Two members of the thioredoxin in-family interact with the kinase domain of a Brassica S locus receptor kinase. Plant Cell 8:1641–1650.
Bradford M M (1976) Anal. Biochem. 72:2 48–254.
Brandt A, Montembault A, Cameron-Mills V, Rasmussen S K (1985) Primary structure of a $B_1$ hordein gene from barley, Carlsberg Res. Commun. 50:333–345.
Brugidou C, Marty I, Chartier Y. Meyer Y (1993) The Nicotiana tabacum genome encodes two cytoplasmic thioredoxin genes which are differently expressed. Mol. Gen. Genet. 238:285–293.
Buchanan B B (1991) Regulation of $CO_2$ assimilation in oxygenic photosynthesis: the ferredoxin/thioredoxin system. Arch. Biochem. Biophys. 287:337–340.
Buchanan B B, Adamidi C, Lozano R M, Yee B C, Momma M, Kobrehel K, Ermel R Frick O L (1997) Thioredoxin-linked mitigation of allergic responses to wheat Proc. Natl. Acad. Sci. USA 94:5372–77.
Buchanan et al. (1994) Arch. Biochem. Biophys. 314:257–260.
Chiu W. Niwa Y, Zeng W, Hirano T, Kobayashi H, Sheen J (1996) Engineered GFP as a vital reporter in plants. Current Biol. 6:325–330.
Cho M-J, Lemaux P G (1997a) Rapid PCR amplification of chimeric products and its direct application to in vivo testing of recombinant DNA construction strategies. Mol. Biotechnol. 8:13–16.
Cho M-J, Vodkin I, Widholm J M (1997b) Transformation of soybean embryogenic culture by microprojectile bombardment. Plant Biotechnol. 14:11–16.
Cho M-J. Ha C D, Buchanan B B, Lemaux P G (1998a) Subcellular targeting of barley hordein promoter-uidA fusions in transgenic barley seed. P-1024. Congress In Vitro Biology, Las Vegas, Nev. May 30–Jun. 3, 1998.
Cho M-J, Jiang W, Lemaux P G (1998b) Transformation of recalcitrant cultivars through improvrement of regenerability and decreased albinism. Plant Sci. 138:229–244.
Cho M-J, Zhang S. Lemaux P G (1998c). Transformation of shoot meristem tissues of oat using three different selectable markers. In Vitro Cell Dev. Biol. 34P:340.

Cho M-J, Choi H W, Buchanan B B, Lemaux P G (1999a) Inheritance of tissue-specific expression of barley hordein promoter-uidA fusions in transgenic barley plants. Theor. Appl. Genet. 98:1253–1262.

Cho M-J, Buchanan B B, Lemaux P G (1999b) Development of transgenic systems for monocotyledonous crop species and production of foreign proteins in transgenic barley and wheat seeds. In: Application of Transformation Technology in Plant Breeding. Special Seminar for the 30th Anniversary Korean Breeding Soc., Suwon, Korea, Nov. 19,1999, pp.39–53.

Cho M-J, Choi H W, Lemaux P G (1999c) Transgenic orchardgrass (*Dectis glomerata L.*) plants produced from high regenerative tissues. P-1089. Congress In Vitro Biology, New Orleans, La. Jun. 5–9, 1999.

Cho M-J, Jiang W, Lemaux P G (1999d) High frequency transformation of oat via microprojectile bombardment of seed-derived regenerative cultures. Plant Sci. 148:9–17.

Cho M-J, Wong J, Marx C, Jiang W, Lemaux P G, Buchanan B B (1999e) Overexpression of thioredoxin h leads to enhanced activity of starch debranching enzyme (pullulanase) in germinating barley seeds. Proc. Natl. Acad. Sci. USA 96:14641–14646.

Cho M-J, Ha C D, Lemaux P G (2000) Production of transgenic tall fescue and red fescue plants by particle bombardment of mature seed-derived highly regenerative tissues. Plant Cell Rep. (in press).

Christensen and Quail (1996) Transgenic Res. 5:1–6.

Conrad et al. (1998) Journal of Plant Physiology 152:708–711.

Corpet et al. (1988) Nucleic Acids Research 16:10881–90.

del Val, Yee B C, Lazano R M, Buchanan B B, Ermel R E, Lee Y M, and Frick O L (1999) J. Aller. Clin. Immunol. 103:690–4697.

Dai S, Saarinen M, Ramaswamy S, Mayer Y, Jacquot J-P, Ekiund H (1996) Crystal structure of *Arabidopsis thaliana* NADPH dependent thioredoxin reductase at 2.5 Å resolution. J. Mol. Biol. 264:1044–1057.

Dellaporta S (1993) Plant DNA miniprep and microprep. Freeling M, Walbot V (eds) In: Maize Handbook. p 522–525.

Del Val G, Yee B C, Lozano R M, Buchanan B B, Ermel R W, Lee Y M, Frick O L (1999). Thioredoxin treatment increases digestibility and lower allergenicity of milk. J. Allergy Clinical Immunol. 103(4):690–697.

Entwistle J, Knudsen S, Muller M, Cameron-Mills V (1991) Amber codon suppression: the in vivo and in vitro analysis of two C-hordein genes from barley. Plant Mol. Biol. 17:1217–1231.

Ermel R W, Knock M, Griffe S M, Reinhart G A, Frick O L. 1997. The atopic dog; A mode for food allergy. Lab. Animal Sci. 47:40–49.

Fennema O R (1996) Food Chemistry. New Marcel Dekker. 1–15.

Florenclo et al. (1988) Arch. Biochem. Biophys. 266:49–507.

Forde B G, Heyworth A, Pywell J, Kreis M (1985) Nucleotide sequence of a B1 hordein gene and the identification of possible upstream regulatory elements in endosperm storage protein genes from barley, wheat and maize. Nucl. Acids Res. 13:7327–7339.

Furlong-munoz A (1996) The basis of food allergies. Cereal Food World. 41:71–72.

Gautier et al. (1998) Eur. J. Biochem. 252:314–324.

Gelvin et al. (1990) Plant Molecular Biology Manual, Klower Academic Publishers.

Grimwade et al. (1996) Plant Molecular Biology 30:1067–1073.

Ha C D, Lemeaux P G, Cho M-J (2000) Stable transformation of a recalcitrant Kentucky bluegrass (*Poa praetensis L.*) cultivar using mature seed derived high regenerative tissues. In Vitro Cell Dev. Biol. (submitted)

Hamaker B R, Kirleis A W, Mertz E T, Axtell JD (1986) Effect of cooking on the protein profiles and in vitro digestibility of sorghum and maize. J. Agric. Food Chem. 34:647649.

Hardie D G. (1975) Phytochem. 14:1719–1722.

Higgins and Sharp (1988) Gene 73.237–244.

Higgins and Sharp (1989) CABIOS 5:151–153.

Huang X et al. (1992) Parallelization of a local similarity algorith. Compt Appl. Biosci. 8:155–165.

Hunter C P (1988) Plant regeneration from microspores of barley, Hordeurm vulgare. PhD thesis. Wye College, University of London, Ashford, Kent Innis et al. (eds.) (1990) PCR Protocols, A Guide to Methods and Applications, Academic Press, Inc., San Diego, Calif.

Ishiwatari et al. (1995) Planta 195(3):456–463.

Jacquot J-P, Rivera-Madrid R. Marino P, Kollarova M, Le Maréchal P. Miginiac-Maslow M, Meyer Y (1994) *Arabidopsis thaliana* NADPH-thioredoxin reductase cDNA characterization and expression of the recombinant protein in *Eschenchia coli*. J. Mol. Biol. 235:1357–1363.

Jiao J, Yee B C, Kobrehel K, Buchanan B B (1992) Effect of thioredoxin-linked reduction on the activity and stability of the Kunitz and Bowman-Birk soybean trypsin inhibitor proteins. J. Agric. Food Chem 40:2333–2336.

Johnson T C, Cao R Q, Kung J E, Buchanan B B, Holmgren (1987a) Thioredoxin and NADP-thioredoxin reductase from cultured carrot cells. Planta 171:321–331.

Johnson T C, Wada K, Buchanan B B, Holmgren A (1987b) Reduction of purothionin by the wheat seed thioredoxin system and potential function as a secondary thiol messenger in redox control. Plant Physiol. 85:446–451.

Kim H-K, Lemaux P G, Buchanan B B, Cho M-J (1999) Reduction of genotype limitation in wheat (*Trticum aestivum L.*) transformation. P-1021. Congress In Vitro Biology, New Orleans, La. Jun. 5–9, 1999.

Kobrehel and Bushuk (1978) Studies of Glutenin XI. Note on Glutenin Solubilization and Surfactants in Water. Cereal Chemistry 55:1060.

Kobrehel et al. (1994) Thioredoxin-linked reduction of wheat storage proteins. II. Technological Consequences. In: Gluten Proteins:1993. Association of Cereal Research; Detmold, Germany.

Kobrehel K, Wong J H, Balogh A, Kiss F, Yee B C, Buchanan B B (1992) Specific reduction of wheat storage proteins by *thioredoxin h*. Plant Physiol. 99:919–924.

Kobrehel K, Yee B C, Buchanan B B (1991) Role of the NADP/thioredoxin system in the reduction of ct-amylase and trypsin inhibitor proteins. J. Biol. Chem. 266:16135–16140.

Kruger et al. (1988) Cereal Chem. 65:208–214.

Kuriyan J, Krishna T S R, Wong L, Guenther B, Pahler A, Williams C H, Model P (1991) Convergent evolution of similar function in 2 structurally divergent enzymes. Nature 352:172–174.

Laemmli U K (1970) Cleavage of structural proteins during the assembly of the head of bacteriophage T4. Nature 227:680–885.

Lemaux P G, Cho M-J. Zhang S, Bregitzer P (1999) Transgenic cereals; *Hordeum vulgare* (barley). Vasil I K (ed) In: Molecular Improvement of Cereal Crops. Klumer Academic Pub, pp 263–267

Lasztity R. 1996. The Chemistry of Cereal Proteins (2nd edition). I. New York: CRC Press.

Lehrer S B, Horner W E, Reese G. (1996) Why are some proteins allergenic? Implications for biotechnology. Crit Rev. Food Sci. Ntr. 36–553–564.

Lemaux P G, Cho M-J, Louwerse J, Williams R. Wan Y (1998) Bombardment-mediated transformation methods for barley. Bio-Rad US/KG Bulletin 2007:1–6.

Lemaux P G, Cho M-J, Zhang S, and Bregitzer P (1999) Transgenic Cereals: Hordeum vulgare L. (barley). In: Molecular Improvement of Cereal Crops. Ed. I. K. Vasil, 255–316, Kluwer Academic Publ. UK.

Li X, Nield J, Hayman D, Langridge P (1995) Thioredoxin activity in the C terminus of Phalaris S protein. Plant J 8:133–138.

Liu S, Kriz, A (1996) Tissue-specific and ABA-regulated maize Glb1 gene expression in transgenic tobacco. Plant Cell Pep. 16:158–162.

Lozano R M, Wong J H, Yee B C, Peters A, Kobrehel K Buchanan B B (1996) New evidence for a role for thioredoxin h in germination and seedling development. Planta 200:100–106.

Lozano R M, Yee B C, Buchanan B B (1994) Thioredoxin-linked reductive inactivation of venom neurotoxins. Arch Biochem Biophys 309:356–362.

MacGregor A W, Macri J L, Schroeder S W, Bazin S L (1994a) Limit dextrinase from malted barley: Extraction, purification, and characterizaion. Cereal Chem. 71:610–617.

MacGregor A W, Macri L J, Schroeder S W, Bazin S L (1994b) J. Cereal Sci. 20:33–41.

MacLean W C, Lopezc-deRomano, Placho R P, Gaham G G (1981) Protein quality and digestibillty of sorghum in preschool children. Balance Studies and Plasma Free Amino Acids. J. Nutr. 111.1928–36.

Macri J L, MacGregor, A W, Schroeder, S W, Bazin, S L. (1993) J. Cereal. Sci. 18:103–106.

Marcus F, Chamberlain S H, Chu C, Masiarz F R, Shin S, Yee B C, Buchanan, B B (1991) Plant thioredoxin h: an animallike thioredoxin occurring in multiple cell compartments. Arch. Biochemn. Biophys. 287:195–198.

Mark and Richardson (1976) Proc. Nag. Acad. Sci. USA 73:780–784.

Marris C, Gallois P. Copley J, Kreis M (1988) The 5' fanking region of a barley B hordein gene controls tissue and developmental specific CAT expression in tobacco plants. Plant Mol. Biol. 10:359–366.

Marty I, and Meyer Y (1991) Nucleotide sequence of a complementary DNA encoding a tobacco thioredoxin. Plant Mol. Biol. 17:143–148.

Marx C, Lemaux P G, Buchanan B B (2000) The wheat grain: new research developments and approaches to improvement In: Seed Technology. Eds. M. Black and D. Bewley, Sheffield Academic Press, UK (in press).

McCleary et al. (1994) Quantitative measurement of total starch in cereal products. J. Cereal Science 20:51–58.

Mena M, Vicente-Carbajosa J, Schmidt R J and Carbonero P (1998) An endosperm-specific DOF protein from barley, highly conserved in wheat, binds to and activates transcription from the prolamin-box of a native B-hordein promoter in barley endospeirn. Plant Journal 16:53–62.

Mertz E T, Hassen M M, Cairns-Whittern C, Kirleis A W, Tu I, Axtell J D (1984) Pepsin digestibility of proteins in sorghum and other major cereals. Proc. Natl. Acad. Sci USA 81:1–2.

Muller M, Knudsen S (1993) The nitrogen response of a barley C-hordein promoter is controlled by positive and negative regulation of the GCN4 and endosperm box. Plant J. 4:343–355.

Needleman and Wunsch (1970) J. MoL Biol. 48:443.

Ori M P, Hamaker B R, Schull J M (1995) In vitro protein digestibility of developing and mature sorghum grain in relation to alpha-, beta-, and gamma-kafirin disulfide crosslinking. Cereal Science 22:85–93.

Pearson and Lipman (1988) Proc. Natl. Acad. Sci. USA 85:9444.

Pearson et al. (1994) Methods in Molecular Biology 24:307–331.

Rasmussen S K, Brandt A (1986) Nucleotide sequences of cDNA clones for C-hordein polypeptides. Carlsberg Res. Commun. 51:371–379.

Rivera-Madrid et al. (1993) Plant Physiobgy 102:324–328.

Rivera-Madrid at al. (1995) Proc. NaU. Acad. Sci. USA 92:5620–5624.

Russel M, Model P (1988) Sequence of thioredoxin reductase from Escherichia coli. Relation to other flavoprotein disulfide oxidoreductases. J. Biol. Chem. 263:9015–9019.

Sambrook et al. (1989) In: Molecular Cloning. A Laboratory Manual, Cold Spring Harbor. N.Y.

Scheibe R (1991) Redox-modulation of chloroplast enzymes. A common principle for individual control. Plant Physiol. 96:1–3.

Schull J M, Watterson J J, Kirlels A W (1992) Purification and immunocytochemical localization of kafirins; in Sorghum bicolor (L. Moench) endosperm. Protoplasma 171:64–74.

Serre L, Lauriere C. (1990) Analytical Biochemistry. 186 (2):312–315.

Shewry P R, Field J M, Kirkman M A, Faulks A J, Miflin B J. (1980) J. Exp. Botany 31:393–407.

Shewry et al. (1986) J. Cereal Sci. 4:97.

Shi J and Bhattacharyya M K (1996) A novel plasma membrane-bound thioredoxin from soybean. Plant Mol. Biol. 32:653–662.

Sicherer S H (1999) Manifestation of food allergy: Evaluation and management Ameri. Fam. Physician. 59:415–424; 429–430.

Sissons M J, Lance R C M, Sparrow D H B. (1993) J. Cereal Sci. 7:19–24.

Sisons M J, Lance R C M, Wallace W. (1994) Cereal Chemistry. 71:520–521.

Smith and Waterman (1981) Adv. Appl. Math. 2:480.

Sørensen M B, Muller M, Skerritt J, Simpson D (1996) Hordein promoter methylation and transcriptional activity in wild-type and mutant barley endosperm. Mol Gen Genet 250:750–760.

Stemmer et al. (1994a) Nature 370:389–391.

Stemmer et al. (1994b) Proc. Natl. Acad. Sci. USA 91(22):10747–10751.

Sun Z, Henson C A (1990) Degradation of native starch granules by barley alpha-glucosidases Plant Physiology 94:320–327.

Suske G, Wagner W, Follman H (1979) NADPH thioredoxin reductase and a new thioredoxin from wheat Z Naturforsch. C 34:214–221.

Takaiwa et al. (1995) Plant Science 111:3949.

Torrent et al. (1997) Plant Molecular Biology 34:139–149.

Vollbrecht E, Veit B, Sinha N, Hake S. (1991) The development gene Knotted-1 is a member of a maize homeobox gene family. Nature 350:241–243.

Vogt K Follmann H (1986) Characterization of three different thioredoxins in wheat. Biochem Biophys Acta 873:415–418.

Wan and Lemaux (1994) Plant Physiol. 104:37–48.

Weissbach & Weissbach (1989) Methods for Plant Molecular Biology, Academic Press.

Wong J H, Jiao J A, Kobrehel K, Buchanan B. (1995) Plant Physiol. 108:67.
Wu et al. (1998) Plant Journal 14:673–683.
Zhang G, Hamaker D (1998) Low alpha-amylase starch digestibility of cooked sorghum flours and the effect of 5 protein. Cereal Chemistry 75:710–713.
Zhang S, Williams-Carrier T, Jackson D, Lemaux P G. 1998. Expression of CDC2Zm and KNOTTED1 during in-vitro axillary shoot meristem proliferation and adventitious shoot meristem formation in maize (Zea mays L) and barley (Hordeum vulgare L.). Planta 204:542–549.
Zhang S, Cho M-J, Koprek T. Yun R. Bregtizer P, and Lemaux P G. (1999a) Genetic transformation of commercial cultivars of oat (Avena sativa L.) and barley (Hordeum vulgare L.) using in vitro shoot meristematic cultures derived from germinated seedlings. Plant Cell Reports 18:959–956.
Zhang S, Zhang S, Cho M-J, Bregitzer P, and Lemaux P G. (1999a) Comparative analysis of genomic DNA methylation status and field performance of plants derived from embryogenic calli and shoot meristematic cultures. In: Plant biotechnology and In Vitro Biology in the 21st Century. Ed. A Altman, 263–267. Kluwer Academic Publishers, the Netherlands.
Zheng et al. (1995) Plant Physiology 109:777–786.

We claim:

1. A transgenic monocot plant selected from the group consisting of barley and wheat wherein at least a part of said plant comprises a recombinant nucleic acid comprising a promoter active in said part operably linked to a nucleic acid encoding a thioredoxin h polypeptide wherein said promoter is a seed or grain maturation-specific promoter and said thioredoxin h polypeptide is selected from the group consisting of barley, rice, Arabidopsis, soybean, wheat, tobacco and *Brassica thioredoxin*.

2. The transgenic plant of claim 1 wherein said part is a seed.

3. The transgenic plant of claim 1 wherein said part is a grain.

4. The transgenic plant of claim 1 wherein said promoter selected from the group consisting of rice glutelins, rice oryzins, rice prolamines, barley hordiens, wheat gliadins, wheat glutenins, maize zeins, maize glutelins, oat glutelins, sorghum kafirins, millet pennisetins, rye secalins, and maize embryo-specific globulin promoters.

5. The transgenic plant of claim 4 wherein said barley hordein promoter is selected from the group consisting of B-1hordein and D-hordein promoters.

6. The transgenic plant of claim 1 wherein said monocot plant is barley.

7. The transgenic plant of claim 1 wherein said thioredoxin h is from the group consisting of barley, wheat and rice thioredoxin h.

8. The transgenic plant of claim 1 wherein said recombinant nucleic acid further comprises a nucleic acid encoding a signal peptide operably linked to said promoter and said nucleic acid molecule encoding a thioredoxin h protein.

9. The transgenic plant of claim 8 wherein said signal peptide targets expression of the thioredoxin h polypeptide to an intracellular body.

10. The transgenic plant of claim 9 wherein said signal peptide is selected from the group of B-1 hordein signal peptide.

11. The transgenic monocot seed or grain selected from the group consisting of barley and wheat comprising a recombinant nucleic acid comprising a promoter active in said seed or grain operably linked to a nucleic acid molecule encoding a barley, rice, Arabidopsis, soybean, wheat, tobacco, or *Brassica thioredoxin h* polypeptide wherein said promoter is a seed or grain maturation-specific promoter.

12. The transgenic seed or grain of claim 11 wherein said promoter is selected from the group consisting of rice glutelins, rice oryzins, rice prolamines, barley hordeins, wheat gliadins, wheat glutenins, maize zeins, maize glutelins, oat glutelins, sorghum kafirins, millet permisetins, rye sacalins, and maize embryo-specific globulin promoters.

13. The transgenic seed or grain of claim 11 wherein said barley hordein promoter is selected from the group consisting of B-1 hordein and D-hordein promoters.

14. The transgenic seed or grain of claim 11 wherein said seed or grain is barley.

15. The transgenic seed or grain of claim 11 wherein said thioredoxin h is selected from the group consisting of barley, wheat, and rice thioredoxin h.

16. The transgenic seed or grain of claim 11 wherein said recombinant nucleic acid further comprises a nucleic acid encoding signal peptide operably linked to said promoter and said nucleic molecule encoding a thioredoxin h protein.

17. The transgenic seed or grain of claim 16 wherein said signal peptide targets expression of the thioredoxin h polypeptide to an intracellular body.

18. The transgenic seed or grain of claim 17 wherein said signal peptide is selected for the group consisting of B-1 hordein and D-hordein signal peptide.

19. The transgenic plant of claim 6 wherein said plant is wheat.

20. The transgenic plant of claim 19 wherein said thioredoxin is wheat thioredoxin h.

21. The transgenic seed or grain of claim 14 wherein said seed or grain is barley.

22. The transgenic seed or grain of claim 21 wherein said thioredoxin is barley thioredoxin h.

23. The transgenic seed or grain of claim 14 wherein said seed or grain is wheat.

24. The transgenic seed or grain of claim 23 wherein said thioredoxin is wheat thioredoxin h.

25. The transgenic plant of claim 1 wherein said thioredoxin is Arabidopsis thioredoxin h.

26. The transgenic plant of claim 1 wherein said thioredoxin is soybean thioredoxin h.

27. The transgenic monocot seed or grain of claim 11 wherein said thioredoxin is *Arabidopsis thioredoxin h*.

28. The transgenic monocot seed or grain of claim 11 wherein said thioredoxin is soybean thioredoxin h.

29. The transgenic plant of claim 1 wherein said thioredoxin is tobacco thioredoxin h.

30. The transgenic plant of claim 1 wherein said thioredoxin is *Brassica thioredoxin h*.

31. The transgenic monocot seed or grain of claim 11 wherein said thioredoxin is tobacco thioredoxin h.

32. The transgenic monocot seed or grain of claim 11 wherein said thioredoxin is *Brassica thioredoxin h*.

* * * * *

SEQUENCE LISTING

<160> NUMBER OF SEQ ID NOS: 25

<210> SEQ ID NO 1
<211> LENGTH: 486
<212> TYPE: DNA
<213> ORGANISM: Artificial Sequence
<220> FEATURE:
<223> OTHER INFORMATION: barley B1-hordein promoter and signal sequence

<400> SEQUENCE: 1

```
aagctttaac aacccacaca ttgattgcaa cttagtccta cacaagtttt ccattcttgt      60
ttcaggctaa caacctatac aaggttccaa aatcatgcaa aagtgatgct aggttgataa     120
tgtgtgacat gtaaagtgaa taaggtgagt catgcatacc aaacctcggg atttctatac     180
tttgtgtatg atcatatgca caactaaaag gcaactttga ttatcaattg aaaagtaccg     240
cttgtagctt gtgcaaccta acacaatgtc caaaaatcca tttgcaaaag catccaaaca     300
caattgttaa agctgttcaa acaaacaaag aagagatgaa gcctggctac tataaatagg     360
caggtagtat agagatctac acaagcacaa gcatcaaaac caagaaacac tagttaacac     420
caatccacta tgaagacctt cctcatcttt gcactcctcg ccattgcggc aacaagtacg     480
attgca                                                               486
```

<210> SEQ ID NO 2
<211> LENGTH: 19
<212> TYPE: PRT
<213> ORGANISM: Artificial Sequence
<220> FEATURE:
<223> OTHER INFORMATION: barley B1-hordein signal protein

<400> SEQUENCE: 2

Met Lys Thr Phe Leu Ile Phe Ala Leu Leu Ala Ile Ala Ala Thr Ser
 1               5                  10                  15

Thr Ile Ala

<210> SEQ ID NO 3
<211> LENGTH: 497
<212> TYPE: DNA
<213> ORGANISM: Artificial Sequence
<220> FEATURE:
<223> OTHER INFORMATION: Barley D-hordein promoter and signal sequence

<400> SEQUENCE: 3

```
cttcgagtgc ccgccgattt gccagcaatg gctaacagac acatattctg ccaaaacccc      60
agaacaataa tcacttctcg tagatgaaga gaacagacca agatacaaac gtccacgctt     120
cagcaaacag taccccagaa ctaggattaa gccgattacg cggctttagc agaccgtcca     180
```

```
aaaaaactgt tttgcaaagc tccaattcct ccttgcttat ccaatttctt ttgtgttggc      240
aaactgcact tgtccaaccg attttgttct tcccgtgttt cttcttaggc taactaacac      300
agccgtgcac atagccatgg tccggaatct tcacctcgtc cctataaaag cccagccaat      360
ctccacaatc tcatcatcac cgagaacacc gagaaccaca aaactagaga tcaattcatt      420
gacagtccac cgagatggct aagcggctgg tcctctttgt ggcggtaatc gtcgccctcg      480
tggctctcac caccgct                                                    497

<210> SEQ ID NO 4
<211> LENGTH: 20
<212> TYPE: PRT
<213> ORGANISM: Artificial Sequence
<220> FEATURE:
<223> OTHER INFORMATION: barley D-hordein signal protein

<400> SEQUENCE: 4

Ala Lys Arg Leu Val Leu Phe Val Ala Val Ile Val Ala Leu Val Ala
 1               5                  10                  15

Leu Thr Thr Ala
        20

<210> SEQ ID NO 5
<211> LENGTH: 28
<212> TYPE: DNA
<213> ORGANISM: Artificial Sequence
<220> FEATURE:
<223> OTHER INFORMATION: primer

<400> SEQUENCE: 5
atatctagaa tggcggcgtc ggcggcga                                         28

<210> SEQ ID NO 6
<211> LENGTH: 27
<212> TYPE: DNA
<213> ORGANISM: Artificial Sequence
<220> FEATURE:
<223> OTHER INFORMATION: primer

<400> SEQUENCE: 6
atagagctct tactgggccg cgtgtag                                          27

<210> SEQ ID NO 7
<211> LENGTH: 26
<212> TYPE: DNA
<213> ORGANISM: Artificial Sequence
<220> FEATURE:
<223> OTHER INFORMATION: primer

<400> SEQUENCE: 7
gtaaagcttt aacaacccac acattg                                           26

<210> SEQ ID NO 8
<211> LENGTH: 34
<212> TYPE: DNA
<213> ORGANISM: Artificial Sequence
<220> FEATURE:
<223> OTHER INFORMATION: primer

<400> SEQUENCE: 8
ccgacgccgc tgcaatcgta cttgttgccg caat                                  34

<210> SEQ ID NO 9
```

```
<211> LENGTH: 33
<212> TYPE: DNA
<213> ORGANISM: Artificial Sequence
<220> FEATURE:
<223> OTHER INFORMATION: primer

<400> SEQUENCE: 9
agaaagcttg gtaccctccg agtgcccgcc gat                          33

<210> SEQ ID NO 10
<211> LENGTH: 48
<212> TYPE: DNA
<213> ORGANISM: Artificial Sequence
<220> FEATURE:
<223> OTHER INFORMATION: primer

<400> SEQUENCE: 10
gaacagctcc tcgcccttgc tcacagcggt ggtgagagcc acgagggc          48

<210> SEQ ID NO 11
<211> LENGTH: 19
<212> TYPE: DNA
<213> ORGANISM: Artificial Sequence
<220> FEATURE:
<223> OTHER INFORMATION: primer

<400> SEQUENCE: 11
ccaagaagtt cccagctgc                                          19

<210> SEQ ID NO 12
<211> LENGTH: 27
<212> TYPE: DNA
<213> ORGANISM: Artificial Sequence
<220> FEATURE:
<223> OTHER INFORMATION: primer

<400> SEQUENCE: 12
aactctagac tcggtggact gtcaatg                                 27

<210> SEQ ID NO 13
<211> LENGTH: 25
<212> TYPE: DNA
<213> ORGANISM: Artificial Sequence
<220> FEATURE:
<223> OTHER INFORMATION: primer

<400> SEQUENCE: 13
catcgagaca agcacggtca acttc                                   25

<210> SEQ ID NO 14
<211> LENGTH: 24
<212> TYPE: DNA
<213> ORGANISM: Artificial Sequence
<220> FEATURE:
<223> OTHER INFORMATION: primer

<400> SEQUENCE: 14
atatccgagc gcctcgtgca tgcg                                    24

<210> SEQ ID NO 15
<211> LENGTH: 24
<212> TYPE: DNA
<213> ORGANISM: Artificial Sequence
<220> FEATURE:
<223> OTHER INFORMATION: primer

<400> SEQUENCE: 15
```

-continued

```
caagatggat tgcacgcagg ttct                                    24

<210> SEQ ID NO 16
<211> LENGTH: 23
<212> TYPE: DNA
<213> ORGANISM: Artificial Sequence
<220> FEATURE:
<223> OTHER INFORMATION: primer

<400> SEQUENCE: 16
atagaaggcg atgcgctgcg aat                                     23

<210> SEQ ID NO 17
<211> LENGTH: 29
<212> TYPE: DNA
<213> ORGANISM: Artificial Sequence
<220> FEATURE:
<223> OTHER INFORMATION: primer

<400> SEQUENCE: 17
cggaattcga tctagtaaca tagatgaca                               29

<210> SEQ ID NO 18
<211> LENGTH: 26
<212> TYPE: DNA
<213> ORGANISM: Artificial Sequence
<220> FEATURE:
<223> OTHER INFORMATION: primer

<400> SEQUENCE: 18
ggtctagaat ggaaactcac aaaacc                                  26

<210> SEQ ID NO 19
<211> LENGTH: 23
<212> TYPE: DNA
<213> ORGANISM: Artificial Sequence
<220> FEATURE:
<223> OTHER INFORMATION: primer

<400> SEQUENCE: 19
atagctgcga caaccctgtc ctt                                     23

<210> SEQ ID NO 20
<211> LENGTH: 26
<212> TYPE: DNA
<213> ORGANISM: Artificial Sequence
<220> FEATURE:
<223> OTHER INFORMATION: primer

<400> SEQUENCE: 20
gggagctctc aatcactctt accctc                                  26

<210> SEQ ID NO 21
<211> LENGTH: 21
<212> TYPE: DNA
<213> ORGANISM: Artificial Sequence
<220> FEATURE:
<223> OTHER INFORMATION: primer

<400> SEQUENCE: 21
aagcctgaac tcaccgcgac g                                       21

<210> SEQ ID NO 22
<211> LENGTH: 22
<212> TYPE: DNA
```

```
<213> ORGANISM: Artificial Sequence
<220> FEATURE:
<223> OTHER INFORMATION: primer

<400> SEQUENCE: 22
aagaccaatg cggagcatat ac                                              22

<210> SEQ ID NO 23
<211> LENGTH: 36
<212> TYPE: DNA
<213> ORGANISM: Artificial Sequence
<220> FEATURE:
<223> OTHER INFORMATION: primer

<400> SEQUENCE: 23
ggcgcatgcg aattcgaatt cgatatcgat cttcga                               36

<210> SEQ ID NO 24
<211> LENGTH: 369
<212> TYPE: DNA
<213> ORGANISM: barley
<220> FEATURE:
<221> NAME/KEY: misc_feature
<222> LOCATION: (0)...(0)
<223> OTHER INFORMATION: thioredoxin h

<400> SEQUENCE: 24 tggcggcgt cggcaacggc ggcggcagtg gcggcggagg tgatctcggt ccacagcctg       60 agcagtgga ccatgcagat cgaggaggcc aacaccgcca agaagctggt ggtgattgac      120 tcactgcat catggtgcgg accatgccgc atcatggctc cagttttcgc tgatctcgcc      180 agaagttcc caaatgctgt tttcctcaag gtcgacgtgg atgaactgaa gcccattgct      240 agcaattca gtgtcgaggc catgccaacg ttcctgttca tgaaggaagg agacgtcaag      300 acagggttg tcggagctat caaggaggaa ctgaccgcca aggttgggct tcacgcggcg      360
cccagtaa                                                             369

<210> SEQ ID NO 25
<211> LENGTH: 122
<212> TYPE: PRT
<213> ORGANISM: barley
<220> FEATURE:
<221> NAME/KEY: VARIANT
<222> LOCATION: (0)...(0)
<223> OTHER INFORMATION: thioredoxin h

<400> SEQUENCE: 25
```

Met Ala Ala Ser Ala Thr Ala Ala Ala Val Ala Ala Glu Val Ile Ser
 1               5                  10                  15

Val His Ser Leu Glu Gln Trp Thr Met Gln Ile Glu Glu Ala Asn Thr
                20                  25                  30

Ala Lys Lys Leu Val Val Ile Asp Phe Thr Ala Ser Trp Cys Gly Pro
            35                  40                  45

Cys Arg Ile Met Ala Pro Val Phe Ala Asp Leu Ala Lys Lys Phe Pro
        50                  55                  60

Asn Ala Val Phe Leu Lys Val Asp Val Asp Glu Leu Lys Pro Ile Ala
65                  70                  75                  80

Glu Gln Phe Ser Val Glu Ala Met Pro Thr Phe Leu Phe Met Lys Glu
                85                  90                  95

```
Gly Asp Val Lys Asp Arg Val Val Gly Ala Ile Lys Glu Glu Leu Thr
            100                 105                 110

Ala Lys Val Gly Leu His Ala Ala Ala Gln
            115                 120
```